United States Patent
Basu et al.

(10) Patent No.: US 9,556,449 B2
(45) Date of Patent: Jan. 31, 2017

(54) METHODS OF INCREASING YIELD AND STRESS TOLERANCE IN A PLANT BY DECREASING THE ACTIVITY OF A TREHALOSE-6-PHOSPHATE PHOSPHATASE

(75) Inventors: Shib Basu, Research Triangle Park, NC (US); Jonathan Cohn, Research Triangle Park, NC (US); Michael Nuccio, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 245 days.

(21) Appl. No.: 14/232,912

(22) PCT Filed: Jul. 16, 2012

(86) PCT No.: PCT/US2012/046888
§ 371 (c)(1),
(2), (4) Date: Feb. 3, 2014

(87) PCT Pub. No.: WO2013/012788
PCT Pub. Date: Jan. 24, 2013

(65) Prior Publication Data
US 2014/0143908 A1    May 22, 2014

Related U.S. Application Data

(60) Provisional application No. 61/508,609, filed on Jul. 15, 2011, provisional application No. 61/522,588, filed on Aug. 11, 2011.

(51) Int. Cl.
*C12N 15/82* (2006.01)
*C12N 9/16* (2006.01)

(52) U.S. Cl.
CPC ............. *C12N 15/8273* (2013.01); *C12N 9/16* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 6,833,490 B1 * | 12/2004 | Goddijn | C12N 9/1051 435/101 |
| 2007/0006344 A1 * | 1/2007 | Nuccio | C12N 15/827 800/284 |
| 2008/0148432 A1 | 6/2008 | Abad | |

FOREIGN PATENT DOCUMENTS

| | | |
|---|---|---|
| WO | 2005102034 | 11/2005 |
| WO | 2008071767 | 6/2008 |
| WO | WO 2008/071767 A1 * | 6/2008 |

OTHER PUBLICATIONS

Vandesteene et al., 2012, Plant Physiology 160: 884-896 with supplementary data.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Habibur Rahman Pramanik et al., "Functinoal Identification of a Trehalose 6-phosphate Phosphatase Gene that is Involved in Transient Induction of Trehalose Biosynthesis during Chilling Stress in Rice," Plant Molecular Biology, Kluwer Academic Publishers, Dordrecht, NL, 58(6), Aug. 1, 2005, pp. 751-762.
International Search Report and Written Opinion dated Nov. 7, 2012; and International Preliminary Report on Patentability for International Patent Application No. PCT/US2012/046341.
Garg, et al., "Trehalose accumulation in rice plants confers high tolerance levels to different abiotic stresses," Proceedings of the National Academy of Sciences, National Academy of Sciences, US, 99(25), Dec. 10, 2002, p. 15898-15903.
International Search Report and Written Opinion dated Jan. 30, 2013 for International Patent Application No. PCT/US2012/046888.

* cited by examiner

*Primary Examiner* — Amjad Abraham
*Assistant Examiner* — Bratislav Stankovic
(74) *Attorney, Agent, or Firm* — Karen Moon Bruce

(57) ABSTRACT

The present invention relates generally to the field of molecular biology and regards various polynucleotides, polypeptides and methods that may be employed to enhance yield in transgenic plants. Specifically the transgenic plants may exhibit any one of the traits consisting of increased yield, increased tolerance to abiotic stress, increased cell growth and increased nutrient use efficiency.

2 Claims, 15 Drawing Sheets

```
1                                                                  50
15777_O_sativa   MDLSNS..SP VITDPVAISQ QLLGGLPSNL MQFSVMPGGY SSSGMNVG..
19924_O_sativa   MDLKTSN.SP VIADPLPKLA LPSAVMTYTT PTSFPSTGLY LNTPKKK...
19925_A_thalia   MDMKSGHSSP VMTDSPPISN SRLTIRQNRL PYSSAAATAI SQNNLLLLTV
19926_A_thalia   ...MTNQNVI VSDRKPILGL KTTTVSVSNS PLFSNSEPTY FNFPRRKLLK
Q9HIW7           .......... .......... .......... .......... ..........

51                                                                 100
15777_O_sativa   .....VSRLK IEEVLVNGLL DAMKSSSP.R RRLNVAFGED NSSEEEDPAY
19924_O_sativa   ....PLPGK  IEEVRAAGWL DLMLASSPPR KRQTKDFAND VQADELDLLY
19925_A_thalia   ...PRKKTGI LDDVKSNGWL DAMKSSSP.. PPTILNKDNL .SNDATDMTY
19926_A_thalia   LLEAADKNNL VVAPKITSMI DSMRDSSP.. .......... ..........
Q9HIW7           .......... .......... .......... ...TRLRSSS YDSDSDNDDK 101                                                                150
15777_O_sativa   SAWM.AKCPS ALASFKQIVA SAQGKKIAVF LDYDGTLSPI VDDPDKAVMS
19924_O_sativa   RNWV.VNHPS ALTSFEDIVN LARGKRLALF LDYDGTLSPI VDNPENAVMS
19925_A_thalia   REWMQLKYPS ALTSFEKIMS FAKGKRIALF LDYDGTLSPI VEEPDCAYMS
19926_A_thalia   .......... .......... AAKGKQIVMF LDYDGTLSPI VEDPDKAFIT
Q9HIW7           TSWI.VRFPS ALNMFDEIVN .......MIF L*DYDGTLVPI IMNPEESYAD
```

FIG. 1A

```
                151                                                                         200
15777_O_sativa  PVMRAAVRNV AKYFPTAIVS GRSRNKVFEF VKLKELYYAG SHGMDIMAPS
19924_O_sativa  DEMRSAVKHV ASLFPTAIIS GRSRDKVFDF VKLTELYYAG SHGMDIMGPV
19925_A_thalia  SAMRSAVQNV AKYFPTAIIS GRSRDKVYEF VNLSELYYAG SHGMDIMSPA
19926_A_thalia  HEMREVVKDV ASNFPTAIVT GRSIEKVRSF VQVNEIYYAG SHGMDIEGPT
Q9HIW7          AGLLSLISDL KEREDTYIVT GRSPEEISRF LPLDINMICY HGACSKINGQ 201                                                                         250
15777_O_sativa  ANHEHSAE.. .........KS KQANLFQPAH DFLPMIDEVT KSLLQVVSGI
19924_O_sativa  RKSDSSGQHV ECIRSTDSEG KEVNLFQPAS EFLPMISEVY KKLSESIKDI
19925_A_thalia  GESLNHEHSR TV..SVYEQG KDVNLFQPAS EFLPMIDKVL CSLIESTKDI
19926_A_thalia  NENSNGQS.. .......... NERVLFQPAR EFLPMIEKVV NILEEKTKWI
Q9HIW7          IVYNNGSD.. .......... .......... RFLGVFDRIY EDTRSWVSDF 251                                                                         300
15777_O_sativa  EGATVENNKF CVSVHYRNVA EKDWKLVARL VNEVLEAFPR LKVTNGRMVL
19924_O_sativa  DGARMEDNKF CVSVHYRNVA PHDYGEVHQR VTAVLKNYPC LRLTHGRKVL
19925_A_thalia  KGVKVEDNKF CISVHYRNVE EKNWTLVAQC VDDVIRTYPK LRLTHGRKVL
19926_A_thalia  PGAMVENNKF CLSVHFRRVD EKRWPALAEV VKSVLIDYPK LKLTQGRKVL
Q9HIW7          PGLRIYRKNL AVLYHLGLMG ADMKPKLRSR IEEIARIFGV ETYYGKMIIE
```

*FIG. 1B*

```
                    301                                                          350
15777_O_sativa     EVRPVIDWDK  GKAVEFLLQS  LGLNDSENVI  PIYIGDDRTD  EDAFKVLRQR
19924_O_sativa     EVRPVIDWNK  GKAVEFLLES  LGLCGKEDVL  PIYVGDDKTD  EDAFKVLKAN
19925_A_thalia     EIRPVIDWDK  GKAVTFLLES  LGLNNCEDVL  PIYVGDDRTD  EDAFKVLRDG
19926_A_thalia     EIRPTIKWDK  GQALNFLLKS  LGYENSDDVV  PVYIGDDRTD  EDAFKVLRER
Q9HIW7             LRVPGVNKG.  ........S   AIRSVRGERP  AIIAG*DDATD*  EAAFEANDDA 351                                              396
15777_O_sativa     .NCGYGILVS  QVPKETEAFY  SLRDPSEVME  FLNFLVRWKK  HSV...
19924_O_sativa     .SIGFGILVS  SVPKDTDAFY  SVRDPAEVME  FLKKLASWKE  EST...
19925_A_thalia     PNHGYGILVS  AVPKDSNAFY  SLRDPSEVME  FLKSLVTWKR  SMG...
19926_A_thalia     .GQGFGILVS  KVPKDTNASY  SLQDPSQVNK  FLERLVEWKR  KTVGEE
Q9HIW7             ......LTIK  VGEGETHAKF  HVADYIEMRK  ILKFIEMLGV  QKKQ..
```

FIG. 1C

MXXXXXXXVVXDXXXXXXXXXXXXXXXXXXXXXXXXXXXXXXXXXXX
XXXXXXXXRXXGWVDSMRASSPTRXKXXXXXXXXXXSEXXDXXXSXXXXXXXXXXX
XXXXXXXXLKHPSALXFEXIVXAAKGKQIVMFLDYDGTLSPIVDDPDRAFMSDXMRXXXXXX
XXXXXXXXXXXAVRXVAKYFPTAIVSGRCRDKVYXFVKLXELYYAGSHGMDIKGPAK
XXXXXXXXXXXVLFQPASEFLPMIDEVYKXXLVERTKXXIPGAKVENNKFCVSVH
FRCVDEKXVWXLAXXVRSVLKEYPKLRLTQGRKVLEIRPXIKWDKGKALEFLLESLGFAXXXXXXXX
XNXXDVLPIYIGDDRTDEDAFKVLRERGQXXGFGILVSKXXPKETXASYSLQDPSEVMEXXXXXXXXXX
XXXXXXXXXFLXRLVXWKKXS

*FIG. 10*

```
                1                                                                    50
15777_O_sativa  MDLSNS..SP VITDPVAISQ QLLGGLPSNL MQFSVMPGGY SSSGMNVG..
19924_O_sativa  MDLKTSN.SP VIADPLPKLA LPSAVMTYTT PTSFPSTGLY LNTPKKK...
19925_A_thalia  MDMKSGHSSP VMTDSPPISN SRLTIRQNRL PYSSAAATAI SQNNLLLTV
19926_A_thalia  ...MTNQNVI VSDRKPILGL KTITVSVSNS PLFSNSFPTY FNFPRRKLLK
Q9HIW7          .......... .......... .......... .......... ..........

51                                                                   100
15777_O_sativa  .....VSRLK IEEVLVNGLL DAMKSSSP.R RRLNVAFGED NSSEEEDPAY
19924_O_sativa  .....PLPGK IEEVRAAGWL DLMLASSPPR KRQTKDFAND VQADELDLLY
19925_A_thalia  ...PRKKTGI LDDVKSNGWL DAMKSSSP.. PPTILNKDNL .SNDATDMTY
19926_A_thalia  LLEAADKNNL VVAPKITSMI DSMRDSSP.. .......... ..........
Q9HIW7          .......... .......... .......... ...TRLRSSS YDSDSDNDDK 101                                                                  150
15777_O_sativa  SAWM.AKCPS ALASFKQIVA SAQGKKIAVF LDYDGTLSPI VDDPDKAVMS
19924_O_sativa  RNWV.VNHPS ALTSFEDIVN LARGKRLALF LDYDGTLSPI VDNPENAVMS
19925_A_thalia  REWMQLKYPS ALTSFEKIMS FAKGKRIALF LDYDGTLSPI VEEPDCAYMS
19926_A_thalia  TSWI.VRFPS ALNMFDEIVN AAKGKQIVMF LDYDGTLSPI VEDPDKAFIT
Q9HIW7          .......... .......... ......MIF  LDY*DGT*LVPI IMNPEESYAD
```

FIG. 11A

```
              151
15777_O_sativa      PVMRAAVRNV AKYFPTAIVS GRSRNKVFEF VKLKELYYAG SHGMDIMAPS
19924_O_sativa      DEMRSAVKHV ASLFPTAIIS GRSRDKVFDF VKLTELYYAG SHGMDIMGPV
19925_A_thalia      SAMRSAVQNV AKYFPTAIIS GRSRDKVYEF VNLSELYYAG SHGMDIMSPA
19926_A_thalia      HEMREVVKDV ASNFPTAIVT GRSIEKVRSF VQVNEIYYAG SHGMDIEGPT
Q9HIW7              AGLLSLISDL KERFDTYIVT GRSPEEISRF LPL.DINMIC YHGACSKIN.
                                         ‾‾
              201                                                    250
15777_O_sativa      ANHEHSAE.. ........KS KQANLFQPAH DFLPMIDEVT KSLLQVVSGI
19924_O_sativa      RKSDSSGQHV ECIRSTDSEG KEVNLFQPAS EFLPMISEVY KKLSESIKDI
19925_A_thalia      GESLNHEHSR TV..SVYEQG KDVNLFQPAS EFLPMIDKVL CSLIESTKDI
19926_A_thalia      NENSNGQS.. .......... NERVLFQPAR EFLPMIEKVV NILEEKTKWI
Q9HIW7              .......... .......... GQIVYNNGSD RFLGVFDRIY EDTRSWVSDF 251                                                    300
15777_O_sativa      EGATVENNKF CVSVHYRNVA EKDWKLVARL VNEVLEAFPR LKVTNGRMVL
19924_O_sativa      DGARMEDNKF CVSVHYRNVA PHDYGEVHQR VTAVLKNYPC LRLTHGRKVL
19925_A_thalia      KGVKVEDNKF CISVHYRNVE EKNWTLVAQC VDDVIRTYPK LRLTHGRKVL
19926_A_thalia      PGAMVENNKF CLSVHFRRVD EKRWPALAEV VKSVLIDYPK LKLTQGRKVL
Q9HIW7              PGLRIYRKNL AVLYHLGLMG ADMKPKLRSR IEEIARIFG. VETYYGKMII
```

*FIG. 11B*

```
                 301                                                                    350
15777_O_sativa   EVRPVIDWDK GKAVEFLLQS LGLNDSENVI PIYIGDDRTD EDAFKVLRQR
19924_O_sativa   EVRPVIDWNK GKAVEFLLES LGLCGKEDVL PIYVGDDKTD EDAFKVLKAN
19925_A_thalia   EIRPVIDWDK GKAVTFLLES LGLNNCEDVL PIYVGDDRTD EDAFKVLRDG
19926_A_thalia   EIRPTIKWDK GQALNFLLKS LGYENSDDVV PVYIGDDRTD EDAFKVLRER
Q9HIW7           ELR.VPGVNK G.........S AIRSVRGERP AIIAGDDATD EAAFEANDD.

351                                                                    396
15777_O_sativa   .NCCYGILVS QVPKETEAFY SLRDPSEVME FLNFLVRWKK HSV....
19924_O_sativa   .SIGFGILVS SVPKDTDAFY SVRDPAEVME FLKKLASWKE EST....
19925_A_thalia   PNHGYGILVS AVPKDSNAFY SLRDPSEVME FLKSLVTWKR SMG....
19926_A_thalia   .GQGFGILVS KVPKDTNASY SLQDPSQVNK FLERLVEWKR KTVGEE
Q9HIW7           ......ALTI KVGEGETHAK FHVADYIEMR KILKFIEMLG VQKKQ.
```

FIG. 11C

SEQUENCE LISTING

<160> NUMBER OF SEQ ID NOS: 21

<210> SEQ ID NO 1
<211> LENGTH: 1116
<212> TYPE: DNA
<213> ORGANISM: Oryza sativa

<400> SEQUENCE: 1

```
atggatttga gcaatagctc acctgtcatc accgatccgg tggcgatcag ccagcagttg      60
ttgggcggcc tgccttcaaa tctgatgcag ttttcagtca tgcccggtgg ctactccagc     120
tctggcatga acgttggtgt cagtaggctc aaaatcgagg aagtccttgt caatggactg     180
cttgatgcca tgaaatcctc gtcacctcgc aggaggctga atgtagcatt tggcgaggac     240
aattcatctg aagaagaaga ccctgcttac agcgcttgga tggcaaaatg tccttctgct     300
ttggcttcct tcaagcaaat tgtagccagt gcacaaggga agaagattgc tgtgtttcta     360
gactatgacg gcacactgtc gcctattgtg gatgatcctg acaaagcagt gatgtctccc     420
gtgatgagag ctgctgtgag aaatgttgcg aagtacttcc ccactgcaat tgtcagcgga     480
aggtcccgca ataaggtgtt tgaatttgta aaactgaagg agctttatta tgctggaagt     540
catggtatgg acataatggc accttcagca aatcatgagc acagtgctga aaagagcaaa     600
caggccaatc tcttccaacc tgcacacgac tttctgccaa tgatcgatga ggttaccaag     660
tccctcttgc aagttgtcag tggaattgaa ggtgcaactg ttgagaacaa caaattctgc     720
gtttctgtac attatcgcaa cgttgcagag aaggattgga aactggtcgc acggctcgta     780
aacgaagtgc tggaggcttt tcctcgtctc aaagtaacca atggacgaat ggttttagag     840
gttcgtccgg tgatcgactg ggacaaggga aaggctgtgg agtttctgct ccagtcactc     900
gggctaaatg actctgaaaa tgtgatcccc atctacattg agacgacag aactgacgaa     960 gacgctttca aggtacttcg acagcgaaat tgcggttatg gaatactagt ttcacaggtt    1020
```

```
cccaaggaaa ctgaagccTT ctactcgctg agagatccat ctgaagtgat ggagttcctc    1080
aatttcttgg tgagatggaa gaagcactca gtgtga                              1116
```

<210> SEQ ID NO 2
<211> LENGTH: 371
<212> TYPE: PRT
<213> ORGANISM: Oryza sativa

<400> SEQUENCE: 2

```
Met Asp Leu Ser Asn Ser Ser Pro Val Ile Thr Asp Pro Val Ala Ile
1               5                   10                  15

Ser Gln Gln Leu Leu Gly Gly Leu Pro Ser Asn Leu Met Gln Phe Ser
            20                  25                  30

Val Met Pro Gly Gly Tyr Ser Ser Gly Met Asn Val Gly Val Ser
        35                  40                  45

Arg Leu Lys Ile Glu Glu Val Leu Val Asn Gly Leu Leu Asp Ala Met
50                  55                  60

Lys Ser Ser Ser Pro Arg Arg Leu Asn Val Ala Phe Gly Glu Asp
65                  70                  75                  80

Asn Ser Ser Glu Glu Glu Asp Pro Ala Tyr Ser Ala Trp Met Ala Lys
                85                  90                  95

Cys Pro Ser Ala Leu Ala Ser Phe Lys Gln Ile Val Ala Ser Ala Gln
            100                 105                 110

Gly Lys Lys Ile Ala Val Phe Leu Asp Tyr Asp Gly Thr Leu Ser Pro
        115                 120                 125

Ile Val Asp Asp Pro Asp Lys Ala Val Met Ser Pro Val Met Arg Ala
130                 135                 140

Ala Val Arg Asn Val Ala Lys Tyr Phe Pro Thr Ala Ile Val Ser Gly
145                 150                 155                 160

Arg Ser Arg Asn Lys Val Phe Glu Phe Val Lys Leu Lys Glu Leu Tyr
                165                 170                 175

Tyr Ala Gly Ser His Gly Met Asp Ile Met Ala Pro Ser Ala Asn His
            180                 185                 190

Glu His Ser Ala Glu Lys Ser Lys Gln Ala Asn Leu Phe Gln Pro Ala
        195                 200                 205

His Asp Phe Leu Pro Met Ile Asp Glu Val Thr Lys Ser Leu Leu Gln
210                 215                 220

Val Val Ser Gly Ile Glu Gly Ala Thr Val Glu Asn Asn Lys Phe Cys
225                 230                 235                 240

Val Ser Val His Tyr Arg Asn Val Ala Glu Lys Asp Trp Lys Leu Val
                245                 250                 255

Ala Arg Leu Val Asn Glu Val Leu Glu Ala Phe Pro Arg Leu Lys Val
            260                 265                 270

Thr Asn Gly Arg Met Val Leu Glu Val Arg Pro Val Ile Asp Trp Asp
        275                 280                 285

Lys Gly Lys Ala Val Glu Phe Leu Leu Gln Ser Leu Gly Leu Asn Asp
290                 295                 300

Ser Glu Asn Val Ile Pro Ile Tyr Ile Gly Asp Asp Arg Thr Asp Glu
305                 310                 315                 320

Asp Ala Phe Lys Val Leu Arg Gln Arg Asn Cys Gly Tyr Gly Ile Leu
                325                 330                 335

Val Ser Gln Val Pro Lys Glu Thr Glu Ala Phe Tyr Ser Leu Arg Asp
            340                 345                 350
```

```
Pro Ser Glu Val Met Glu Phe Leu Asn Phe Leu Val Arg Trp Lys Lys
        355                 360                 365
His Ser Val
    370

<210> SEQ ID NO 3
<211> LENGTH: 1113
<212> TYPE: DNA
<213> ORGANISM: Oryza sativa

<400> SEQUENCE: 3
atggatctga gcaacagcag cccggtgatt accgatccgg tggcgattag ccagcagctg      60
ctgggcggcc tgccgagcaa cctgatgcag tttagcgtga tgccgggcgg ctatagcagc     120
agcggcatga acgtgggcgt gagccgcctg aaaattgaag aagtgctggt gaacggcctg     180
ctggatgcga tgaaaagcag cagcccgcgc cgccgcctga acgtggcgtt tggcgaagat     240
aacagcagcg aagaagaaga tccggcgtat agcgcgtgga tggcgaaatg cccgagcgcg     300
ctggcgagct ttaaacagat tgtggcgagc gcgcagggca aaaaaattgc ggtgtttctg     360
gattatgatg gcacccctga gcccgattgtg gatgatccgg ataaagcggt gatgagcccg     420
gtgatgcgcg cggcggtgcg caacgtggcg aaatattttc cgaccgcgat gtgagcggc      480 cgcagccgca acaaagtgtt tgaatttgtg aaactgaaag aactgtatta tgcgggcagc     540
catggcatgg atattatggc gccgagcgcg aaccatgaac atagcgcgga aaaaagcaaa     600
caggcgaacc tgtttcagcc ggcgcatgat tttctgccga tgattgatga agtgaccaaa     660
agcctgctgc aggtggtgag cggcattgaa ggcgcgaccg tggaaaacaa caaattttgc     720
gtgagcgtgg attatcgcaa cgtggcggaa aaagattgga actggtggc gcgcctggtg      780 aacgaagtgc tggaagcgtt tccgcgcctg aaagtgacca acggccgcat ggtgctggaa     840
gtgcgcccgg tgattgattg ggataaaggc aaagcggtgg aatttctgct gcagagcctg     900
ggcctgaacg atagcgaaaa cgtgattccg atttatattg gcgatgatcg caccgatgaa     960
gatgcgttta agtgctgcg ccagcgcaac tgcggctatg gcattctggt gagccaggtg     1020
ccgaaagaaa ccgaagcgtt ttatagcctg cgcgatccga gcgaagtgat ggaatttctg     1080
aactttctgg tgcgctggaa aaaacatagc gtg                                  1113

<210> SEQ ID NO 4
<211> LENGTH: 371
<212> TYPE: PRT
<213> ORGANISM: Oryza sativa

<400> SEQUENCE: 4

Met Asp Leu Ser Asn Ser Ser Pro Val Ile Thr Asp Pro Val Ala Ile
1               5                   10                  15

Ser Gln Gln Leu Leu Gly Gly Leu Pro Ser Asn Leu Met Gln Phe Ser
            20                  25                  30

Val Met Pro Gly Gly Tyr Ser Ser Ser Gly Met Asn Val Gly Val Ser
        35                  40                  45

Arg Leu Lys Ile Glu Glu Val Leu Val Asn Gly Leu Leu Asp Ala Met
    50                  55                  60

Lys Ser Ser Ser Pro Arg Arg Arg Leu Asn Val Ala Phe Gly Glu Asp
65                  70                  75                  80

Asn Ser Ser Glu Glu Glu Asp Pro Ala Tyr Ser Ala Trp Met Ala Lys
                85                  90                  95
```

Cys Pro Ser Ala Leu Ala Ser Phe Lys Gln Ile Val Ala Ser Ala Gln
            100                 105                 110

Gly Lys Lys Ile Ala Val Phe Leu Asp Tyr Asp Gly Thr Leu Ser Pro
        115                 120                 125

Ile Val Asp Asp Pro Asp Lys Ala Val Met Ser Pro Val Met Arg Ala
130                 135                 140

Ala Val Arg Asn Val Ala Lys Tyr Phe Pro Thr Ala Ile Val Ser Gly
145                 150                 155                 160

Arg Ser Arg Asn Lys Val Phe Glu Phe Val Lys Leu Lys Glu Leu Tyr
                165                 170                 175

Tyr Ala Gly Ser His Gly Met Asp Ile Met Ala Pro Ser Ala Asn His
            180                 185                 190

Glu His Ser Ala Glu Lys Ser Lys Gln Ala Asn Leu Phe Gln Pro Ala
        195                 200                 205

His Asp Phe Leu Pro Met Ile Asp Glu Val Thr Lys Ser Leu Leu Gln
210                 215                 220

Val Val Ser Gly Ile Glu Gly Ala Thr Val Glu Asn Asn Lys Phe Cys
225                 230                 235                 240

Val Ser Val Asp Tyr Arg Asn Val Ala Glu Lys Asp Trp Lys Leu Val
                245                 250                 255

Ala Arg Leu Val Asn Glu Val Leu Glu Ala Phe Pro Arg Leu Lys Val
            260                 265                 270

Thr Asn Gly Arg Met Val Leu Glu Val Arg Pro Val Ile Asp Trp Asp
        275                 280                 285

Lys Gly Lys Ala Val Glu Phe Leu Leu Gln Ser Leu Gly Leu Asn Asp
290                 295                 300

Ser Glu Asn Val Ile Pro Ile Tyr Ile Gly Asp Asp Arg Thr Asp Glu
305                 310                 315                 320

Asp Ala Phe Lys Val Leu Arg Gln Arg Asn Cys Gly Tyr Gly Ile Leu
                325                 330                 335

Val Ser Gln Val Pro Lys Glu Thr Glu Ala Phe Tyr Ser Leu Arg Asp
            340                 345                 350

Pro Ser Glu Val Met Glu Phe Leu Asn Phe Leu Val Arg Trp Lys Lys
        355                 360                 365

His Ser Val
    370

<210> SEQ ID NO 5
<211> LENGTH: 1113
<212> TYPE: DNA
<213> ORGANISM: Oryza sativa

<400> SEQUENCE: 5

```
atggatctga gcaacagcag cccggtgatt accgatccgg tggcgattag ccagcagctg      60
ctgggcggcc tgccgagcaa cctgatgcag tttagcgtga tgccgggcgg ctatagcagc     120
agcggcatga acgtgggcgt gagccgcctg aaaattgaag aagtgctggt gaacggcctg     180
ctggatgcga tgaaaagcag cagcccgcgc cgccgcctga acgtggcgtt tggcgaagat     240
aacagcagcg aagaagaaga tccggcgtat agcgcgtgga tggcgaaatg cccgagcgcg     300
ctggtgagct ttaaacagat tgtggcgagc gcgcagggca aaaaaattgc ggtgtttctg     360
gattatgatg gcaccctgag cccgtttgtg gatgatccgg ataaagcggt gatgagcccg     420
gtgatgcgcg cggcggtgcg caacgtggcg aaatattttc cgaccgcgat tgtgagcggc     480
cgcagccgca acaaagtgtt tgaatttgtg aaactgaaag aactgtatta tgcgggcagc     540
```

```
catggcatgg atattatggc gccgagcgcg aaccatgaac atagcgcgga aaaaagcaaa      600
caggcgaacc tgtttcagcc ggcgcatgat tttctgccga tgattgatga agtgaccaaa      660
agcctgctgc aggtggtgag cggcattgaa ggcgcgaccg tggaaaacaa caaatttttgc     720 gtgagcgtgc attatcgcaa cgtggcggaa aaagattgga aactggtggc gcgcctggtg      780
aacgaagtgc tggaagcgtt tccgcgcctg aaagtgacca acggccgcat ggtgctggaa      840
gtgcgcccgg tgattgattg gataaaggc aaagcggtgg aatttctgct gcagagcctg      900
ggcctgaacg atagcgaaaa cgtgattccg atttatattg gcgatgatcg caccgatgaa      960
gatgcgttta agtgctgcg ccagcgcaac tgcggctatg cattctggt gagccaggtg       1020 ccgaaagaaa ccgaagcgtt ttatagcctg cgcgatccga gcgaagtgat ggaatttctg      1080
aactttctgg tgcgctggaa aaacatagc gtg                                     1113
```

<210> SEQ ID NO 6
<211> LENGTH: 371
<212> TYPE: PRT
<213> ORGANISM: Oryza sativa

<400> SEQUENCE: 6

```
Met Asp Leu Ser Asn Ser Ser Pro Val Ile Thr Asp Pro Val Ala Ile
1               5                   10                  15

Ser Gln Gln Leu Leu Gly Gly Leu Pro Ser Asn Leu Met Gln Phe Ser
            20                  25                  30

Val Met Pro Gly Gly Tyr Ser Ser Gly Met Asn Val Gly Val Ser
        35                  40                  45

Arg Leu Lys Ile Glu Glu Val Leu Val Asn Gly Leu Leu Asp Ala Met
    50                  55                  60

Lys Ser Ser Ser Pro Arg Arg Leu Asn Val Ala Phe Gly Glu Asp
65                  70                  75                  80

Asn Ser Ser Glu Glu Glu Asp Pro Ala Tyr Ser Ala Trp Met Ala Lys
                85                  90                  95

Cys Pro Ser Ala Leu Val Ser Phe Lys Gln Ile Val Ala Ser Ala Gln
            100                 105                 110

Gly Lys Lys Ile Ala Val Phe Leu Asp Tyr Asp Gly Thr Leu Ser Pro
        115                 120                 125

Phe Val Asp Asp Pro Asp Lys Ala Val Met Ser Pro Val Met Arg Ala
    130                 135                 140

Ala Val Arg Asn Val Ala Lys Tyr Phe Pro Thr Ala Ile Val Ser Gly
145                 150                 155                 160

Arg Ser Arg Asn Lys Val Phe Glu Phe Val Lys Leu Lys Glu Leu Tyr
                165                 170                 175

Tyr Ala Gly Ser His Gly Met Asp Ile Met Ala Pro Ser Ala Asn His
            180                 185                 190

Glu His Ser Ala Glu Lys Ser Lys Gln Ala Asn Leu Phe Gln Pro Ala
        195                 200                 205

His Asp Phe Leu Pro Met Ile Asp Glu Val Thr Lys Ser Leu Leu Gln
    210                 215                 220

Val Val Ser Gly Ile Glu Gly Ala Thr Val Glu Asn Asn Lys Phe Cys
225                 230                 235                 240

Val Ser Val His Tyr Arg Asn Val Ala Glu Lys Asp Trp Lys Leu Val
                245                 250                 255
```

```
Ala Arg Leu Val Asn Glu Val Leu Glu Ala Phe Pro Arg Leu Lys Val
        260                 265                 270

Thr Asn Gly Arg Met Val Leu Glu Val Arg Pro Val Ile Asp Trp Asp
        275                 280                 285

Lys Gly Lys Ala Val Glu Phe Leu Leu Gln Ser Leu Gly Leu Asn Asp
        290                 295                 300

Ser Glu Asn Val Ile Pro Ile Tyr Ile Gly Asp Asp Arg Thr Asp Glu
305                 310                 315                 320

Asp Ala Phe Lys Val Leu Arg Gln Arg Asn Cys Gly Tyr Gly Ile Leu
                325                 330                 335

Val Ser Gln Val Pro Lys Glu Thr Glu Ala Phe Tyr Ser Leu Arg Asp
        340                 345                 350

Pro Ser Glu Val Met Glu Phe Leu Asn Phe Leu Val Arg Trp Lys Lys
        355                 360                 365

His Ser Val
    370

<210> SEQ ID NO 7
<211> LENGTH: 1113
<212> TYPE: DNA
<213> ORGANISM: Oryza sativa

<400> SEQUENCE: 7
atggatctga gcaacagcag cccggtgatt accgatccgg tggcgattag ccagcagctg      60
ctgggcggcc tgccgagcaa cctgatgcag tttagcgtga tgccgggcgg ctatagcagc     120
agcggcatga acgtgggcgt gagccgcctg aaaattgaag aagtgctggt gaacggcctg     180
ctggatgcga tgaaaagcag cagcccgcgc cgccgcctga acgtggcgtt tggcgaagat     240
aacagcagcg aagaagaaga tccggcgtat agcgcgtgga tggcgaaatg cccgagcgcg     300
ctggcgagct ttaaacagat tgtggcgagc gcgcagggca aaaaaattgc ggtgtttctg     360
gattatgatg caccctgag cccgtttgtg gatgatccgg ataaagcggt gatgagcccg     420
gtgatgcgcg cggcggtgcg caacgtggcg aaatattttc cgaccgcgat tgtgagcggc     480
cgcagccgca caaagtgtt tgaatttgtg aaactgaaag aactgtatta tgcgggcagc     540
catggcatgg atattatggc gccgagcgcg aaccatgaac atagcgcgga aaaagcaaa     600 caggcgaacc tgtttcagcc ggcgcatgat tttctgccga tgattgatga agtgaccaaa     660
agcctgctgc aggtggtgag cggcattgaa ggcgcgaccg tggaaaacaa caaattttgc     720
gtgagcgtgg attatcgcaa cgtggcggaa aaagattgga actggtggc gcgcctggtg     780 aacgaagtgc tggaagcgtt tccgcgcctg aaagtgacca acggccgcat ggtgctggaa     840
gtgcgcccgg tgattgattg gataaaggc aaagcggtgg aatttctgct gcagagcctg     900
ggcctgaacg atagcgaaaa cgtgattccg atttatattg gcgatgatcg caccgatgaa     960
gatgcgttta agtgctgcg ccagcgcaac tgcggctatg gcattctggt gagccaggtg    1020
ccgaaagaaa ccgaagcgtt ttatagcctg cgcgatccga gcgaagtgat ggaatttctg    1080
aactttctgg tgcgctggaa aaaacatagc gtg                                 1113

<210> SEQ ID NO 8
<211> LENGTH: 371
<212> TYPE: PRT
<213> ORGANISM: Oryza sativa
```

<400> SEQUENCE: 8

```
Met Asp Leu Ser Asn Ser Ser Pro Val Ile Thr Asp Pro Val Ala Ile
1               5                   10                  15

Ser Gln Gln Leu Leu Gly Gly Leu Pro Ser Asn Leu Met Gln Phe Ser
            20                  25                  30

Val Met Pro Gly Gly Tyr Ser Ser Gly Met Asn Val Gly Val Ser
        35                  40                  45

Arg Leu Lys Ile Glu Glu Val Leu Val Asn Gly Leu Leu Asp Ala Met
        50                  55                  60

Lys Ser Ser Pro Arg Arg Leu Asn Val Ala Phe Gly Glu Asp
65                  70                  75                  80

Asn Ser Ser Glu Glu Glu Asp Pro Ala Tyr Ser Ala Trp Met Ala Lys
                85                  90                  95

Cys Pro Ser Ala Leu Ala Ser Phe Lys Gln Ile Val Ala Ser Ala Gln
            100                 105                 110

Gly Lys Lys Ile Ala Val Phe Leu Asp Tyr Asp Gly Thr Leu Ser Pro
            115                 120                 125

Phe Val Asp Asp Pro Asp Lys Ala Val Met Ser Pro Val Met Arg Ala
        130                 135                 140

Ala Val Arg Asn Val Ala Lys Tyr Phe Pro Thr Ala Ile Val Ser Gly
145                 150                 155                 160

Arg Ser Arg Asn Lys Val Phe Glu Phe Val Lys Leu Lys Glu Leu Tyr
                165                 170                 175

Tyr Ala Gly Ser His Gly Met Asp Ile Met Ala Pro Ser Ala Asn His
            180                 185                 190

Glu His Ser Ala Glu Lys Ser Lys Gln Ala Asn Leu Phe Gln Pro Ala
        195                 200                 205

His Asp Phe Leu Pro Met Ile Asp Glu Val Thr Lys Ser Leu Leu Gln
210                 215                 220

Val Val Ser Gly Ile Glu Gly Ala Thr Val Glu Asn Asn Lys Phe Cys
225                 230                 235                 240

Val Ser Val Asp Tyr Arg Asn Val Ala Glu Lys Asp Trp Lys Leu Val
                245                 250                 255

Ala Arg Leu Val Asn Glu Val Leu Glu Ala Phe Pro Arg Leu Lys Val
            260                 265                 270

Thr Asn Gly Arg Met Val Leu Glu Val Arg Pro Val Ile Asp Trp Asp
        275                 280                 285

Lys Gly Lys Ala Val Glu Phe Leu Leu Gln Ser Leu Gly Leu Asn Asp
290                 295                 300

Ser Glu Asn Val Ile Pro Ile Tyr Ile Gly Asp Asp Arg Thr Asp Glu
305                 310                 315                 320

Asp Ala Phe Lys Val Leu Arg Gln Arg Asn Cys Gly Tyr Gly Ile Leu
                325                 330                 335

Val Ser Gln Val Pro Lys Glu Thr Glu Ala Phe Tyr Ser Leu Arg Asp
            340                 345                 350

Pro Ser Glu Val Met Glu Phe Leu Asn Phe Leu Val Arg Trp Lys Lys
        355                 360                 365

His Ser Val
        370

<210> SEQ ID NO 9
<211> LENGTH: 208
<212> TYPE: PRT
<213> ORGANISM: Artificial Sequence
```

```
<220> FEATURE:
<223> OTHER INFORMATION: Consensus Sequence
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (64)..(65)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (110)..(118)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid
<220> FEATURE:
<221> NAME/KEY: misc_feature
<222> LOCATION: (147)..(148)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (176)..(196)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid

<400> SEQUENCE: 9

Lys Xaa Xaa Xaa Xaa Xaa Xaa Val Leu Phe Gln Pro Ala Ser Glu Phe
1               5                   10                  15

Leu Pro Met Ile Asp Glu Val Tyr Lys Xaa Leu Val Glu Lys Thr Lys
                20                  25                  30

Xaa Xaa Ile Pro Gly Ala Lys Val Glu Asn Asn Lys Phe Cys Val Ser
            35                  40                  45
```

Val His Phe Arg Cys Val Asp Glu Lys Xaa Trp Xaa Xaa Leu Ala Xaa
    50                  55                  60

Xaa Val Arg Ser Val Leu Lys Glu Tyr Pro Lys Leu Arg Leu Thr Gln
 65                  70                  75                  80

Gly Arg Lys Val Leu Glu Ile Arg Pro Xaa Ile Lys Trp Asp Lys Gly
                 85                  90                  95

Lys Ala Leu Glu Phe Leu Leu Glu Ser Leu Gly Phe Ala Xaa Xaa Xaa
                100                 105                 110

Xaa Xaa Xaa Xaa Xaa Asn Xaa Asp Val Leu Pro Ile Tyr Ile
        115                 120                 125

Gly Asp Asp Arg Thr Asp Glu Asp Ala Phe Lys Val Leu Arg Glu Arg
    130                 135                 140

Gly Gln Xaa Xaa Gly Phe Gly Ile Leu Val Ser Lys Xaa Pro Lys Glu
145                 150                 155                 160

Thr Xaa Ala Ser Tyr Ser Leu Gln Asp Pro Ser Glu Val Met Glu Xaa
                165                 170                 175

Xaa Xaa Xaa Xaa Xaa Xaa Xaa Xaa Xaa Xaa Xaa Xaa Xaa Xaa Xaa Xaa
        180                 185                 190

Xaa Xaa Xaa Xaa Phe Leu Xaa Arg Leu Val Xaa Trp Lys Lys Xaa Ser
        195                 200                 205

<210> SEQ ID NO 10
<211> LENGTH: 19
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 10

Arg Xaa Xaa Ser Trp Val Asp Ser Met Arg Ala Ser Ser Pro Thr Xaa
 1               5                  10                  15

Xaa Lys Ser

<210> SEQ ID NO 11
<211> LENGTH: 10
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 11

Gly Asp Asp Arg Thr Xaa Gln Asp Ala Phe
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Consensus Sequence

<400> SEQUENCE: 12

Leu Asp Tyr Asp Gly Thr Leu Ser Pro Ile Val Asp
1               5                   10

<210> SEQ ID NO 13
<211> LENGTH: 4447
<212> TYPE: DNA
<213> ORGANISM: Oryza sativa

<400> SEQUENCE: 13

```
cggaccgcta ggacgatggt gtgatgtggg aacacgaaga aacatgagg aaaaaatatt      60
aaaatgaatt tcccacttaa aatgcatcaa ataaaaaaaa taaagaaacg accgggaata   120
gacacagggt ttgtgaacta gctagggcaa acatcatatg gtcccttgct gatgcacaag   180
tacattgaga gtgtcatttca attctgtgca tcatatgcat gtggtcccct gctgaatatt   240
actcttgaaa tatctaccag tgccaatcta ttgcatgact taattaattc acaggttttg   300
ttgattacat tattagtaag cttgagagca caagctcaat ggattttct ataaatgggg    360
atcattttgc aattttcttt gtcgtgcaaa gttagccttc tttattacta cttctgtttt   420
taaatatacg atcctattga cttttggtca tatatttaac catgtatctt atttagatag   480
tttgcgcaaa tatatatacc ttcaatgata aaattagtta caatgaaaca atgatatt     540
acgcaattct ttttactaaa caagtcacaa gaagtacctg cagcaatata tgttggaacc   600
gtgcagtaga tcgagcctag ctacgcaaaa aaacaaaaag agaaaaaaag ggaaaggaaa   660
aacattaatc atgcatgagc agtatgcccg gcaactggaa tttgtcaaag atatggggag   720
aggagaataa tacaagtact actactacct agctctacca tgcatatgca cccaaaggca   780
aactggatta ttggataaag cacagatgct ggcaaaacaa tccttaagcc tcccctccct   840
gcttctttat ttttgggcag cctctaccgg acggtgccgt ggtccattgg accagtaggt   900
ggcgacatac atggtttggg ttaagtctag gagagcagtg tgtgtgcgcg cgcaagagag   960
agagactgtg agtctgggag tagccctctc ccctcctttg gccatcttcc tcgtgtatat  1020
gcatatatgc atcatcgcaa cggtgtatat ttgtggtgtg gcgggtgtgg cattggattg  1080
cccccatttt ggctcgtgct tcccagttag ggtaaaacct gtggtaaact tgctagcccc  1140
acgccaaagt taccctttctt tattgttgaa agggagagga ggtgtgtgaa ttgtgatgga  1200
gggagagaga gagagagata gaaagagaga tgtgtgtcaa agcaagcaag aaaccagttt  1260
cacaaagagc tactactagt actagtgtac tactgtggta cagtgcccaa tgtcctttct  1320
ccggactcga ctccactaat attctcctct tctcgcgcgg ctcgttatat tctcgtcatc  1380
attggaggct ttagcaagca agaagagagg cagtggtggt ggtggtggag gaggagctag  1440
ctagcctgtg cttgctgatc ggtgctgagc tgaggaatcg ttcgatcgat cgggcgagtc  1500
gacgagggga agagttgagc tgaggcgcat cgagaacaag atcaacaggc aggtcacctt  1560
ctccaagcgc cgcaacggcc tcctcaagaa ggcctacgag ctgtccgttc tctgcgacgc  1620
cgaggtcgcg ctcatcatct tctccagccg cggcaagctc tacgagttcg cagcgccgg   1680
gtataattaa tacagacaca acaacacaca caaccaacaa accagcatca atttgaacct  1740
gcagatctgc tgttttctct gatcaattgc ttcttttttt ttgttcttt ttgtttcttt    1800
tatctgctgc aacggcgtcc tgctcctctg gggtttctcg ttttcttttt catttatttt  1860
tagcaggtgc caagtagccg agctactata cttacctggc catgttaatt attttattcc  1920
gtctgtctgt gtgtgtctgt gcatactact atagggacat ggcgcggtgt tcttataaac  1980
```

```
cgggaggccg gatccctaac tagcatggga ggatatcttt tcagcggatc tatacaaacc   2040
ctactcctgc tgacctcttt cttccagttt ctccgggtct tccttggatt attattgccc   2100
atcttccggg ttgtgcgtgt gtcagagaca gctcgaacga taaatttctc aaaaccagta   2160
ctagagaggg tgtgttgtgt gtgagaactg agtggagagt tagcatgaag gctgcaaact   2220
agaaaggaag gtatgttctt ccttttttga tccatcaggg gagccccttc tggtattaag   2280
atctttccgg cacattgatt ttcatacttt gtgatgaccc tggaagaatc ggcgtagcag   2340
cgtagcaccg ctccattttg gtcttaccct cacctcccca tgctatgaac tgatcaattt   2400
cattgttctt catcacccct ctcctagctt tccacttcct tcggatctca tgccatgttt   2460
ctcagcatga atcaaattta attcgtgttt tctacttcca tatatactgg aagaaattta   2520
attagatcta tttttgctcg ggaggtcttc atactttgag ttctgatgcc atcaccttat   2580 ttccccccc ccttctctt gttctatctt cttcctcatc ttggcttgat cattttgatc   2640
tgtcagttat agcatgatgc attctcaatt tgactgtatg taagttcaac cggaaatatg   2700
ttgaatggat tttctatata tcaacacttg atgtcaggcc tgcatctgtt tcgcttgtgg   2760
tggtgtggcc aaaattgtct atatttgatc tttgctcttc tttctcctca tttcatgacg   2820
attcctacta cggcttaaac cattcttat tctttactaa tcatggatgt tgcttgactc   2880
ctagttgttt cgtactagct caacttggag atcttttcat tatttgccta gttggtgggt   2940
acgtttgtga cagatctaaa atggtgcacg aaaagtttta cttattatga aaaagggag   3000 cttaacaggg taatttctct atttattcgt gatgacattt tttccttgat aaggggatt   3060 ttttataatc tgcactcaca tgtttatatg taaaatctag ctcttttgtt ttgttttgg   3120 catatttccc gctaagtata gagtttatgt ggataacatt ataactttc aagatccaat   3180 ccacatcttt gattgtgaaa atcatacaat agggaaaatc aactgaaggg ttaattagat   3240
gctatatgca tatatatata tatgtgcgcg cgcgcgcgcc tgaatttaac tatgtatgca   3300
tccaactgtt tcattgaaaa agatttgata tttttcagtc tattcttttt cgagtatata   3360
tttaatatgt ttcaatctgt tttgaccatt ataagataaa gcctatattc accaggcatt   3420
tgagatgatc ttttcatgca tgaaaaagct gttgttatca cttcaactaa ccagacgatc   3480
taacatgtat ttgtataaga aacagacctt gatttccttc tgtaaaatca tgcatgtgtt   3540
cgttttgaat tggagtcggc gcgcctgtgt tttgaccgtc aggaaagtct ttttttccc   3600 tgaatagtca agggtctata cttcttgaag caattgggac actaatcaat tattgtttat   3660
acctcggacc atcttttcct tcttcacacc actaatcagt ttatgccttg gaccattaat   3720
tgtgttgttc acaagcttct tgtttatggt ttacaaagca ttcgcctaga tttgtgtgtg   3780
tctctacaca tcgatcactt ttaaatactt gtcgctttca gttattcttt taacgtttgg   3840
ttatttatct tatttaaaaa aattatcgta ttattattta ttttgtttgt gatttacttt   3900
attatcaaaa gtatttcaaa tatgacttat ctttttttat aagtgcacta atttttcaaa   3960
taagatgaat ggtcaaatgt tacaagaaaa agttaaagca accactaatt tagggcggag   4020
gtagtaaaac ctagttattg taaccaataa ttttatcaat ctataaatgc aacacaaagt   4080
cacttcgtga tatctcacac aaagccactt caacgatgaa agctgactgc atgttttatc   4140
aaaacacatg tgatcagttt gttggatgaa aaaattatc tatgtcataa atcaagagtt   4200
ataatataag cttctggctc tacaagtaac atttctatgt ttttttttta cgttcttaca   4260
tactatgttt tgccaaaaaa aacatgatca tttttgttgga cgaaaagaaa tagtaaatat   4320
agagtgacct ttgatatcat tataatataa gcttctgcct ctataaataa catctatgca   4380
```

```
ctttttacgt cgtagtaatt tgatatatga gaaatttaca tataacattt ttgtgcagca   4440
taaccac                                                            4447

<210> SEQ ID NO 14
<211> LENGTH: 385
<212> TYPE: PRT
<213> ORGANISM: Arabidopsis thaliana

<400> SEQUENCE: 14

Met Asp Met Lys Ser Gly His Ser Ser Pro Val Met Thr Asp Ser Pro
1               5                   10                  15

Pro Ile Ser Asn Ser Arg Leu Thr Ile Arg Gln Asn Arg Leu Pro Tyr
            20                  25                  30

Ser Ser Ala Ala Ala Thr Ala Ile Ser Gln Asn Asn Asn Leu Leu Leu
        35                  40                  45

Thr Val Pro Arg Lys Lys Thr Gly Ile Leu Asp Asp Val Lys Ser Asn
    50                  55                  60

Gly Trp Leu Asp Ala Met Lys Ser Ser Pro Pro Thr Ile Leu
65                  70                  75                  80

Asn Lys Asp Asn Leu Ser Asn Asp Ala Thr Asp Met Thr Tyr Arg Glu
                85                  90                  95

Trp Met Gln Leu Lys Tyr Pro Ser Ala Leu Thr Ser Phe Glu Lys Ile
            100                 105                 110

Met Ser Phe Ala Lys Gly Lys Arg Ile Ala Leu Phe Leu Asp Tyr Asp
        115                 120                 125

Gly Thr Leu Ser Pro Ile Val Glu Glu Pro Asp Cys Ala Tyr Met Ser
    130                 135                 140

Ser Ala Met Arg Ser Ala Val Gln Asn Val Ala Lys Tyr Phe Pro Thr
145                 150                 155                 160

Ala Ile Ile Ser Gly Arg Ser Arg Asp Lys Val Tyr Glu Phe Val Asn
                165                 170                 175

Leu Ser Glu Leu Tyr Tyr Ala Gly Ser His Gly Met Asp Ile Met Ser
            180                 185                 190

Pro Ala Gly Glu Ser Leu Asn His Glu His Ser Arg Thr Val Ser Val
        195                 200                 205

Tyr Glu Gln Gly Lys Asp Val Asn Leu Phe Gln Pro Ala Ser Glu Phe
    210                 215                 220

Leu Pro Met Ile Asp Lys Val Leu Cys Ser Leu Ile Glu Ser Thr Lys
225                 230                 235                 240

Asp Ile Lys Gly Val Lys Val Glu Asp Asn Lys Phe Cys Ile Ser Val
                245                 250                 255

His Tyr Arg Asn Val Glu Glu Lys Asn Trp Thr Leu Val Ala Gln Cys
            260                 265                 270

Val Asp Asp Val Ile Arg Thr Tyr Pro Lys Leu Arg Leu Thr His Gly
        275                 280                 285

Arg Lys Val Leu Glu Ile Arg Pro Val Ile Asp Trp Asp Lys Gly Lys
    290                 295                 300

Ala Val Thr Phe Leu Leu Glu Ser Leu Gly Leu Asn Asn Cys Glu Asp
305                 310                 315                 320

Val Leu Pro Ile Tyr Val Gly Asp Asp Arg Thr Asp Glu Asp Ala Phe
                325                 330                 335

Lys Val Leu Arg Asp Gly Pro Asn His Gly Tyr Gly Ile Leu Val Ser
            340                 345                 350
```

```
Ala Val Pro Lys Asp Ser Asn Ala Phe Tyr Ser Leu Arg Asp Pro Ser
            355                 360                 365

Glu Val Met Glu Phe Leu Lys Ser Leu Val Thr Trp Lys Arg Ser Met
    370                 375                 380

Gly
385

<210> SEQ ID NO 15
<211> LENGTH: 374
<212> TYPE: PRT
<213> ORGANISM: Arabidopsis thaliana

<400> SEQUENCE: 15

Met Thr Asn Gln Asn Val Ile Val Ser Asp Arg Lys Pro Ile Leu Gly
1               5                   10                  15

Leu Lys Thr Ile Thr Val Ser Val Ser Asn Ser Pro Leu Phe Ser Asn
                20                  25                  30

Ser Phe Pro Thr Tyr Phe Asn Phe Pro Arg Arg Lys Leu Leu Lys Leu
            35                  40                  45

Leu Glu Ala Ala Asp Lys Asn Asn Leu Val Val Ala Pro Lys Ile Thr
    50                  55                  60

Ser Met Ile Asp Ser Met Arg Asp Ser Ser Pro Thr Arg Leu Arg Ser
65                  70                  75                  80

Ser Ser Tyr Asp Ser Asp Ser Asn Asp Asp Lys Thr Ser Trp Ile
                85                  90                  95

Val Arg Phe Pro Ser Ala Leu Asn Met Phe Asp Glu Ile Val Asn Ala
            100                 105                 110

Ala Lys Gly Lys Gln Ile Val Met Phe Leu Asp Tyr Asp Gly Thr Leu
    115                 120                 125

Ser Pro Ile Val Glu Asp Pro Asp Lys Ala Phe Ile Thr His Glu Met
130                 135                 140

Arg Glu Val Val Lys Asp Val Ala Ser Asn Phe Pro Thr Ala Ile Val
145                 150                 155                 160

Thr Gly Arg Ser Ile Glu Lys Val Arg Ser Phe Val Gln Val Asn Glu
                165                 170                 175

Ile Tyr Tyr Ala Gly Ser His Gly Met Asp Ile Glu Gly Pro Thr Asn
            180                 185                 190

Glu Asn Ser Asn Gly Gln Ser Asn Glu Arg Val Leu Phe Gln Pro Ala
    195                 200                 205

Arg Glu Phe Leu Pro Met Ile Glu Lys Val Val Asn Ile Leu Glu Glu
210                 215                 220

Lys Thr Lys Trp Ile Pro Gly Ala Met Val Glu Asn Asn Lys Phe Cys
225                 230                 235                 240

Leu Ser Val His Phe Arg Arg Val Asp Glu Lys Arg Trp Pro Ala Leu
                245                 250                 255

Ala Glu Val Val Lys Ser Val Leu Ile Asp Tyr Pro Lys Leu Lys Leu
            260                 265                 270

Thr Gln Gly Arg Lys Val Leu Glu Ile Arg Pro Thr Ile Lys Trp Asp
    275                 280                 285

Lys Gly Gln Ala Leu Asn Phe Leu Leu Lys Ser Leu Gly Tyr Glu Asn
290                 295                 300

Ser Asp Asp Val Val Pro Val Tyr Ile Gly Asp Asp Arg Thr Asp Glu
305                 310                 315                 320

Asp Ala Phe Lys Val Leu Arg Glu Arg Gly Gln Gly Phe Gly Ile Leu
                325                 330                 335
```

```
Val Ser Lys Val Pro Lys Asp Thr Asn Ala Ser Tyr Ser Leu Gln Asp
            340                 345                 350

Pro Ser Gln Val Asn Lys Phe Leu Glu Arg Leu Val Glu Trp Lys Arg
        355                 360                 365

Lys Thr Val Gly Glu Glu
    370

<210> SEQ ID NO 16
<211> LENGTH: 382
<212> TYPE: PRT
<213> ORGANISM: Oryza sativa

<400> SEQUENCE: 16

Met Asp Leu Lys Thr Ser Asn Ser Pro Val Ile Ala Asp Pro Leu Pro
1               5                   10                  15

Lys Leu Ala Leu Pro Ser Ala Val Met Thr Tyr Thr Thr Pro Thr Ser
            20                  25                  30

Phe Pro Ser Thr Gly Leu Tyr Leu Asn Thr Pro Lys Lys Lys Pro Leu
        35                  40                  45

Pro Gly Lys Ile Glu Glu Val Arg Ala Ala Gly Trp Leu Asp Leu Met
    50                  55                  60

Leu Ala Ser Ser Pro Pro Arg Lys Arg Gln Thr Lys Asp Phe Ala Asn
65                  70                  75                  80

Asp Val Gln Ala Asp Glu Leu Asp Leu Leu Tyr Arg Asn Trp Val Val
                85                  90                  95

Asn His Pro Ser Ala Leu Thr Ser Phe Glu Asp Ile Val Asn Leu Ala
            100                 105                 110

Arg Gly Lys Arg Leu Ala Leu Phe Leu Asp Tyr Asp Gly Thr Leu Ser
        115                 120                 125

Pro Ile Val Asp Asn Pro Glu Asn Ala Val Met Ser Asp Glu Met Arg
    130                 135                 140

Ser Ala Val Lys His Val Ala Ser Leu Phe Pro Thr Ala Ile Ile Ser
145                 150                 155                 160

Gly Arg Ser Arg Asp Lys Val Phe Asp Phe Val Lys Leu Thr Glu Leu
                165                 170                 175

Tyr Tyr Ala Gly Ser His Gly Met Asp Ile Met Gly Pro Val Arg Lys
            180                 185                 190

Ser Asp Ser Ser Gly Gln His Val Glu Cys Ile Arg Ser Thr Asp Ser
        195                 200                 205

Glu Gly Lys Glu Val Asn Leu Phe Gln Pro Ala Ser Glu Phe Leu Pro
    210                 215                 220

Met Ile Ser Glu Val Tyr Lys Lys Leu Ser Glu Ser Ile Lys Asp Ile
225                 230                 235                 240

Glu Val Arg Pro Val Ile Asp Trp Asn Lys Gly Lys Ala Val Glu Phe
                245                 250                 255

Leu Leu Glu Ser Leu Gly Leu Cys Gly Lys Glu Asp Val Leu Pro Ile
            260                 265                 270

Tyr Val Gly Asp Asp Lys Thr Asp Glu Asp Ala Phe Lys Val Leu Lys
        275                 280                 285

Ala Asn Asp Gly Ala Arg Met Glu Asp Asn Lys Phe Cys Val Ser Val
    290                 295                 300

His Tyr Arg Asn Val Ala Pro His Asp Tyr Gly Glu Val His Gln Arg
305                 310                 315                 320
```

```
Val Thr Ala Val Leu Lys Asn Tyr Pro Cys Leu Arg Leu Thr His Gly
            325                 330                 335

Arg Lys Val Leu Ser Ile Gly Phe Gly Ile Leu Val Ser Ser Val Pro
            340                 345                 350

Lys Asp Thr Asp Ala Phe Tyr Ser Val Arg Asp Pro Ala Glu Val Met
            355                 360                 365

Glu Phe Leu Lys Lys Leu Ala Ser Trp Lys Glu Glu Ser Thr
            370                 375                 380

<210> SEQ ID NO 17
<211> LENGTH: 229
<212> TYPE: PRT
<213> ORGANISM: Thermoplasma acidophilum

<400> SEQUENCE: 17

Met Ile Phe Leu Asp Tyr Asp Gly Thr Leu Val Pro Ile Ile Met Asn
1               5                   10                  15

Pro Glu Ser Tyr Ala Asp Ala Gly Leu Leu Ser Leu Ile Ser Asp
            20                  25                  30

Leu Lys Glu Arg Phe Asp Thr Tyr Ile Val Thr Gly Arg Ser Pro Glu
            35                  40                  45

Glu Ile Ser Arg Phe Leu Pro Leu Asp Ile Asn Met Ile Cys Tyr His
    50                  55                  60

Gly Ala Cys Ser Lys Ile Asn Gly Gln Ile Val Tyr Asn Asn Gly Ser
65                  70                  75                  80

Asp Arg Phe Leu Gly Val Phe Asp Arg Ile Tyr Glu Asp Thr Arg Ser
                85                  90                  95

Trp Val Ser Asp Phe Pro Gly Leu Arg Ile Tyr Arg Lys Asn Leu Ala
            100                 105                 110

Val Leu Tyr His Leu Gly Leu Met Gly Ala Asp Met Lys Pro Lys Leu
            115                 120                 125

Arg Ser Arg Ile Glu Glu Ile Ala Arg Ile Phe Gly Val Glu Thr Tyr
            130                 135                 140

Tyr Gly Lys Met Ile Ile Glu Leu Arg Val Pro Gly Val Asn Lys Gly
145                 150                 155                 160

Ser Ala Ile Arg Ser Val Arg Gly Glu Arg Pro Ala Ile Ile Ala Gly
                165                 170                 175

Asp Asp Ala Thr Asp Glu Ala Ala Phe Glu Ala Asn Asp Ala Leu
            180                 185                 190

Thr Ile Lys Val Gly Glu Gly Glu Thr His Ala Lys Phe His Val Ala
            195                 200                 205

Asp Tyr Ile Glu Met Arg Lys Leu Lys Phe Ile Glu Met Leu Gly
            210                 215                 220

Val Gln Lys Lys Gln
225

<210> SEQ ID NO 18
<211> LENGTH: 10
<212> TYPE: PRT
<213> ORGANISM: Artificial Sequence
<220> FEATURE:
<223> OTHER INFORMATION: B-phosphatase box consensus sequence

<400> SEQUENCE: 18

Asp Tyr Asp Gly Thr Leu Ser Pro Ile Val
1               5                   10
```

```
<210> SEQ ID NO 19
<211> LENGTH: 10
<212> TYPE: PRT
<213> ORGANISM: Artificial Sequence
<220> FEATURE:
<223> OTHER INFORMATION: Modified B-phosphatase box

<400> SEQUENCE: 19

Asp Tyr Asp Gly Thr Leu Ser Pro Phe Val
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Consensus sequence

<400> SEQUENCE: 20

Cys Val Ser Val His Phe Arg Cys Val
1               5

<210> SEQ ID NO 21
<211> LENGTH: 9
<212> TYPE: PRT
<213> ORGANISM: Artificial Sequence
<220> FEATURE:
<223> OTHER INFORMATION: Modified consensus sequence

<400> SEQUENCE: 21

Cys Val Ser Val Asp Phe Arg Cys Val
1               5
```

METHODS OF INCREASING YIELD AND STRESS TOLERANCE IN A PLANT BY DECREASING THE ACTIVITY OF A TREHALOSE-6-PHOSPHATE PHOSPHATASE

RELATED APPLICATION INFORMATION

This application is a 371 of International Application No. PCT/US2012/046888, filed 16 Jul. 2012, which claims priority to U.S. Provisional Patent Application No. 61/508,609, filed 15 Jul. 2011, and U.S. Provisional Patent Application No. 61/522,588, filed 11 Aug. 2011, the contents of which are incorporated herein by reference herein.

STATEMENT REGUARDING ELECTRONIC SUBMISSION OF A SEQUENCE LISTING

A Sequence Listing in ASCII text format, submitted under 37 C.F.R. §1.821, entitled 73248-US-REG-ORG-P-1 1Jul. 2014 CORRECTEDSEQUENCE LIST ST25, 42 KB in size, generated on Jun. 1, 2014 and filed via EFS-Web is provided in lieu of a paper copy. This Sequence Listing is hereby incorporated by reference into the specification for its disclosure.

FIELD OF THE INVENTION

The present invention relates generally to the field of molecular biology and regards various polynucleotides, polypeptides and methods of use that may be employed to enhance yield in transgenic plants. Specifically the transgenic plants with modified polypeptides resulting in decreased activity of trehalose-6-phosphate phosphatase may exhibit any one of the traits consisting of increased yield, increased tolerance to abiotic stress, increased cell growth, increased nutrient use efficiency.

BACKGROUND OF THE INVENTION

The increasing world population and the dwindling supply of arable land available for agriculture fuels the need for research in the area of increasing the efficiency of agriculture. Conventional means for crop and horticultural improvements utilize selective breeding techniques to identify plants having desirable characteristics. However, such selective breeding techniques have several drawbacks, namely that these techniques are often labor intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant's genome. Such technology has the capacity to deliver crops or plants having various improved economic, agronomic or horticultural traits.

SUMMARY OF THE INVENTION

The following Summary lists several embodiments of the invention subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the invention, whether listed in this Summary or not. To avoid excessive repetition, this Summary does not list or suggest all possible combinations of such features.

The invention provides nucleotide sequences encoding polypeptides of the trehalose pathway that when transgenically expressed in a plant increase yield. The T6PP polypeptides described herein comprise modifications which alter the activity of the trehalose-6-phosphate phosphatase (T6PP) proteins wherein the activity is decreased as compared to an unmodified T6PP. The modified T6PPs may comprise the consensus sequence exemplified in SEQ ID NO: 9 and have at least one modified amino acid. The modified T6PP may have a modification made in a conserved amino acid including the conserved amino acids described in the consensus sequence SEQ ID NO: 9. The modified T6PPs may cause the in vitro activation of a wild type T6PP. The modification to T6PP may be within at least one of the CAP, phosphatase, A-phosphatase or B-phosphatase domains. T6PPs having decreased substrate binding to trehalose-6-phosphate (T6P) show increased yield and increased stress tolerance when expressed transgenically in plants as well as having increased tolerance to stress, including drought. The plants expressing a modified T6PP include monocot or dicot plants, including plants selected from the group consisting of maize, sugarcane, soybean, rice, sorghum or wheat. The modifications to T6PP polypeptides may include one or a combination of amino acid substitutions, amino acid deletions or amino acid additions. The modified T6PPs may be a member of the of the haloacid dehalogenase (HAD) superfamily of phosphatases. The enzymatic activity of T6PP may be reduced by at least 50%, 60%, 70%, 80%, 90%, 95%, 99% or 100%.

Any of the described T6PP polypeptides can be used to produce polynucleotides. The polynucleotides encoding modified T6PP polypeptides may be introduced into a host cell. The host cell may include a plant cell. The polynucleotides may be included in expression cassettes that ensure transcription of the polynucleotide in a plant. The expression cassettes may include a promoter that expresses the polynucleotide in plant reproductive tissue. In addition, the reproductive tissue may be selected from the group consisting of spikelet tissue, ear node, bract tissue, spikelet meristem tissue, inflorescence stalk tissue, and immature floral tissue. The promoter expressing the T6PP polynucleotides may include an OsMADS promoter or an OsMADS6 promoter. An extract comprising the polynucleotides or polypeptides can be made from any of the host cells, plants, plant parts or plant tissues.

The methods disclosed herein further introducing of plants with the polynucleotides for example as disclosed herein. Transgenic plants comprising the polynucleotides disclosed herein may display increased cell growth, increased plant and/or seedling vigor, increased yield, increased seed weight, increased water use efficiency and/or increased biomass. Plants produced by the methods herein are contemplated to have an increased tolerance to abiotic stress. The transgenic plants described herein may produce higher yield in both biomass yield and grain yield of the plant. One aspect of the invention provides various modifications one may perform on any given T6PP gene sequence that may be employed in transgenic plants to confer increased yield. Alternatively, multiple other methods may be employed to increase the levels of T6P to confer increased yield and stress tolerance in a plant.

The methods for increasing yield, increasing tolerance of a plant to abiotic stress or reducing barrenness in a plant, increasing ears per plant and/or kernels per plant under water deficit conditions may include introducing an expression cassette comprising a modified T6PP into a plant cell and then producing a transgenic plant. The plant may be a monocot plant, for example, may be a maize, rice, wheat, sorghum, sugarcane or lawn grass plant. The may be a dicot plant, such as, soybean. For methods of increasing tolerance of a plant to abiotic stress, the stress may be selected from the group consisting of water stress, heat stress or cold stress. The water stress may be caused by drought.

In addition, included are methods of modifying the level of trehalose-6-phosphate in a plant by identifying a polypeptide in the trehalose pathway; modifying the polypeptide to have altered enzymatic activity; introducing an expression cassette comprising a polynucleotide encoding the modified polypeptide in a plant; and producing a plant with modified levels of trehalose-6-phosphate. The polypeptide may have an activity selected from the group consisting of trehalose-6-phosphate synthase; trehalose-6-phosphate phosphatase and trehalase. The modified levels of trehalose-6-phosphate may result in an increase in the expression of genes in the pentose phosphate shunt pathway during drought stress in the ear node tissue of a plant. In addition or alternatively, the modified levels of trehalose-6-phosphate may cause an increase in the level of carbonic anhydrase in the ear node tissue of a plant. The modified polypeptide may be expressed in plant reproductive tissues, including, spikelet tissue, ear node, bract tissue, spikelet meristem tissue, inflorescence stalk tissue, and immature floral tissue. The modified polypeptide modified trehalose pathway enzyme may have reduced enzymatic activity and/or cause the in vitro activation of a wild type trehalose-6-phosphate phosphatase.

These and other features, objects and advantages of the present invention will become better understood from the description that follows. In the description, reference is made to the accompanying sequences, which form a part hereof and in which there is shown by way of illustration, not limitation, embodiments of the invention. The description of preferred embodiments is not intended to limit the invention to cover all modifications, equivalents and alternatives. Reference should therefore be made to the embodiments recited herein for interpreting the scope of the invention.

BRIEF DESCRIPTION OF THE SEQUENCES IN THE SEQUENCE LISTING nt=nucleotide sequence
pt=protein sequence
SEQ ID NO: 1 Trehalose-6-Phosphate Phosphatase (nt)
SEQ ID NO: 2 Trehalose-6-Phosphate Phosphatase (pt)
SEQ ID NO: 3 Trehalose-6-Phosphate Phosphatase—single modification (nt)
SEQ ID NO: 4 Trehalose-6-Phosphate Phosphatase—single modification (pt)
SEQ ID NO: 5 Trehalose-6-Phosphate Phosphatase—double modification a (nt)
SEQ ID NO: 6 Trehalose-6-Phosphate Phosphatase—double modification a (pt)
SEQ ID NO: 7 Trehalose-6-Phosphate Phosphatase Consensus Sequence
SEQ ID NO: 8 Trehalose-6-Phosphate Phosphatase PPase domain
SEQ ID NO: 9 Trehalose-6-Phosphate Phosphatase A-Phosphatase box
SEQ ID NO: 10 Trehalose-6-Phosphate Phosphatase B-Phosphatase box
SEQ ID NO: 11 OsMADS6 Promoter
SEQ ID NO: 12 Trehalose-6-Phosphate Phosphatase B-Phosphatase box
SEQ ID NO: 13 OsMADS6 Promoter
SEQ ID NO: 14 Trehalose-6-Phosphate Phosphatase *Arabidopsis thaliana* 19925
SEQ ID NO: 15 Trehalose-6-Phosphate Phosphatase *Arabidopsis thaliana* 19926
SEQ ID NO: 16 Trehalose-6-Phosphate Phosphatase *Oryza sativa* 19924
SEQ ID NO: 17 Trehalose-6-Phosphate Phosphatase like *Thermoplasma acidophilum* (Q9HIW7)
SEQ ID NO: 18 B-Phosphatase box consensus
SEQ ID NO: 19 Modified B-Phosphatase box consensus
SEQ ID NO: 20 Consensus sequence
SEQ ID NO: 21 Modified consensus sequence

DESCRIPTION OF FIGURES

FIGS. 1A to 1C show the initial alignment of T6PP sequences from *Arabidopsis thaliana* (19925; SEQ ID NO: 14), *Arabidopsis thaliana* (19926; SEQ ID NO: 15), *Oryza sativa* (19924; SEQ ID NO: 16), *Oryza sativa* (15777; wild type OsT6PP-WT; SEQ ID NO: 2) and *Thermoplasma acidophilum* (Q9HIW7; SEQ ID NO: 17). The sequences were aligned with Vector NTI using the ClustalW method.

FIG. 10 shows the consensus sequence for T6PP (SEQ ID NO: 9). The residues in bold and underlined identify the highly conserved regions. The "X" marked positions in the consensus sequence indicates regions of variability wherein any other single letter refers to the common single letter amino acid notation commonly used in the art. The underlined amino acid residues indicate regions that may be modified to construct T6PP polypeptides that confer increased yield and/or increased stress resistance in a transgenic plant. The residues identified by DYDGTLSPIV encode a B-phosphatase box.

FIGS. 11A to 11C show the final alignment of the T6PP sequences for *Arabidopsis thaliana* (19925; SEQ ID NO: 14), *Arabidopsis thaliana* (19926; SEQ ID NO: 15), *Oryza sativa* (19924; SEQ ID NO: 16), and *Oryza sativa* (15777; wild type OsT6PP-WT; SEQ ID NO: 2) and the T6PP-related protein from *Thermoplasma acidophilum* (Q9HIW7; SEQ ID NO: 17).

DETAILED DESCRIPTION

Figure 2:
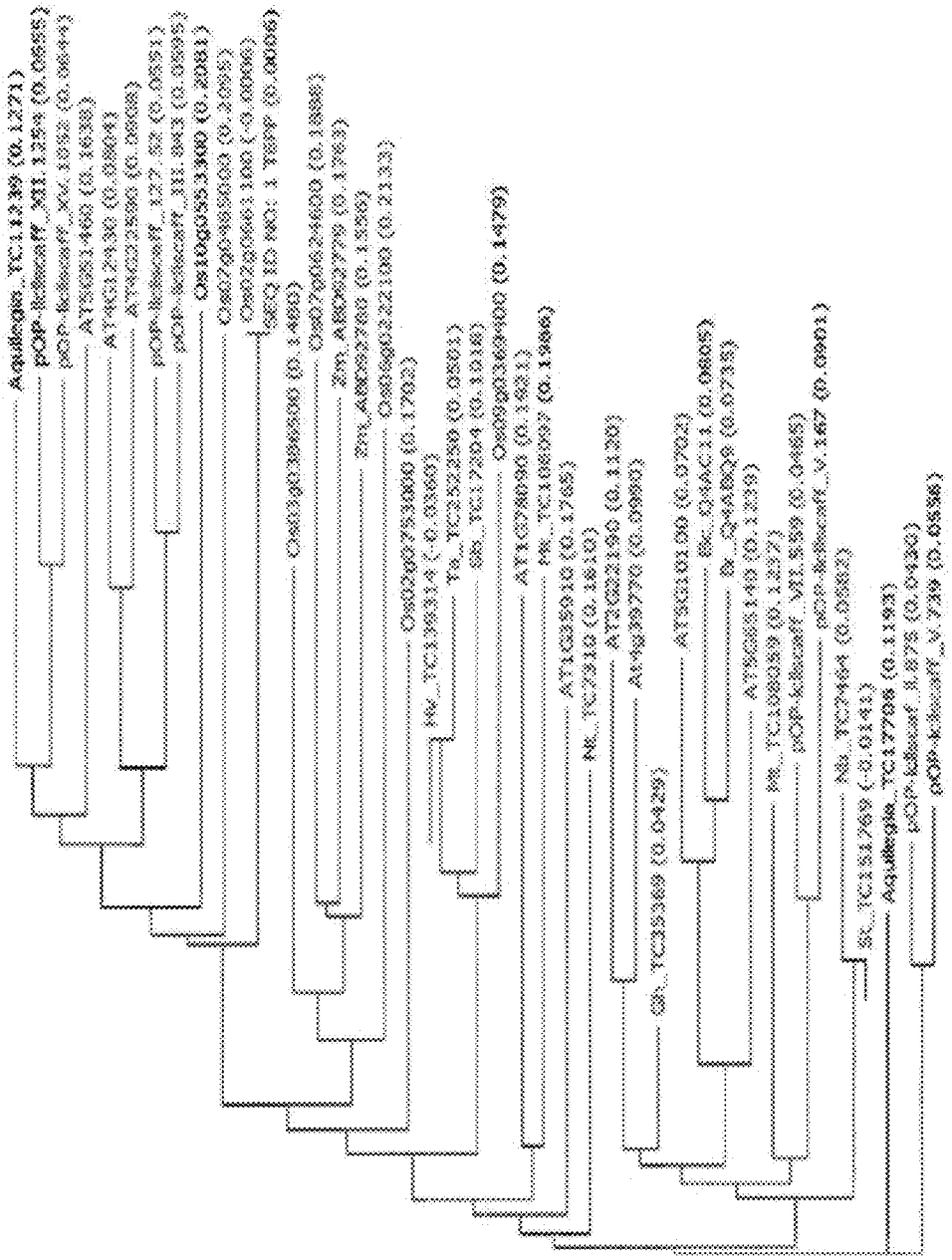
FIG. 2 shows a phylogenic tree derived from the alignment of multiple T6PP proteins.

The practice of the present invention will employ, unless otherwise indicated, conventional techniques of botany, microbiology, tissue culture, molecular biology, chemistry, biochemistry, plant quantitative genetics, statistics and recombinant DNA technology, which are within the skill of the art. Such techniques are explained fully in the literature. See, e.g., Langenheim and Thimann, (1982) Botany: Plant Biology and Its Relation to Human Affairs, John Wiley; Cell Culture and Somatic Cell Genetics of Plants, vol. 1, Vasil, ed. (1984); Stanier, et al., (1986) The Microbial World, 5th ed., Prentice-Hall; Dhringra and Sinclair, (1985) Basic Plant Pathology Methods, CRC Press; Maniatis, et al., (1982) Molecular Cloning: A Laboratory Manual; DNA Cloning, vols. I and II, Glover, ed. (1985); Oligonucleotide Synthesis, Gait, ed. (1984); Nucleic Acid Hybridization, Hames and Higgins, eds. (1984); and the series Methods in Enzymology, Colowick and Kaplan, eds, Academic Press, Inc., San Diego, Calif.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

Unless otherwise defined, all technical and scientific terms used herein have the same meaning as commonly understood by one of ordinary skill in the art to which this invention belongs.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention.

As used herein the singular forms "a", "and", and "the" include plural reference unless the context clearly dictates otherwise. Thus, for example, reference to "a vector" is a reference to one or more vectors and includes equivalents thereof known to those skilled in the art.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent.

As used herein, the word "or" means any one member of a particular list and also includes any combination of members on that list.

The terms "comprises", "comprising", "includes", "including", "having" and their conjugates mean "including but not limited to". The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between. As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS) and strand displacement amplification (SDA). See, e.g., Diagnostic Molecular Microbiology: Principles and Applications, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) J. Gen. Microbiol. 139:425-32) can be modified to yield a functionally identical molecule. Accordingly, each silent variation of a nucleic acid, which encodes a polypeptide of the present invention, is implicit in each described polypeptide sequence and incorporated herein by reference.

A "control plant" or "control" as used herein may be a non-transgenic plant of the parental line used to generate a transgenic plant herein. A control plant may in some cases be a transgenic plant line that includes an empty vector or marker gene, but does not contain the recombinant polynucleotide of the present invention that is expressed in the transgenic plant being evaluated. A control plant in other cases is a transgenic plant expressing the gene with a constitutive promoter. In general, a control plant is a plant of the same line or variety as the transgenic plant being tested, lacking the specific trait-conferring, recombinant DNA that characterizes the transgenic plant. Such a progenitor plant that lacks that specific trait-conferring recombinant DNA can be a natural, wild-type plant, an elite, non-transgenic plant, or a transgenic plant without the specific trait-conferring, recombinant DNA that characterizes the transgenic plant. The progenitor plant lacking the specific, trait-conferring recombinant DNA can be a sibling of a transgenic plant having the specific, trait-conferring recombinant DNA. Such a progenitor sibling plant may include other recombinant DNA As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity or ligand/receptor binding is generally at least 30%, 40%, 50%, 60%, 70%, 80% or 90%, preferably 60-90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V) and
6) Phenylalanine (F), Tyrosine (Y), Tryptophan (W).
7) See also, Creighton, Proteins, W.H. Freeman and Co. (1984).

As used herein the terms "modified" or "modification" interchangeably refer to deliberate or random substitutions, deletions or additions to a nucleic acid, peptide, polypeptide or protein sequence which alters, adds or deletes at least one amino acid residue within a given polypeptide. A "modified T6PP" as used herein refers to any nucleic acid encoding a T6PP or peptides, polypeptides or protein having T6PP activity either of which having been modified so that the resultant T6PP confers modifies T6PP activity and/or modified binding to T6P resulting in improved yield and/or abiotic stress tolerance in a plant when compared with an unmodified T6PP.

As used herein "homologous position" refers to the position of one or more amino acids in a polypeptide or one or more base pairs in a polynucleotide sequence that are in a similar or equivalent position in a second polypeptide or polynucleotide that is an ortholog, paralog or homolog to the original sequence. The position of the amino acids may be in the same functional region of the two proteins but may not be at the exact numeric position of the amino acid between the two polypeptide sequences. The homologous position of amino acids on two proteins can be determined by several methods well known in the art including, for example, sequence alignment (e.g. Basic Local Alignment Search Tool (BLAST®), three dimensional protein modeling (see for example, Sander C. and Scheider R., (1991) PROTEINS: Structure, Function and Genetics 9:56-68) and the like.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capricolumn* (Yamao, et al., (1985) Proc. Natl. Acad. Sci. USA 82:2306-9) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, by any means, such as, "transfection", "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, as part of a mini-chromosome or transiently expressed (e.g., transfected mRNA).

As used herein "gene stack" refers to the introduction of two or more genes into the genome of an organism. In certain aspects of the invention it may be desirable to stack any abiotic stress gene (e.g. cold shock proteins, genes associated with ABA response) with the T6PPs as described herein. Likewise, it may also be desirable to stack the genes of the trehalose pathway as described herein with genes conferring insect resistance, disease resistance, increased yield or any other beneficial trait (e.g. increased plant height, etc) known in the art. Alternatively, transgenic plants comprising a modified trehalose pathway gene may be stacked with native trait alleles that confer additional traits, such as, improved water use, increased disease resistance and the like. In one embodiment, plants expressing modified trehalose pathway genes are stacked with the alleles described in WO2011/079277. Traits may be stacked by introducing expression cassettes with multiple genes or breeding/crossing plants with one or more traits with other plants containing one or more additional traits.

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "NUE nucleic acid" means a nucleic acid comprising a polynucleotide ("NUE polynucleotide") encoding a full length or partial length NUE polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise in one case a substantial representation of the entire transcribed fraction of a genome of a specified organism. Construction of exemplary nucleic acid libraries, such as genomic and cDNA libraries, is taught in standard molecular biology references such as Berger and Kimmel, (1987) Guide To Molecular Cloning Techniques, from the series Methods in Enzymology, vol. 152, Academic Press, Inc., San Diego, Calif.; Sambrook, et al., (1989) Molecular Cloning: A Laboratory Manual, 2nd ed., vols. 1-3; and Current Protocols in Molecular Biology, Ausubel, et al., eds, Current Protocols, a joint venture between Greene Publishing Associates, Inc. and John Wiley & Sons, Inc. (1994 Supplement). In another instance "nucleic acid library" as defined herein may also be understood to represent libraries comprising a prescribed faction or rather not substantially representing an entire genome of a specified organism. For example, small RNAs, mRNAs and methylated DNA. A nucleic acid library as defined herein might also encompass variants of a particular molecule (e.g. a collection of variants for a particular protein).

As used herein "operably linked" includes reference to a functional linkage between a first sequence, such as a promoter and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis,*

*Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

As used herein, "yield" may include reference to bushels per acre of a grain crop at harvest, as adjusted for grain moisture (15% typically for maize, for example), and the volume of biomass generated (for forage crops such as alfalfa and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated. Yield can be affected by many properties including without limitation, plant height, pod number, pod position on the plant, number of internodes, incidence of pod shatter, grain size, efficiency of nodulation and nitrogen fixation, efficiency of nutrient assimilation, carbon assimilation, plant architecture, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill. Yield of a plant of the can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Moreover a bushel of corn is defined by law in the State of Iowa as 56 pounds by weight, a useful conversion factor for corn yield is: 100 bushels per acre is equivalent to 6.272 metric tons per hectare. Other measurements for yield are common practice in the art. In certain embodiments of the invention yield may be increased in stressed and/or non-stressed conditions.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions in most cells.

Any suitable promoter sequence can be used by the nucleic acid construct of the present invention. According to some embodiments of the invention, the promoter is a constitutive promoter, a tissue-specific, or an abiotic stress-inducible promoter.

Suitable constitutive promoters include, for example, CaMV 35S promoter (SEQ ID NO:1546; Odell et al., Nature 313:810-812, 1985); *Arabidopsis* At6669 promoter (SEQ ID NO:1652; see PCT Publication No. WO04081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol. Biol. 25(5):837-43, 1994); Maize H3 histone (Lepetit et al., Mol. Gen. Genet. 231: 276-285, 1992); Actin 2 (An et al., Plant J. 10(1); 107-121, 1996), constitutive root tip CT2 promoter (SEQ ID NO:1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608, 149; 5,608,144; 5,604,121; 5,569,597: 5,466,785; 5,399, 680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al., Plant Mol Biol, 143). 323-32 1990), napA (Stalberg, et al., Planta 199: 515-519, 1996), Wheat SPA (Albanietal, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet. 216:81-90, 1989; NAR 17:461-2), wheat a, b and g gliadins (EMBO3:1409-15, 1984), Barley 1trl promoter, barley B1, C, D hordein (Theor Appl Gen 98:1253-62, 1999; Plant J 4:343-55, 1993; Mol Gen Genet. 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (Plant Mol. Biol. 32:1029-35, 1996)], embryo specific promoters [e.g., rice OSH1 (Sato et al., Proc. Natl. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)], and flower-specific promoters [e.g., AtPRP4, chalene synthase (chsA) (Van der Meer, et al., Plant Mol. Biol. 15, 95-109, 1990), LAT52 (Twell et al., Mol. Gen. Genet. 217:240-245; 1989), apetala-3; plant reproductive tissues [e.g., OsMADS promoters (U.S. Patent Application 2007/0006344)].

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); heat-inducible promoters such as heat tomato hsp80-promoter from tomato (U.S. Pat. No. 5,187,267).

The term "Enzymatic activity" is meant to include demethylation, hydroxylation, epoxidation, N-oxidation, sulfooxidation, N-, S-, and O-dealkylations, desulfation, deamination, and reduction of azo, nitro, and N-oxide groups. The term "nucleic acid" refers to a deoxyribonucleotide or ribonucleotide polymer in either single- or double-stranded form, or sense or anti-sense, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

A "structural gene" is that portion of a gene comprising a DNA segment encoding a protein, polypeptide or a portion thereof, and excluding the 5' sequence which drives the initiation of transcription. The structural gene may alternatively encode a nontranslatable product. The structural gene may be one which is normally found in the cell or one which is not normally found in the cell or cellular location wherein it is introduced, in which case it is termed a "heterologous gene". A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications that could affect biological activity or its characteristics, the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bounded by the appropriate splice junctions. The structural gene may be translatable or non-translatable, including in an anti-sense orientation. The structural gene may be a composite of segments derived from a plurality of sources and from a plurality of gene sequences (naturally occurring or synthetic, where synthetic refers to DNA that is chemically synthesized).

"Derived from" is used to mean taken, obtained, received, traced, replicated or descended from a source (chemical and/or biological). A derivative may be produced by chemical or biological manipulation (including, but not limited to, substitution, addition, insertion, deletion, extraction, isolation, mutation and replication) of the original source.

"Chemically synthesized", as related to a sequence of DNA, means that portions of the component nucleotides were assembled in vitro. Manual chemical synthesis of DNA may be accomplished using well established procedures (Caruthers, *Methodology of DNA and RNA Sequencing*, (1983), Weissman (ed.), Praeger Publishers, New York, Chapter 1); automated chemical synthesis can be performed using one of a number of commercially available machines.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, an "expression cassette" is a nucleic acid construct, generated recombinantly or synthetically, with a series of specified nucleic acid elements, which permit transcription of a particular nucleic acid in a target cell. The expression cassette can be incorporated into a plasmid, chromosome, mitochondrial DNA, plastid DNA, virus or nucleic acid fragment. Typically, the expression cassette portion of an expression vector includes, among other sequences, a nucleic acid to be transcribed and a promoter.

The terms "residue" or "amino acid residue" or "amino acid" are used interchangeably herein to refer to an amino acid that is incorporated into a protein, polypeptide or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-84: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology-Hybridization with Nucleic Acid Probes*, part I, chapter 2, "Overview of principles of hybridization and the strategy of nucleic acid probe assays," Elsevier, New York (1993); and Current Protocols in Molecular Biology, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C. and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

"Overexpression" refers to the level of expression in transgenic organisms that exceeds levels of expression in normal or untransformed organisms.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

"Preferred expression", "Preferential transcription" or "preferred transcription" interchangeably refers to the expression of gene products that are preferably expressed at a higher level in one or a few plant tissues (spatial limitation) and/or to one or a few plant developmental stages (temporal limitation) while in other tissues/developmental stages there is a relatively low level of expression.

"Primary transformant" and "T0 generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

A "selectable marker gene" refers to a gene whose expression in a plant cell gives the cell a selective advantage. The selective advantage possessed by the cells transformed with the selectable marker gene may be due to their ability to grow in presence of a negative selective agent, such as an antibiotic or a herbicide, compared to the ability to grow of non-transformed cells. The selective advantage possessed by the transformed cells may also be due to their enhanced capacity, relative to non-transformed cells, to utilize an added compound as a nutrient, growth factor or energy source. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

The term "transformation" refers to the transfer of a nucleic acid fragment into the genome of a host cell, resulting in genetically stable inheritance. "Transiently transformed" refers to cells in which transgenes and foreign DNA have been introduced (for example, by such methods as Agrobacterium-mediated transformation or biolistic bombardment), but not selected for stable maintenance. "Stably transformed" refers to cells that have been selected and regenerated on a selection media following transformation.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The term "translational enhancer sequence" refers to that DNA sequence portion of a gene between the promoter and coding sequence that is transcribed into RNA and is present in the fully processed mRNA upstream (5') of the translation start codon. The translational enhancer sequence may affect processing of the primary transcript to mRNA, mRNA stability or translation efficiency. "Visible marker" refers to a gene whose expression does not confer an advantage to a transformed cell but can be made detectable or visible. Examples of visible markers include but are not limited to β-glucuronidase (GUS), luciferase (LUC) and green fluorescent protein (GFP).

"Wild-type" refers to the normal gene, virus, or organism found in nature without any mutation or modification.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

As used herein "Protein extract" refers to partial or total protein extracted from a plant part. Plant protein extraction methods are well known in the art.

As used herein "Plant sample" refers to either intact or non-intact (e g milled seed or plant tissue, chopped plant tissue, lyophilized tissue) plant tissue. It may also be an extract comprising intact or non-intact seed or plant tissue.

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, and 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, Basic Local Alignment Search Tool (BLAST®), FASTA and TFASTA in the Wisconsin Genetics Software Package, Version 8 (available from Genetics Computer Group (GCG®) programs (Accelrys, Inc., San Diego, Calif.). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65 and PearUS 2014/0143908 A110 May 22, 2014 son, et al., (1994) *Meth. Mol. Biol.* 24:307-31. The preferred program to use for optimal global alignment of multiple sequences isPileUp (Feng and Doolittle, (1987) *J. Mol. Evol.,* 25:351-60 which is similar to the method described by Higgins and Sharp, (1989) *CABIOS* 5:151-53 and hereby incorporated by reference). The Basic Local Alignment Search Tool (BLAST®) family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40 and 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs (Basic Local Alignment Search Tool, Blast®) using default parameters (Altschul, et al., (1997) *Nucleic Acids Res.* 25:3389-402).

As those of ordinary skill in the art will understand, Basic Local Alignment Search Tool (BLAST®) searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity-alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The phrase "abiotic stress" as used herein refers to any adverse effect on metabolism, growth, reproduction and/or viability of a plant by abiotic factors (i.e. water availability, heat, cold, and etc). Accordingly, abiotic stress can be induced by suboptimal environmental growth conditions such as, for example, salinity, water deprivation, water deficit, drought, flooding, freezing, low or high temperature (e.g., chilling or excessive heat), toxic chemical pollution, heavy metal toxicity, anaerobiosis, nutrient deficiency, nutrient excess, atmospheric pollution or UV irradiation.

The phrase "abiotic stress tolerance" as used herein refers to the ability of a plant to endure an abiotic stress without suffering a substantial alteration in metabolism, growth, productivity and/or viability.

As used herein "water deficit" means a period when water available to a plant is not replenished at the rate at which it is consumed by the plant. A long period of water deficit is colloquially called drought. Lack of rain or irrigation may not produce immediate water stress if there is an available reservoir of ground water to support the growth rate of plants. Plants grown in soil with ample groundwater can survive days without rain or irrigation without adverse affects on yield. Plants grown in dry soil are likely to suffer adverse affects with minimal periods of water deficit. Severe water deficit stress can cause wilt and plant death; moderate drought can reduce yield, stunt growth or retard development. Plants can recover from some periods of water deficit stress without significantly affecting yield. However, water deficit at the time of pollination can lower or reduce yield. Thus, a useful period in the life cycle of corn, for example, for observing response or tolerance to water deficit is the late vegetative stage of growth before tassel emergence or the transition to reproductive development. Tolerance to water deficit is determined by comparison to control plants. For instance, plants of this invention can produce a higher yield than control plants when exposed to water deficit. In the laboratory and in field trials drought can be simulated by giving plants of this invention and control plants less water than is given to sufficiently-watered control plants and measuring differences in traits. For example, yield can be broken out into components such as, plants per acre, kernel row number per ear, ears per plant, kernels per plant and weight per kernel. Barrenness or reduced seed set can also increase under water stress. One aspect of the invention provides plants overexpressing the genes as disclosed herein which confers a higher tolerance to a water deficit.

As used herein, the phrase "water optimization" refers to any measure of a plant, its parts, or its structure that can be measured and/or quantified in order to assess an extent of or a rate of plant growth and development under different conditions of water availability. As such, a "water optimization trait" is any trait that can be shown to influence yield in a plant under different sets of growth conditions related to water availability. Exemplary measures of water optimization are grain yield at standard moisture percentage (YGSMN), grain moisture at harvest (GMSTP), grain weight per plot (GWTPN), and percent yield recovery (PYREC).

As used herein, the phrases "drought tolerance" and "drought tolerant" refer to a plant's ability to endure and/or thrive under conditions where water availability is suboptimal. In general, a plant is labeled as "drought tolerant" if it displays "enhanced drought tolerance." As used herein, the phrase "enhanced drought tolerance" refers to a measurable improvement, enhancement, or increase in one or more water optimization phenotypes as compared to one or more control plants.

Water Use Efficiency (WUE) is a parameter frequently used to estimate the tradeoff between water consumption and $CO_2$ uptake/growth (Kramer, 1983, Water Relations of Plants, Academic Press p. 405). WUE has been defined and measured in multiple ways. One approach is to calculate the ratio of whole plant dry weight, to the weight of water consumed by the plant throughout its life (Chu et al., 1992, Oecologia 89:580). Another variation is to use a shorter time interval when biomass accumulation and water use are measured (Mian et al., 1998, Crop Sci. 38:390). Another approach is to utilize measurements from restricted parts of the plant, for example, measuring only aerial growth and water use (Nienhuis et al 1994 Amer J Bot 81:943). WUE also has been defined as the ratio of $CO_2$ uptake to water vapor loss from a leaf or portion of a leaf, often measured over a very short time period (e.g. seconds/minutes) (Kramer, 1983, p. 406). The ratio of $^{13}C/^{12}C$ fixed in plant tissue, and measured with an isotope ratio mass-spectrometer, also has been used to estimate WUE in plants using C-3 photosynthesis (Martin et al., 1999, Crop Sci. 1775). As used herein, the term "water use efficiency" refers to the amount of organic matter produced by a plant divided by the amount of water used by the plant in producing it, i.e. the dry weight of a plant in relation to the plant's water use. As used herein, the term "dry weight" refers to everything in the plant other than water, and includes, for example, carbohydrates, proteins, oils, and mineral nutrients. It is contemplated that the transgenic plants produced by the methods described herein will confer an increase in water use efficiency.

The phrase "biotic stress" as used herein refers to any adverse effect on metabolism, growth, reproduction and/or viability of a plant by biotic factors (i.e. insect pressure, disease and etc).

The phrase "biotic stress tolerance" as used herein refers to the ability of a plant to endure a biotic stress without suffering a substantial alteration in metabolism, growth, reproduction and/or viability.

As used herein the phrase "plant biomass" refers to the amount (measured in grams of air-dry or dry tissue) of a tissue produced from the plant in a growing season, which could also determine or affect the plant yield or the yield per growing area.

As used herein the phrase "plant vigor" refers to the amount (measured by weight) of tissue produced by the plant in a given time. Hence increased vigor could determine or affect the plant yield or the yield per growing time or growing area.

The term "early vigor" refers to active healthy well-balanced growth especially during early stages of plant growth, and may result from increased plant fitness due to, for example, the plants being better adapted to their environment (optimizing the use of energy resources and partitioning between shoot and root). Plants having early vigor also show increased seedling survival and a better establishment of the crop, which often results in highly uniform fields (e.g. crops growing in a uniform fashion, such as the crops reaching various stages of development at substantially the same time), and often higher yields. Therefore, early vigor may be determined by measuring various factors, such as thousand kernel weight, percentage germination, percentage emergence, seedling growth, seedling height, root length, root and shoot biomass and many more.

As used herein, "seedling vigor" refers to the plant characteristic whereby the plant emerges from soil faster, has an increased germination rate (i.e., germinates faster), has faster and larger seedling growth and/or germinates faster under cold conditions as compared to the wild type or control under similar conditions. Seedling vigor has often been defined to comprise the seed properties that determine "the potential for rapid, uniform emergence and development of normal seedlings under a wide range of field conditions".

The life cycle of flowering plants in general can be divided into three growth phases: vegetative, inflorescence, and floral (late inflorescence phase). In the vegetative phase, the shoot apical meristem (SAM) generates leaves that later will ensure the resources necessary to produce fertile offspring. Upon receiving the appropriate environmental and developmental signals the plant switches to floral, or reproductive, growth and the SAM enters the inflorescence phase (I) and gives rise to an inflorescence with flower primordia. During this phase the fate of the SAM and the secondary shoots that arise in the axils of the leaves is determined by a set of meristem identity genes, some of which prevent and some of which promote the development of floral meristems. Once established, the plant enters the late inflorescence phase where the floral organs are produced. If the appropriate environmental and developmental signals are present the plant switches to floral, or reproductive, growth. If such signals are disrupted, the plant will not be able to enter reproductive growth, therefore maintaining vegetative growth.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

Antibodies of the invention include polyclonal and monoclonal antibodies and mixtures thereof, which can be any of IgG, IgA, IgM, IgE, IgD, and any isotype thereof, for example, IgG1, IgG2, IgG3 or IgG4. In the case of a monoclonal antibody, an exemplary class of antibody is IgG. Subclasses of IgG include, for example, IgG1, IgG2, IgG3 and IgG4. Antibodies include intact and chimeric immunoglobulin molecules with two full-length heavy chains and two full-length light chains (e.g., mature portion of heavy and light chain variable region sequences) as well as subsequences/fragments of heavy or light chain which retain at least a part of a function (e.g. T6PP binding specificity or T6PP binding affinity) of parental intact antibody that specifically binds T6PP and in particular a modified T6PP. Subsequences can have the same or substantially the same binding specificity, binding affinity as parental intact and chimeric antibodies.

Monoclonal or polyclonal antibody production may be effected by techniques which are well known in the art. "Polyclonal" antibodies are antibodies obtained from different B cells resources. They are a combination of immunoglobulin molecules that secret a specific antigen, each identifying a different epitope. Polyclonal antibodies are typically produced by inoculation into a suitable mammal, such as a mouse, rabbit or goat. For example, a composition containing a T6PP protein capable of producing an antigen is injected into the mammal. The presence of the new protein induces the B-lymphocytes to produce IgG immunoglobulins specific for the T6PP antigen. The polyclonal IgG immunoglobulins are then purified from the mammal's serum.

The term "monoclonal antibody," as used herein, refers to a preparation of antibody molecules of single molecular composition. A monoclonal antibody displays a single binding specificity and affinity for a particular epitope. The process of monoclonal antibody production involves obtaining immune somatic cells with the potential for producing antibody, in particular B lymphocytes, which have been previously immunized with the antigen of interest either in vivo or in vitro and that are suitable for fusion with a B-cell myeloma line.

Mammalian lymphocytes typically are immunized by in vivo immunization of the animal (e.g., a mouse) with the desired protein or polypeptide, e.g., with a T6PP of the present invention. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rabbit, hamster, sheep and frog may also be used as hosts for preparing antibody-producing cells. See; Goding (in Monoclonal Antibodies: Principles and Practice, 2d ed., pp. 60-61, Orlando, Fla., Academic Press, 1986).

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Increased crop yield is a trait of considerable economic interest throughout the world. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigor may also be important factors in determining yield. In addition it is greatly desirable in agriculture to develop crops that may show increased yield in optimal growth conditions as well as in non-optimal growth conditions (e.g. drought, under abiotic stress conditions). Optimizing the above-mentioned factors may therefore contribute to increasing crop yield.

Seed yield is a particularly important trait, since the seeds of many plants are important for human and animal nutrition. Crops such as, corn, rice, wheat, canola and soybean account for over half the total human caloric intake whether through direct consumption of the seeds themselves or through consumption of livestock raised on processed seeds. Plant seeds are also a source of sugars, oils and many kinds of metabolites used in various industrial processes. Seeds consist of an embryo (the source of new shoots and roots) and an endosperm (the source of nutrients for embryo growth during germination and during early growth of seedlings). The development of a seed involves many genes, and requires the transfer of metabolites from the roots, leaves and stems into the developing seed. The endosperm assimilates the metabolic precursors of carbohydrates, oils and proteins and synthesizes them into storage macromolecules to fill out the grain.

Early vigor is another important aspect of yield. Improving early vigor is an important objective of modern rice breeding programs in both temperate and tropical rice cultivars. Long roots are important for proper soil anchorage in water-seeded rice. Water-seeded rice is sown directly into flooded fields where plants must emerge rapidly through water thus longer shoots allow for increased survival of young seedlings. Where drill-seeding is practiced, longer mesocotyls and coleoptiles are important for good seedling emergence. The ability to engineer early vigor into plants would be of great importance in agriculture. For example, poor early vigor has been a limitation to the introduction of maize (Zea mays L.) hybrids based on Corn Belt germplasm in the European Atlantic. In another aspect early vigor may also allow for earlier harvesting times in some crops which may serve as an advantage in many agricultural applications.

Plants engineered for improved yield under various biotic and abiotic stresses is of special interest in the field of agriculture. For example, abiotic stress is a primary cause of crop loss worldwide, reducing average yields for most major crop plants by more than 50% (Wang et al., Planta (2003) 218: 1-14). Abiotic stresses may be caused by drought, floods, salinity, extremes of temperature, chemical toxicity and oxidative stress. The ability to improve plant tolerance to abiotic stress would be of great economic advantage to farmers worldwide and would allow for the cultivation of crops during adverse conditions and in territories where cultivation of crops may not otherwise be possible.

In some instances plant yield is relative to the amount of plant biomass a particular plant may produce. A larger plant with a greater leaf area can typically absorb more light, nutrients and carbon dioxide than a smaller plant and therefore will likely gain a greater weight during the same period (Fasoula & Tollenaar 2005 Maydica 50:39). Increased plant biomass may also be highly desirable in processes such as the conversion of biomass (e.g. corn, grasses, sorghum, cane) to fuels such as for example ethanol or butanol.

The ability to increase plant yield would have many applications in areas such as agriculture, the production of ornamental plants, arboriculture, horticulture, biofuel production, pharmaceuticals, enzyme industries which use plants as factories for these molecules and forestry. Increasing yield may also find use in the production of microbes or algae for use in bioreactors (for the biotechnological production of substances such as pharmaceuticals, antibodies, vaccines, fuel or for the bioconversion of organic waste) and other such areas.

Plant breeders are often interested in improving specific aspects of yield depending on the crop or plant in question, and the part of that plant or crop which is of relative economic value. For example, a plant breeder may look specifically for improvements in plant biomass (weight) of one or more parts of a plant, which may include aboveground (harvestable) parts and/or harvestable parts below ground. This is particularly relevant where the aboveground parts or below ground parts of a plant are for consumption. For many crops, particularly cereals, an improvement in seed yield is highly desirable. Increased seed yield may manifest itself in many ways with each individual aspect of seed yield being of varying importance to a plant breeder depending on the crop or plant in question and its end use.

It would be of great advantage to a plant breeder to be able to pick and choose the aspects of yield to be altered. It may also be highly desirable to be able to pick a gene suitable for altering a particular aspect of yield (e.g. seed yield, biomass weight, water use efficiency, yield under stress conditions). For example an increase in the fill rate, combined with increased thousand kernel weight would be highly desirable for a crop such as corn. For rice and wheat a combination of increased fill rate, harvest index and increased thousand kernel weight would be highly desirable.

Trehalose is a very stable disaccharide consisting of two glucose molecules. It does not degrade when heated to 100° C. for 24 hours at a wide pH range. Its low reactivity, physiochemical properties and stability make it an exceptional osmoprotectant. In the absence of water it stabilizes proteins, membranes and other cellular structures by replacing water via hydrogen bonds with polar residues. Upon desiccation, trehalose forms a mesh glass-like structure that limits molecular motion, which prevents protein aggregation and free radical diffusion (Brumfield G (2004) Nature 428: 14-15, Paul M J (2004) Plant Biotechnol J, 2 pp. 71-82).

It was previously thought that only certain plants, such as the dessication-tolerant species like resurrection plants accumulate trehalose because they make it in sufficient quantities to be readily measured. Recent genetic and genomic evidence, however, shows that all plants examined to date have the ability to synthesize trehalose, but typically in very low amounts (Paul M J, et al. (2008) Annu Rev Plant Biol 59:417-441). Furthermore, trehalose metabolism appears to be essential as removing the plant's ability to produce trehalose, for example through mutation, is lethal (Eastmond P J, et al. (2002) Plant J 29:225-235). Most crop species contain trace amounts of trehalose (measured at the low micromolar, or even nanomolar level), although the typical accumulation is unknown for maize.

Figure 3:
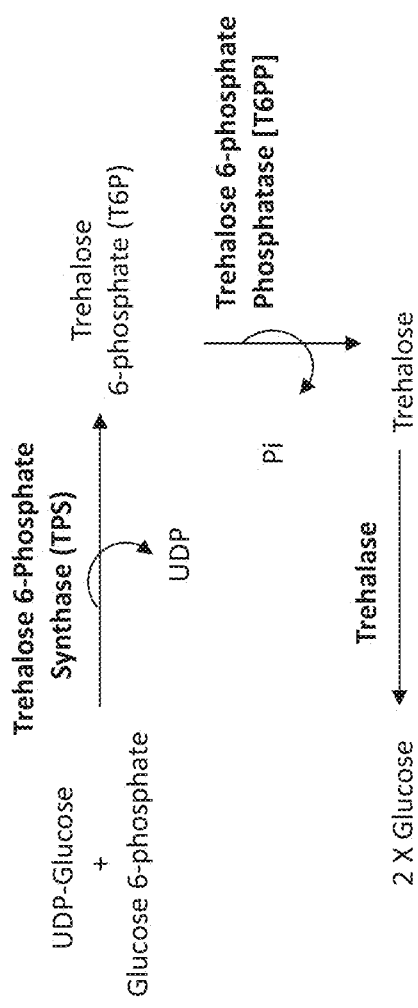
FIG. 3 shows a description of the trehalose pathway. The trehalose pathway consists of two biosynthetic enzymes, trehalose-6-phosphate synthase (TPS) and trehalose-6-phosphate phosphatase (T6PP), and one hydrolyzing enzyme, trehalase, involved in degradation.

The "trehalose pathway", as used herein, consists of two biosynthetic enzymes, trehalose-6-phosphate synthase (TPS) and trehalose-6-phosphate phosphatase (T6PP), and one hydrolyzing enzyme, trehalase, involved in degradation, please see FIG. 3. We currently do not know how many (TPS) or (T6PP) isoforms exist in maize. In the model plant *Arabidopsis*, there are a total of 11 TPS genes (Paul et al. (2008) Annu Rev Plant Biol 59:417-441) however, catalytic activity was demonstrated for only AtTPS1 (Vandesteene L, et al. (2010) Mol Plant 3:406-419). The function of the other 10 *Arabidopsis* TPS homologues remains enigmatic. There are 10 T6PP genes in *Arabidopsis*, and although most have not been well characterized they all appear to have T6PP activity (Schluepmann H, et al. (2012) J Exp Bot: 1-12; Paul et al., (2008) Annu Rev Plant Biol 59:417-441). In contrast, *Arabidopsis* contains just one gene encoding trehalase (Müller J, et al. (2001) Plant Physiol 125:1086-1093; Frison M, et al. (2007) FEBS Letters 581:4010-4016; Paul et al. 2008). The situation is similar in rice (Shima S, et al. (2007) FEBS J 274:1192-1201; Zang et al, (2011) Plant Mol Biol 76:507-522). Expression profiling data show that gene family members are differentially expressed throughout plant development (Scheulpmann et al., (2004) Plant Physiol 135:879-890; Zang et al., (2011) Plant Mol Biol 76:507-522). The diversity of tissue-specific expression and translation among some members in the T6PP and TPS gene families provides strong evidence that these enzymes perform important and perhaps distinct functions in the plant (Satoh-Nagasawa et al., (2006) Nature 441:227-230; Mustroph et al., (2009) Proc Natl Acad Sci USA 106:18843-18848; Ramon et al., (2009) Plant Cell Environ 32:1015-1032).

The trehalose pathway enzymes are also regulated at the post-translational level. TPS proteins are substrates of sucrose non-fermenting (SNF1)-related protein kinases (SnRK1s) (Zhang et al., (2009) Plant Physiol 149:1860-1871). Several TPS (AtTPS5, 6 & 7) phospho proteins bind 14-3-3 proteins (Harthill et al., (2006) Plant J 47:211-223). Coordinate phosphorylation and capping of the phosphorylation site by 14-3-3 proteins may be a possible mechanism by which TPS activity is regulated. Nitrate reductase is regulated by a similar mechanism which is based on the light/dark transition (Huber et al., (2002) Plant Mol Biol 50:1053-1063). Harthill et al. suggest that nitrate reductase, 6-phosphofructo-2-kinase/fructose-2,6-bisphosphatase (F2 KP), and TPS are all modified by the same kinase (possibly SnRK1), bind 14-3-3 proteins, and in some way may be regulated by the light/dark cycle (Harthill et al. (2006) Plant J 47:211-223).

The complexity in expression and regulation strongly suggest that the proteins in the trehalose metabolic pathway should be grouped with enzymes important to plant metabolism that serve both catalytic and regulatory roles. Their precise role is not fully understood, but the emerging model can be associated with three central functions: sugar signaling, plant development, and stress protection.

Based on published reports in microbial systems (Wiemken, A. (1990) J Gen Microbiol 58:209-217) where membrane stabilization and other benefits correlate with high trehalose levels (1-10% dry weight, g/g), early transgenic work focused on utilizing trehalose as an osmoprotectant. Several published studies implied that trehalose protects plants against drought and other osmotic stresses (Garg et al., (2002) PNAS 99:15898-15903; Paul et al., (2008) Annu Rev Plant Biol 59:417-441; Ge et al., 2008; Li et al., 2011). However when trehalose levels are measured in transgenic plants designed to over-accumulate trehalose, they were found to be very low, on the order of micrograms per gram fresh weight. Phylogenetic information also shows that in spite of the proliferation of plant trehalose pathway genes only a small number of plants accumulate trehalose metabolites to levels required for a direct effect as an osmoprotectant or stabilizer of cellular structures.

Work in the mid-1990's to produce trehalose in plants (for the food industry) was different from work to produce other 'foreign' sugar molecules in plants (Eastmand and Graham, (2003) Current Opin Plant Biol 6:231-235; Pellny et al. (2004) Plant Biotechnol J, 2 pp. 71-82; Paul M. J. (2007) Current Opinion in Plant Biology Volume 10, Issue 3, June, Pages 303-309). Altering trehalose metabolism in transgenic plants often resulted in unexpected pleotropic growth defects (Lordachescu and Imai, (2008) J Integrative Plant Biol 50:1223-1229).

P. J. Eastmond et al., were the first to show an absolute requirement for an active plant TPS gene, *Arabidopsis* TPS1 for embryo development (Eastmond P. J. et al., (2002) Plant J 29:225-235). Homozygous tps1 mutants do not develop mature seeds. Schluepmann et al. showed the tps1 mutant can be rescued by expressing the *E. coli* otsA gene coding for trehalose 6-phosphate synthase, suggesting that the active component of the trehalose pathway that regulates plant metabolism is T6P. The concentration of T6P in plant cells is very low, suggesting it functions as a signaling molecule. (Scheulpmann et al., (2004) Plant Physiol 135:879-890). A small change in its concentration may have a significant "hormone-like" effect in regulating plant metabolic processes (Rolland et al. (2002) Plant Cell: S185-S205).

There is now mounting evidence to support the involvement of the trehalose pathway in sugar signaling, which is essential to all organisms. It enables the regulation of sugar levels between the extremes of feast and famine (Eveland and Jackson, (2012) J Exp Bot: 1-11). For example, in mammals insulin regulation of blood sugar levels is an essential to maintaining optimal health.

Figure 4:
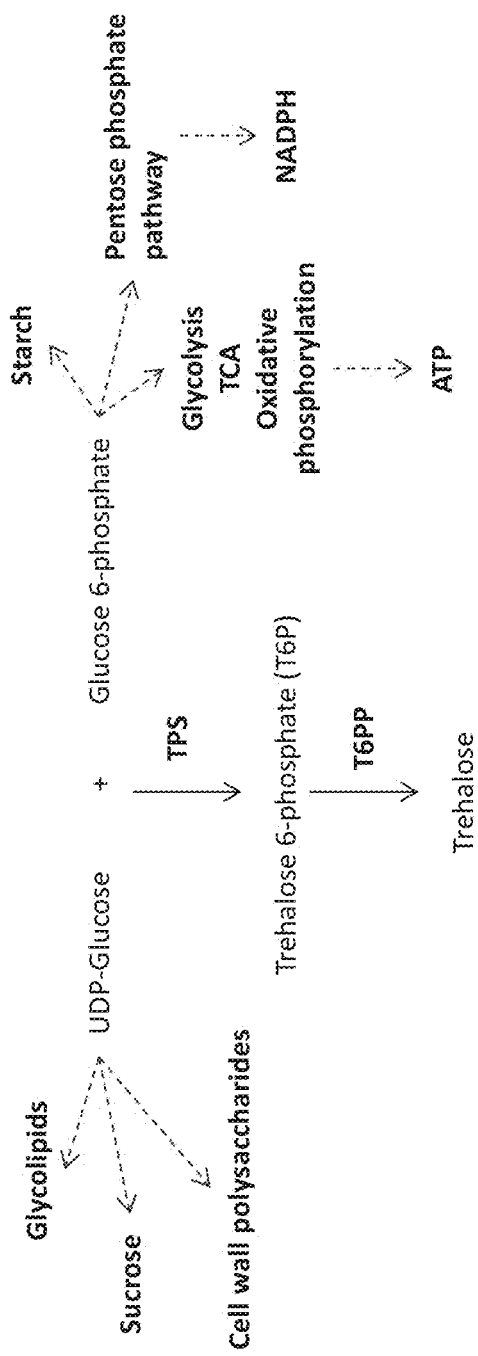
FIG. 4 shows the trehalose pathway with additional downstream products. UDPG is produced directly via sucrose synthase; G6P is produced from glucose via invertase and hexokinase or via fructose and fructose 6-phosphate (F6P) through sucrose synthase, fructokinase, and phosphoglucose isomerase. UDPG and G6P are also two central activated precursors from which many cellular functions can be ultimately derived. UDPG is the precursor for the major cell wall polysaccharides and for glycolipids. G6P is the precursor for starch synthesis, NADPH by way of the oxidative part of the pentose phosphate pathway and ATP by way of glycolysis, the citric acid cycle and oxidative phosphorylation. In addition, G6P can be converted into fructose-6-phosphate and, together with UDPG, be used for the synthesis of sucrose-6-phosphate and then sucrose. Being made from UDPG and G6P, T6P resides at the crossroads of major carbon fluxes in plants.

The concept that trehalose sugars are involved in sensing sugar and energy status is established in microbes, particularly yeast, and is now being confirmed in plants (Schluepmann et al., (2012) J Exp Bot: 1-12). In plants T6P is synthesized from G6P and UDPG, downstream products of sucrose breakdown. UDPG is produced directly via sucrose synthase; G6P is produced from glucose via invertase and hexokinase or via fructose and fructose 6-phosphate (F6P) through sucrose synthase, fructokinase, and phosphoglucose isomerase. UDPG and G6P are also two central activated precursors from which many cellular functions can be ultimately derived (FIG. 4). UDPG is the precursor for the major cell wall polysaccharides and for glycolipids. G6P is the precursor for starch synthesis, NADPH by way of the oxidative part of the pentose phosphate pathway (Masakapalli S. K. et al., (2010) Plant Physiol 152:602-619), and ATP by way of glycolysis, the citric acid cycle and oxidative phosphorylation. In addition, G6P can be converted into fructose-6-phosphate and, together with UDPG, be used for the synthesis of sucrose-6-phosphate and then sucrose. Being made from UDPG and G6P, T6P resides at the crossroads of major carbon fluxes in plants. Thus, T6P levels in plant cells may reflect the availability of hexose phosphates, UDPG, and sucrose.

Figure 5:
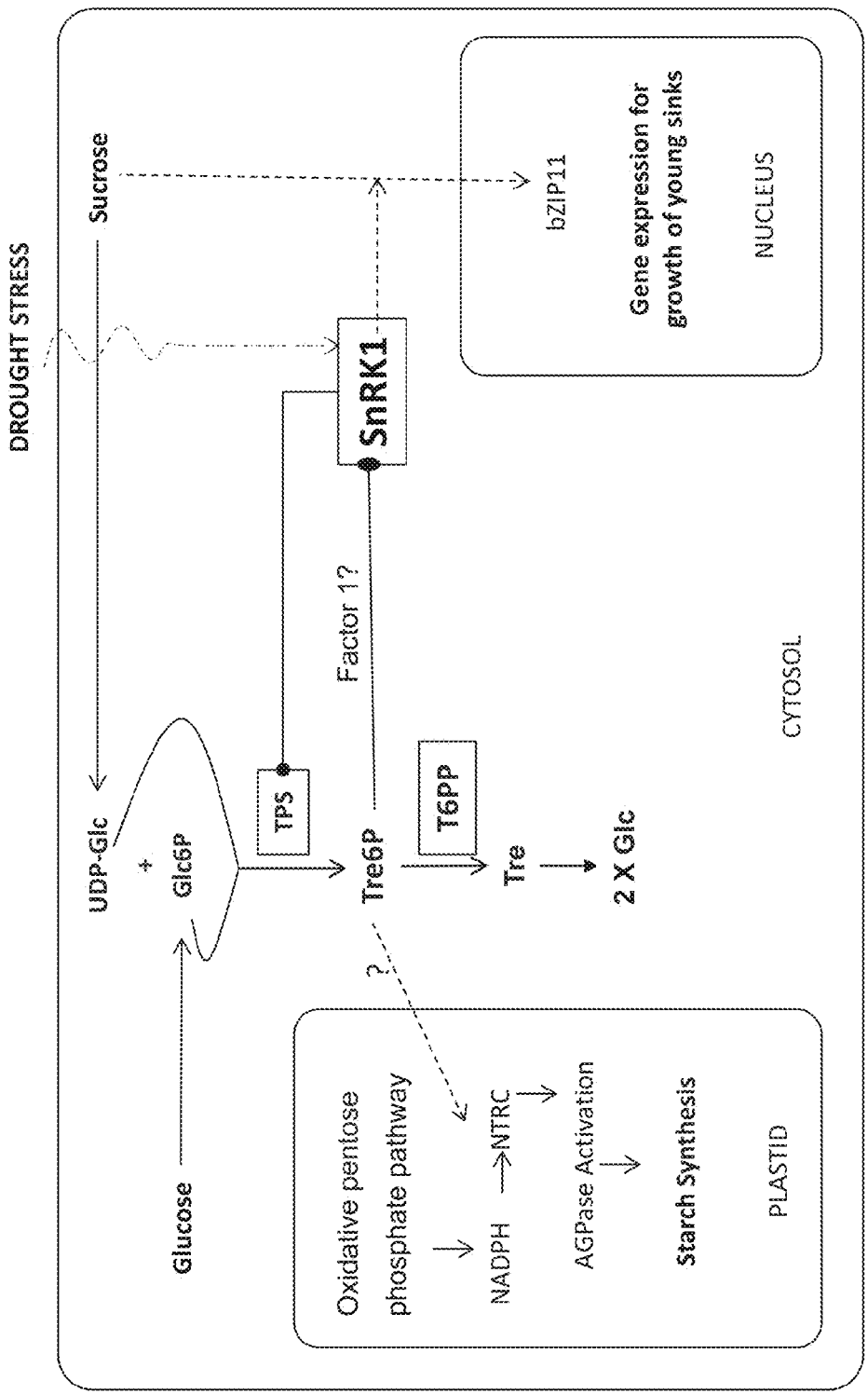
FIG. 5 describes the affect of T6P binding to SnRK1. SnRK1 is a heterotrimeric protein, and is the plant homolog of the animal AMP-activated protein kinase and yeast Sucrose non-fermenting protein kinase (SnF1).
Figure 6:
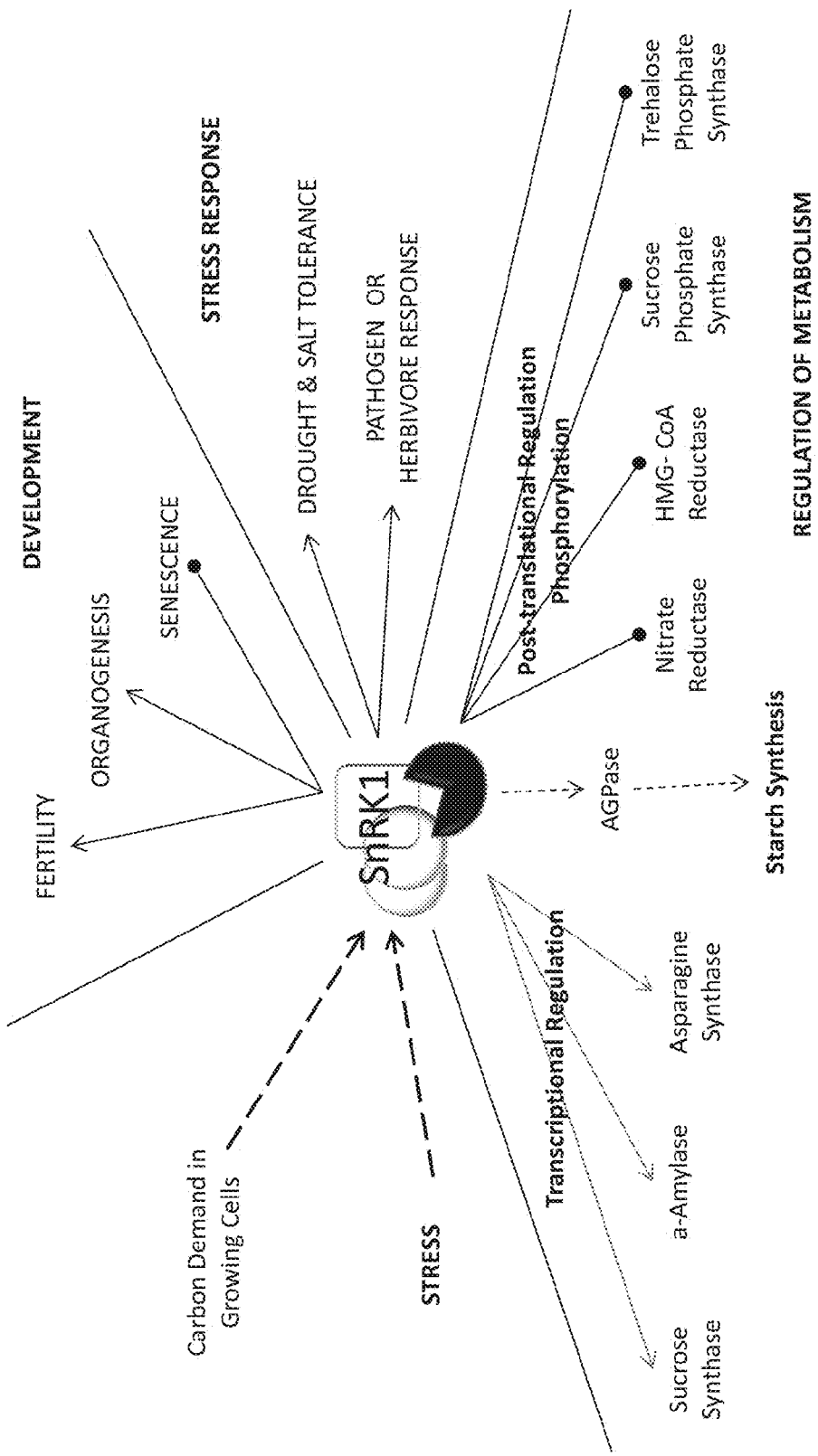
FIG. 6 shows the involvement of SnRK1 in multiple metabolic pathways in plants.

An important finding shows T6P binds to SnRK1 to inhibit its activity (Zhang et al., 2009) Plant Physiol 149: 1860-1871), please see FIG. 5. SnRK1 is a heterotrimeric protein, and is the plant homolog of the animal AMP-activated protein kinase and yeast Sucrose non-fermenting protein kinase (SnF1) (Paul et al. (2008) Annu Rev Plant Biol 59:417-441; Schluepmann et al., (2012) J Exp Bot: 1-12; Polge and Thomas (2007) Trends in Plant Science Volume 12, Issue 1, January 2007, Pages 20-28). Global gene expression in plants over expressing a SnRK1 subunit gene resembles plant response to carbon nutrient or energy stress caused by prolonged darkness, inhibition of photosynthesis or submergence (Baena-González et al., (2007) Nature 448:938-942). Increased SnRK1 therefore mediates the low-energy stress responses. While inactivation of SnRK1 promotes processes required for carbon utilization and anabolism (FIG. 6).

In *Arabidopsis*, T6P has been associated indirectly with NADPH-dependent processes (Kolbe et al., (2005) PNAS 102:11118-11123). T6P levels in *Arabidopsis* tend to be inversely correlated with G6P levels (Schleupmann et al., (2003) Proc Natl Acad Sci USA 100:6849-6854), and directly correlated with sucrose levels (Martinez-Barajas et al., 2011). In *Arabidopsis* feeding sucrose or trehalose increases T6P levels, and activates incorporation of carbon into starch, which is carbon utilization for storage. T6P is implicated in redox activation of AGPase in heterotrophic tissues (Schleupmann et al., (2012) J Exp Bot: 1-12). In addition, AGPase is markedly activated by thioredoxin-mediated reduction when T6P levels are increased by transgene expression. The NAPDH Thioredoxin Reductase C (NTRC) enzyme uses NADPH for the redox-activation of AGPase. Mutants in NTRC do not respond to trehalose feeding, suggesting T6P acts on the NTRC enzyme or upstream in the pathway for redox activation of AGPase. Taken together, T6P function in plants affects energy signaling as well as redox signaling by NADPH; T6P is required because it controls availability of NADPH the substrate for reductive biosynthesis. However the mechanisms by which T6P exerts its effect on NADPH dependent redox-signaling are unknown in plants. The nature of involvement of SnRK1 is not known in this case (Schleupmann et al., (2012) J Exp Bot: 1-12). SnRK1 is requires for AGPase activation (Kolbe et al., (2005) PNAS 102:11118-11123) and seems active both upstream and downstream of T6P in redox activation of AGPase in heterotrophic tissues.

T6P is a required metabolite as it controls substrate availability for growth. *Arabidopsis* seedlings are growth-inhibited when grown on media with trehalose and the effect is suppressed when feeding sucrose with trehalose. The growth arrest on trehalose was shown to be caused by accumulation of T6P; trehalose inhibition correlates with a 10-fold increase in T6P (Schluepmann et al., (2004) Plant Physiol 135:879-890). Growth inhibition of *Arabidopsis* seedlings is associated with significant starch accumulation in cotyledons. By contrast, root tips do not show typical starch accumulation. Trehalose feeding to seedlings disturbs carbon allocation with all the carbon remaining in the source cotyledons and apparent carbon starvation at the apices. T6P activation of AGPase and carbon sequestration in starch, however, is not the cause of growth inhibition. Instead, T6P inhibition of SnRK1 activity was shown to cause growth inhibition on trehalose because seedlings over expressing the catalytic subunit (KIN10) of SnRK1 grew on trehalose (Delatte et al., (2011) Plant Physiol 157:160-174). Thus it appears that seedlings stop growing on trehalose because T6P accumulation inhibits SnRK1 activity.

It may seem paradoxical that both too little T6P, as in tps1 mutant, and too much T6P in the absence of exogenously supplied carbon stops plant growth. The mechanism by which T6P/SnRK1 exerts control over plant metabolism is far from understood. However, not to be limited by theory, in heterotrophic tissues, T6P increases when sucrose is available. The T6P increase inhibits SnRK1 activity such that cells are allowed to go about anabolic processes required for growth. When sucrose levels or carbon availability drops, the T6P level drops, unleashing SnRK1 activity; anabolic processes are inhibited. SnRK1 activity is also known to be activated during carbon and energy stress responses (FIG. 6). SnRK1 senses the low energy or carbon signal and mediates processes required to make carbon available in sink cells for growth. SnRK1 activity is required until carbon becomes available again in heterotrophic tissues. Sucrose is then synthesized and T6P level increase sufficiently to inhibit SnRK1 activity.

This T6P/SnRK1 signaling pathway is by no means global. In *Arabidopsis* T6P binding to SnRK1 requires a still elusive soluble protein molecule, Factor 1 (Zhang et al., (2009) Plant Physiol 149:1860-1871), which could not be detected in mature leaf. In addition, subunits of the SnRK1 complex are heterogeneously distributed within plant tissues (Bitrián et al., (2011) Plant J 65:829-842). Heterogeneity is therefore expected in the T6P inhibition of SnRK1 in heterotrophic tissues and photoautotrophic tissues (Bitrian et al., (2011) Plant J 65:829-842). Also T6P is charged metabolite and is therefore not likely to be freely exported to other cells (Schleupmann et al., (2012) J Exp Bot: 1-12).

Genetic and biochemical evidence show that the trehalose pathway is essential to plant development and controls cellular morphogenesis. The loss of TPS1 enzyme activity in *Arabidopsis* is embryo-lethal (Eastmond et al., (2002) Plant J 29:225-235; Paul et al., (2008) Annu Rev Plant Biol 59:417-441). Expression of AtTPS1 has been linked to specific developmental phenotypes such as delayed embryo development, altered root and shoot growth and altered transition to flowering. The data indicate the absence of T6P impairs the embryo's ability to transition into the cell expansion phase of development (Paul et al., (2008) Annu Rev Plant Biol 59:417-441).

In maize RAMOSA3 (RA3), which is important for inflorescence branching, encodes a single domain T6PP protein (Satoh-Nagasawa et al. (2006) Nature 441:227-230). It is thought that the expression of T6PP in the areas surrounding axillary meristems may aid in transducing a mobile, short-range signal to regulate meristem identity and determinacy. Loss of RA3 activity causes severe ear abnormalities that include long axillary branches at the base of the ear in early development (Eveland & Jackson (2012) J Exp Bot: 1-11).

Chary et al. describes the identification of a cell shape phenotype-1 (csp-1) *Arabidopsis thaliana* mutant. CSP-1 shows a multitude of defects in plant developmental processes such as plant stature, leaf morphology, root development, reduced shoot branching and delayed flowering (Chary et al. (2008) Plant Physiol 146: 97-107). A mutation was found in the AtTPS6 gene. This provides significant evidence indicating that the TPS gene is an important modifier of cellular morphology and whole plant development. It is not clear what the mechanism of action underlying these dramatic developmental effects. It is possible that they are, at least partly, mediated by T6P/SnRK1 signaling pathway.

Maize T6P is present at <10 μg/GFW in most samples, making it difficult to accurately measure T6P. In addition the maize T6PP gene family is similar in size to that of rice and *Arabidopsis*, and natural T6PP accumulation is high in most tissues. This suggests that the transgenic expression of rice T6PP in maize is likely exerting its effect in a spatial and temporal manner.

It has now been discovered that the expression of several forms of trehalose-6-phosphate phosphatase (T6PP) in plants confers a significant increase in yield as well as confers resistance to various types of stress (i.e. abiotic stress). During the course of analyzing various T6PP variants transgenically expressed in plants it has been found that the transgenic plants showing the highest yield in seed also comprised T6PPs with modifications to amino acid residues associated with substrate binding. Not to be limited by theory, these proteins may have decreased enzymatic activity when directly compared to a T6PP not containing these modifications. Further, not to be limited by theory, it appears that expressing a T6PP in plant with modified enzymatic activity results in a beneficial phenotype having significant increased yield in both stress (e.g. drought) and non-stressed field conditions. Again, not to be limited by theory, this may suggest that a less active form of T6PP serves as a molecular signal therefore conferring in the plant an increase in starch, sugar and increased seed yield. In theory, this molecular signal could be a protein-protein interaction with trehalose-6-phosphate synthase (TPS) forming a complex that then may provide a signal to the plant. In theory this signal may be altered levels of trehalose-6-phosphate (T6P). Not to be limited by theory, but one possibility is that a modified T6PP when expressed in a plant forms a protein-protein complex with endogenous forms of TPS and/or T6PP. In theory this binding alters T6PP's ability to hydrolyze its substrate T6P and activates or modulates TPS to produce T6P. This interaction then confers altered levels of T6P that then signal to the plant to commit more sugars to seed and/or biomass. Alternatively, not to be limited by theory, the modified T6PP having decreased activity interacts with some other component not yet identified which results in the initiation of a cascade to signal to the plant to commit more sugars to yield and/or biomass. Based upon the theories above, many methods may be employed to produce a plant with increased yield under any condition. It is also envisioned that one could use the methods described herein to modulate the production of sugars in a plant and further employ molecular engineering techniques to transport sugars to various parts of the plants to increase for instance such things as plant biomass, seed yield, sugar content in aboveground plant material (i.e. such as sugarcane), and to consumable plant parts. Additionally these trehalose-6-phosphate phosphatase genes may find use in conferring many more desirable traits such as early vigor, stress tolerance, drought tolerance, increased nutrient use efficiency, increased root mass and increased water use efficiency.

Trehalose, a non-reducing disaccharide consisting of two glucose molecules linked via alpha-1,1 bonds. The sugar trehalose can be found in many various organisms across multiple kingdoms (e.g. plants, bacteria, insects, etc). Trehalose has been shown to be involved in carbohydrate storage function and has been further associated to play a role in stress tolerance in bacteria, fungi and insects. In plants, trehalose was initially thought to be confined to extremophiles such as the resurrection plant *Selaginella lepidophylla*, however it is now widely accepted that trehalose metabolism is ubiquitous in the plant kingdom.

Trehalose is synthesized from UDP-glucose and Glucose-6-phosphate in two enzymatic reactions. First UDP-glucose and Glucose-6-phosphate are converted to UDP (uridine diphosphate) and alpha, alpha-trehalose 6-phosphate (T6P) by the enzyme TPS (trehalose phosphate synthase). In a second step, which is catalyzed by the enzyme T6PP (trehalose phosphate phosphatase), T6P is de-phosphorylated to produce trehalose and orthophosphate. (See FIG. 3)

In yeast, the two enzymatic activities (TPS and T6PP activity) reside in a large protein complex, containing the active subunits, TPS 1 and TPS2, and the regulatory subunits, with TPS 1 having TPS activity and TPS2 having T6PP activity. In *E. coli*, the two enzymatic activities are found in separate protein complexes. In plants, the protein complex has not been characterized to date.

In *Arabidopsis thaliana*, trehalose biosynthetic enzymes have been classified into three classes:

Class I: containing four genes, AtTPS1 to AtTPS4 having high similarity to ScTPS1;

Class II: having seven members, AtTPS5 to AtTPS11, with high sequence similarity to ScTPS2; and Class III: containing 10 members, AtT6PPA to AtT6PPJ, encoding proteins with similarity to *E. coli* TPS2 and the C-terminus of ScTPS2 proteins.

Genes encoding proteins within these classes are also present in other plant species.

Within Class I and Class II, enzymatic activity has only been unambiguously determined for AtTPS1, which displays TPS activity (Blazquez et al. Plant J. March 1998; 13(5):685-9.). Surprisingly, no T6PP activity has been reported to date for any of the other Class II TPS proteins. In contrast, T6PP activity was previously described for AtT6PPA and AtT6PPB, two of the members of Class III (Vogel et al. Plant J. March 1998; 13(5):673-83). Plant Class III T6PPs contain two phosphatase consensus sequence motifs found in all T6PP enzymes described to date (Thaller et al. Protein Sci. July 1998; 7(7):1647-52).

The genetic manipulation of trehalose biosynthesis genes has been reported to lead to improved stress tolerance in plants, as well as, causing striking developmental alterations. Overexpression of *E. coli* OtsA and OtsB genes (equivalents to T6PP and TPS) in transgenic tobacco and potato plants was reported to cause developmental aberrations in roots and leaves as well as stunted plant growth. Fewer seeds were produced in the OtsA transgenic tobacco plants and the OtsB transgenic potato plants did not produced tubers (Goddijn et al. Plant Physiol. January 1997; 113(1):181-90). Similar results have been described by others (Holmstrom et al. Nature, 379, 683-684; Romero et al. Planta, 201, 293-297; Pilont-Smits et al. 1998; J Plant Physiol. 152:525-532; Schluepmann et al. Proc Natl. Acad. Sci. USA. 2003; 100(11):6849-54). Mutants defective in TPS and T6PP genes have also reportedly shown developmental defects. TPS 1 knock out mutants in *Arabidopsis* showed impaired embryo development (Eastmond et al. Plant J. January 2002; 29(2):225-35). McSteen et al. (Plant Cell 2006; 18; 518-522) mention that the isolation and characterization of a maize geneRAMOSA3 (RA3) is reported to be responsible for meristem development and inflorescence development including branching. It is suggested that the gene, gene product, and regulatory regions may be used to manipulate branching, meristem growth, inflorescence development and arrangement. Negative phenotypes associated with the expression of a transgene can have detrimental effects to a plant's relative yield. For example, without seed set, seed filling, fertility of a plant etc. there would be no increase in seed yield. Patent application U.S. 2007/0006344 is a first account to this application's knowledge of a method which describes the expression of a T6PP in a plant to confer an increase in plant yield without any negative phenotypes and/or detrimental effects to the plant biological function. U.S. Patent Application 2007/0006344 describes the use of a trehalose-6-phosphate phosphatase operably linked to a OsMADS promoter that targets the preferential expression of the T6PP to maternal reproductive tissue of a plant which resulted in a significant yield increase in maize under water deficit and well watered conditions. The following invention generally involves the identification of T6PP having modifications that confer improved yield and field efficacy in crop plants and further describes methods one may use to increase yield in a plant by utilizing modified T6PPs in a plant.

The invention provides nucleotide sequences that when transgenically expressed in a plant increases plant vigor, yield, nitrogen utilization and/or biomass under stress or non-stress conditions. It was discovered that the T6PP proteins comprising modifications which alter the activity of the T6PP protein wherein the activity is decreased when directly compared to a relative T6PP not having the modifications, confer a significant increase in both yield and/or increased tolerance to stress when these modified T6PPs are transgenically expressed in a plant. Not to be limited by theory, these modifications appear to be made at key positions within the T6PP protein which influence the binding of T6PP to its substrate T6P. In theory, the T6PPs as disclosed herein having decreased activity serves as a signal to the plant or initiates in the plant certain metabolic cascades or metabolic pathways which confer in the plant increased sugar transport to the fruit, grain, leaves, roots or other parts thus resulting in increased seed yield, biomass and/or root growth.

Not to be limited by theory, expression of a T6PP modified for decreased activity and/or modified to have increased binding potential to a endogenous TPS protein may be used to initiate a T6PP/TPS complex which then the presence of said T6PP/TPS complex confer in the plant increased yield and/or increased tolerance to stress. In another embodiment, not to be limited by theory, the T6PP/TPS complex confers in the plant altered levels of T6P which then confer in the plant increased yield and/or increased tolerance to stress. In one aspect of the invention a transgenic T6PP/TSPS complex may be transgenically expressed in a plant to confer increased yield and/or increased stress tolerance in a plant. In another embodiment, it is contemplated that various chemical structures and or molecular structures may be constructed via methods well known in the respective art to mimic the function of a T6PP/TSPS complex such as those described herein. In one embodiment, not to be limited by theory, any T6PP may be modified to have decreased substrate binding to T6P which then will confer increased yield and field efficacy when the modified T6PP are expressed transgenically in plants. In some cases the nucleotide sequences encode a protein involved in the trehalose biosynthesis pathway, in one embodiment the protein encodes a T6PP. In another embodiment of the invention, the T6PPs are isolated from the genome of an angiosperm and then modified as described herein. In a further embodiment of the invention the T6PP gene is isolated from a monocot. In one aspect, the T6PP genes, disclosed herein, are isolated from the genome of a rice plant.

The T6PP genes described herein are primarily members of the HAD superfamily of phosphatases or comprise a protein consensus sequence as depicted in SEQ ID NO: 9. The HAD phosphatase super family which may also be referred to as the DDDD superfamily of phosphatases comprise a conserved alpha/beta core domain as well as a cap domain whose function may vary (i.e. substrate binding, etc). In one embodiment of the invention, a modification is located in any one of the cap domain, phosphatase domain, A-Phosphatase box domain or the B-Phosphatase box domain of the T6PP wherein the said modification alters the binding to its substrate (e.g. T6P). In another embodiment the modifications may comprise one or more of a substitution, deletion, or addition of one or more amino acid residues to the a relative T6PP protein consensus sequence as depicted in SEQ ID NO: 9 wherein the substitution, deletion or addition of one or more amino acid residues confer altered activity of said T6PP and/or increased levels of T6P when the T6PP is transgenically expressed in a plant. Not to be limited by theory, it is believed that creating T6PP protein variants having reduced catalytic activity (i.e. decreased hydrolysis of T6P) creates a signal within the plant conferring increased yield and/or increased tolerance to stress (e.g. drought, heat, cold). In theory, it may be that a T6PP having decreased activity interacts with TPS forming a protein-protein complex.

In theory, the T6PP modified to have decreased enzyme activity may serve as a metabolic signal to the plant to commit sugars to the production of seed and/or sugars. Additionally these modified T6PPs may also serve as metabolic signals to initiate processes that confer in the plant increased tolerance to abiotic and/or biotic stresses. Again not to be limited by theory, it is believed that the plants expressing modified T6PPs having decreased activity will have modified level of trehalose as compared to a control plant or as compared to a transgenic plant overexpressing an active form of T6PP.

It is envisioned that any T6PP or enzyme having T6PP activity may be engineered to have decreased activity and thus be employed to generate transgenic plants or organisms (e.g. algae) having increased yield. In one embodiment of the invention, proteins comprising a consensus sequence such as depicted in SEQ ID NO: 9 may be employed in the methods as described herein. As used herein the term "reduced activity" refers to any decrease in T6PP activity. For instance an enzyme modified to have 1%, 5%, 10%, 20%, 30%, 40%, 50%, 60%, 65%, 70%, 75%, 80%, 85%, 90%, 95%, 96%, 97%, 98%, 99%, or 100% decrease in T6PP activity relative to a control or native T6PP gene may find use in producing transgenic plants with increased yield. In one embodiment of the invention, the T6PP polypeptide comprises a amino acid sequence having 50%, 60%, 70%, 80%, 90%, 95% or 99% sequence identity to the consensus sequence as described in SEQ ID NO: 9. In a further embodiment the T6PP comprises a consensus sequence as described in SEQ ID NO: 9 wherein at least one modification (inclusive of amino acid substitution, amino acid deletion, amino acid addition) is carried out and said modification reduces activity of said T6PP and/or increases the likelihood of said T6PP to form a protein-protein complex with TPS. In another embodiment plants expressing a T6PP variant having decreased activity and/or a T6PP having an increased likelihood of forming a protein-protein complex with TPS will have modified levels of T6P as compared to a control not expressing a T6PP variant not having decreased activity, wherein the modified level of T6P confers in the plant increased yield (e.g. seed yield, biomass, vigor), cell growth, sugar content, starch content and increased tolerance to stress (drought, heat, cold, salinity, flood, abiotic, and/or biotic stress). In another embodiment of the invention, expression of a T6PP variant having reduced activity in a plant is directed to plant reproductive tissue. In another embodiment of the invention patterns of gene expression might be important in expanding duration of drought tolerance in a plant. For instance, one may construct expression cassettes to express a modified T6PP during plant flowering thus conferring drought tolerance for this stage of development of the plant. Likewise, one may also construct expression cassettes that constitutively expresses a modified T6PP in a plant thus conferring drought tolerance throughout the plant's lifecycle. It is contemplated that T6PPs may be modeled to have decreased activity via modifications outside the conserved amino acid residues of the consensus sequence as depicted in SEQ ID NO: 9 wherein the modification decreases the binding of T6PP to T6P and/or said modifications increase the likelihood that the T6PP will form a protein-protein interaction with TPS.

In one embodiment one may decrease the activity of T6PP by irradiation of DNA and thus producing variants having decreased activity when expressed in a plant. Likewise it is contemplated that one may use common techniques such as gene shuffling to produce variants of T6PP having decreased activity. It is envisioned that one may create chemical orthogonal structures that may in a sense mimic an inactive T6PP protein structure and in one embodiment form a complex with a plant TPS therefore conferring in a plant increased yield. In another embodiment, one may create a chemical orthogonal structure that may mimic the structure of a T6PP/TPS complex which then can be applied to plants (e.g. chemical application) to confer increased yield and stress tolerance (i.e. drought tolerance). It is envisioned that chemical orthogonal structures may be applied to a plant to modulate sugar transport at given reproductive or developmental stages of the plant.

It is contemplated that the T6PP genes from any class or family may be employed in any of the methods and/or aspects of the invention disclosed herein. It is further contemplated that T6PP genes with similar sequence homology (e.g. greater than or equal to 50% 75%, 80% or 85% sequence identity to SEQ ID NO: 1 and/or molecular structure isolated or synthesized may be employed in the embodiments as described herein. T6PP has been shown to be ubiquitous amongst members of the plant kingdom and many instances have been shown to have conserved function across multiple genus and species of plants. Therefore, it is contemplated that a synthetic nucleic acid encoding a T6PP protein conferring decreased activity and/or decreased binding to T6P and/or increased binding to TPS could be employed in the methods disclosed herein to confer plants with favorable traits (e.g. increased yield, increased biomass, increased plant vigor) as described herein.

The methods disclosed herein further describe the transformation of plants with the polynucleotides such as disclosed herein. Transgenic plants comprising the polynucleotides disclosed herein may display increased cell growth, increased plant and/or seedling vigor, increased yield, increased seed weight and increased biomass. Plants produced by the methods herein are contemplated to have an increased tolerance to abiotic stress. It is envisioned that transgenic plants of the invention will confer increased root growth which may have many positive implications in water use and nutrient use efficiency of the plant as well as decreasing the incidence of soil erosion of commercial agricultural land. It is also contemplated that the plants comprising the polynucleotides as described herein may also display higher tolerance to insect feeding due to increased growth. In some instances, the plants described in the invention will have increased standability and/or reduced risk of crop lodging, therefore conferring transgenic plants that can withstand weather conditions such as strong winds or hail. The transgenic plants described herein may produce higher yield in both biomass yield and grain yield of the plant. One aspect of the invention provides various modifications one may perform on a given T6PP gene sequence that may be employed in transgenic plants to confer increased yield. The transgenic plants herein may confer an increase in yield in both optimal and/or non-optimal growing conditions.

Any reference hereinafter to a "protein useful in the methods of the invention" is taken to mean a polypeptide of the trehalose pathway as defined herein, including but not limited to, a T6PP polypeptide. Any reference hereinafter to a "nucleic acid useful in the methods of the invention" is taken to mean a nucleic acid capable of encoding a polypeptide of the trehalose pathway, such as a T6PP polypeptide.

A preferred method for modulating expression of a nucleic acid encoding a T6PP protein useful in the methods of the invention is by introducing and expressing in a plant a nucleic acid encoding a protein useful in the methods of the invention as defined below.

The nucleic acid to be introduced into a plant (and therefore useful in performing the methods of the invention) is any nucleic acid encoding an enzyme of the trehalose pathway. A "T6PP polypeptide" as defined herein refers to any polypeptide with trehalose-6-phosphate phosphatase activity comprising at least one trehalose-phosphatase domain. Trehalose-phosphatase domains are typically between 200 and 250 amino acids in length and typically comprise a phosphatase consensus sequence motif that is found in all T6PP enzymes described to date (Thaller et al. 1998). The amino acid sequence for the Trehalose-phosphatase domain is given in SEQ ID NO: 10. A person skilled in the art will readily be able to identify the presence of a Trehalose-phosphatase domain using tools and techniques known in the art. This phosphatase consensus sequence motif typically comprises two phosphatase boxes, named A and B-Phosphatase Box. SEQ ID NO: 11 represents a consensus sequence for Phosphatase box A and SEQ ID NO: 12 represents a consensus sequence for Phosphatase box B.

Preferably, the nucleic acid to be introduced into a plant encodes a T6PP protein having at least 80%, 85%, 90%, 95%, 96%, 97%, 98%, 99% or 100% sequence identity to a sequence selected from SEQ ID NOs 1, 3, 5 and 7. Most preferably, the Class T6PP nucleic acid is as represented by any of SEQ ID NOs 1, 3, 5 and 7.

Examples of proteins useful in the methods of the invention and nucleic acids encoding the same are provided herein in the Table in Example 5.

Also useful in the methods of the invention are homologs of any of the amino acid sequences given in the Table in Example 5. "Homologs" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids.

Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag ●100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company and the Table below).

TABLE

Examples of Conserved Amino Acid Substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |

TABLE-continued

Examples of Conserved Amino Acid Substitutions

| Residue | Conservative Substitutions |
|---|---|
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution modifications at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Also useful in the methods of the invention are derivatives of any one of the polypeptides given in the Table in Example 5 or orthologs or paralogs of any of the polypeptides given in the Table in Example 5 or derivatives of any orthologs or paralogs of any of the polypeptides given in the Table in Example 5. "Derivatives" include peptides, oligopeptides, polypeptides which may, compared to the amino acid sequence of the naturally-occurring form of the protein, comprise substitutions of amino acids with non-naturally occurring amino acid residues, or additions of non-naturally occurring amino acid residues. Derivatives of the polypeptides given in the Table in Example 5 are further examples which may be suitable for use in the methods of the invention. Some aspects of the invention involve the modification of residues that affect the activity of the T6PP molecule. In a one embodiment the modification decreases the activity of the T6PP molecule when assayed in vitro. In another aspect the modification lowers the binding affinity of T6PP to its substrate. In another aspect modifications can be made in the active site of the T6PP protein so that the protein's activity is decreased as compared to the T6PP protein without the modification.

"Derivatives" of a polypeptide include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

The invention is illustrated by expressing in a plant various T6PP proteins having modifications that decrease the activity of the T6PP molecule. Surprisingly, these modifications and/or the decreased activity of the T6PP molecules as described herein show increased yield as well as field efficacy in that the plants are healthy and show no adverse phenotypic effects. Performance of the invention is not restricted to these sequences. The methods of the invention may advantageously be performed using any nucleic acid encoding a protein useful in the methods of the invention as defined herein, including nucleic acids encoding orthologs, paralogs and homologs such as (but not limited to) any of the nucleic acid sequences given in the Table in Example 5.

Orthologs and paralogs encompass evolutionary concepts used to describe the ancestral relationships of genes. Paralogs are genes within the same species that have originated through duplication of an ancestral gene and orthologs are genes from different organisms that have originated through speciation, and are also derived from a common ancestral gene.

Orthologs and paralogs may easily be found by performing a so-called reciprocal Basic Local Alignment Search Tool (BLAST®) search. Typically, this involves a first BLAST involving BLASTing a query sequence (for example using any of the sequences listed in the Table in Example 5) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The Basic Local Alignment Search Tool (BLAST®) results may optionally be filtered. The full-length sequences of either the filtered results or non-filtered results are then BLASTed back (second BLAST) against sequences from the organism from which the query sequence is derived. The results of the first and second BLASTs are then compared. A paralog is identified if a high-ranking hit from the first blast is from the same species as from which the query sequence is derived, a BLAST back then ideally results in the query sequence amongst the highest hit; an ortholog is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbor joining tree, to help visualize clustering of related genes and to identify orthologs and paralogs.

The Table in Example 5 gives examples of orthologs and paralogs of the T6PP proteins represented by SEQ ID NO 2, 4, 6 and 8. Further orthologs and paralogs may readily be identified using the BLAST procedure described above.

The proteins of the invention are identifiable by the presence of the conserved Trehalose-phosphatase domain(s). The term "domain" refers to a set of amino acids conserved at specific positions along an alignment of sequences of evolutionarily related proteins. While amino acids at other positions can vary between homologs, amino acids that are highly conserved at specific positions indicate amino acids that are essential in the structure, stability or activity of a protein. Identified by their high degree of conservation in aligned sequences of a family of protein homologs, they can be used as identifiers to determine if any polypeptide in question belongs to a previously identified polypeptide family (in this case, the proteins useful in the methods of the invention and nucleic acids encoding the same as defined herein). In a preferred embodiment of the invention one or more modifications may be introduced into these highly conserved domains to decrease the activity of a particular T6PP protein thus conferring when expressed in a plant increased yield.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases also exist for the identification of domains, for example, SMART (Schultz et al. (1998) Proc. Natl. Acad. Sci. USA 95, 5857-5864; Letunic et al. (2002) Nucleic Acids Res 30, 242-244, InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), or Pfam (Bateman et al., Nucleic Acids Research 30(1): 276-280 (2002). A set of tools for in silico analysis of protein sequences is available on the ExPASY proteomics server (hosted by the Swiss Institute of Bioinformatics (Gasteiger et al., ExPASy: the proteomics server for in-depth protein knowledge and analysis, Nucleic Acids Res. 31:3784-3788 (2003)).

Domains may also be identified using routine techniques, such as by sequence alignment. Methods for the alignment of sequences for comparison are well known in the art, such methods include GAP, BESTFIT, Basic Local Alignment Search Tool (BLAST®), FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The Basic Local Alignment Search Tool (BLAST®) algorithm (Altschul et al. (1990) J Mol Biol 215: 403-10) calculates percent sequence identity and performs a statistical analysis of the similarity between the two sequences. The software for performing Basic Local Alignment Search Tool (BLAST®) analysis is publicly available through the National Centre for Biotechnology Information (NCBI). Homologs may readily be identified using, for example, the ClustalW multiple sequence alignment algorithm (version 1.83), with the default pair wise alignment parameters, and a scoring method in percentage. Global percentages of similarity and identity may also be determined using one of the methods available in the MatGAT software package (Campanella et al., BMC Bioinformatics. July 2003 10: 4-29. MatGAT: an application that generates similarity/identity matrices using protein or DNA sequences.). Minor manual editing may be performed to optimize alignment between conserved motifs, as would be apparent to a person skilled in the art. Furthermore, instead of using full-length sequences for the identification of homologs, specific domains (such as the Trehalose-phosphatase domain, or one of the motifs defined above) may be used as well.

Furthermore, T6PP proteins (at least in their native form) typically have trehalose-6-phosphate phosphatase activity. Polypeptides with trehalose-6-phosphate phosphatase activity belong to the enzymatic class of EC:3.1.3.12, according to the classification of the Enzyme Commission of the Nomenclature Committee of the International Union of Biochemistry and Molecular Biology (NC-IUBMB). Enzymes in class EC:3.1.3.12 catalyze the reaction: trehalose-6-phosphate+$H_2O$=trehalose+phosphate. It is contemplated that any T6PP or protein having T6PP activity can be modified for decreased activity via methods such as point mutation(s), irradiation, etc to confer the positive effects as described herein when expressed transgenically in a plant.

The activity of a trehalose-6-phosphate phosphatase protein may be measured by determining the levels of the substrate processed and the levels of product accumulated in an in vitro reaction, that is, by determining the level of trehalose-6-phosphate consumption and/or trehalose accumulation from the reaction. Enzymatic methods to measure trehalose can be based on hydrolyzing trehalose to glucose, such as those described by Van Dijck et al. Biochem J. August 2002 15; 366(Pt 1):63-71 and Zentella et al. Plant Physiol. April 1999; 119(4):1473-82.

Trehalose-6-phosphate levels may also be measured by HPLC (High Performance Liquid Chromatography) methods as described by Avonce et al. Plant Physiol. November 2004; 136(3):3649-59; Schluepmann et al. 2003. Alternative methods based on determining the release of inorganic phosphate from trehalose-6-phosphate have also been described Klutts et al. J Biol. Chem. (2003) 278(4):2093-100. An alternative method to determine trehalose-6-phosphate levels using liquid chromatography coupled to MS-Q3 (triple quadrupole MS) has been described by Lunn et al. Biochem J. (2006) 397(1):139-48.

Examples of nucleic acids suitable for use in performing the methods of the invention include the nucleic acid sequences given in the Table in Example 5, but are not limited to those sequences. Nucleic acid variants may also be useful in practicing the methods of the invention. Examples of such nucleic acid variants include portions of nucleic acids encoding a protein useful in the methods of the invention, nucleic acids hybridizing to nucleic acids encoding a protein useful in the methods of the invention, splice variants of nucleic acids encoding a protein useful in the methods of the invention, allelic variants of nucleic acids encoding a protein useful in the methods of the invention and variants of nucleic acids encoding a protein useful in the methods of the invention that are obtained by gene shuffling. The terms portion, hybridizing sequence, splice variant, allelic variant and gene shuffling will now be described.

Nucleic acids encoding proteins useful in the methods of the invention need not be full-length nucleic acids, since performance of the methods of the invention does not rely on the use of full-length nucleic acid sequences. Portions useful in the methods of the invention, encode a polypeptide falling within the definition of a nucleic acid encoding a protein useful in the methods of the invention as defined herein. Preferably, the portion is a portion of any one of the nucleic acids given in the Table in Example 5. The portion is typically at least 625 consecutive nucleotides in length, preferably at least 825 consecutive nucleotides in length, or at least 1025 consecutive nucleotides in length or at least 1125 consecutive nucleotides in length, the consecutive nucleotides being of any one of the nucleic acid sequences given in the Table in Example 5 in combination with suggested mutation(s) disclosed herein that will decrease the activity of the relative T6PP protein compared the same T6PP not having one or more modifications. In one aspect of the invention the portion is a portion of the nucleic acid of SEQ ID NO: 1. Preferably, the portion encodes an amino acid sequence which when used in the construction of a T6PP/TPS phylogenetic tree, such as the one depicted in FIG. 2, tends to cluster with the group of T6PP proteins comprising the amino acid sequence represented by SEQ ID NO: 2 rather than with any other group.

A portion of a nucleic acid encoding a T6PP protein as defined herein may be prepared, for example, by making one or more deletions to the nucleic acid. The portions may be used in isolated form or they may be fused to other coding (or non-coding) sequences in order to, for example, produce a protein that combines several activities. When fused to other coding sequences, the resultant polypeptide produced upon translation may be bigger than that predicted for the T6PP protein portion. It is also contemplated that T6PP molecules having no T6PP activity may confer a yield increase when expressed transgenically in a plant.

According to the present invention, there is provided a method for enhancing yield-related traits in plants, particularly increasing seed yield, comprising introducing and expressing in a plant a portion of any one of the nucleic acid sequences given in the Table in Example 5, or a portion of a nucleic acid encoding an ortholog, paralog or homologue of any of the amino acid sequences given in the Table in Example 5 wherein the proteins have been modified in a way to decrease the T6PP protein activity.

Another nucleic acid variant useful in the methods of the invention is a nucleic acid capable of hybridizing under reduced stringency conditions, preferably under stringent conditions, with a nucleic acid encoding a T6PP protein as defined herein, or with a portion as defined herein. In a preferred aspect the T6PP protein will be modified to have decreased activity as compared to a un-modified version of the same T6PP protein thus conferring any one of the following in a transgenic plant increased yield, increased biomass, increased tolerance to abiotic and biotic stress, increased plant vigor, increased sugar, increased oil content, increased seed weight, increased root growth, increased water use efficiency, increased drought tolerance, increased resistance to lodging, increased nutrient use efficiency (e.g. nitrogen) and faster plant development.

Hybridizing sequences useful in the methods of the invention, encode a polypeptide having a Trehalose-phosphatase domain and having substantially the same biological activity as T6PP proteins represented by any of the amino acid sequences given in the Table in Example 5. The hybridizing sequence is typically at least 625 consecutive nucleotides in length, preferably at least 825 consecutive nucleotides in length, more preferably at least 1025 consecutive nucleotides in length and most preferably at least 1125 consecutive nucleotides in length, the consecutive nucleotides being of any one of the nucleic acid sequences given in the Table in Example 5. Preferably, the hybridizing sequence is one that is capable of hybridizing to any of the nucleic acids given in the Table in Example 5, or to a portion of any of these sequences, a portion being as defined above. Most preferably, the hybridizing sequence is capable of hybridizing to a nucleic acid as represented by SEQ ID NO: 1 or to a portion thereof. In another preferred aspect the sequence comprises at least one modification that decreases the activity of the relative T6PP protein.

Preferably, the hybridizing sequence encodes an amino acid sequence which when used in the construction of a T6PP/TPS phylogenetic tree, such as the one depicted in FIG. 2A, tends to cluster with the group of T6PP proteins comprising the amino acid sequence represented by SEQ ID NO: 2 rather than with any other group.

Most preferably, the isolated polynucleotide molecule is capable of hybridizing under stringent conditions to a sequence represented by one of SEQ ID NOs 1, 3, 5 and 7.

According to the present invention, there is provided a method for enhancing yield-related traits in plants, particularly increasing seed yield, comprising introducing and expressing in a plant a nucleic acid capable of hybridizing to any one of the nucleic acids given in the Table in Example 5, or comprising introducing and expressing in a plant a nucleic acid capable of hybridizing to a nucleic acid encoding an ortholog, paralog or homologue of any of the nucleic acid sequences given in the Table in Example 5 wherein the sequence has been modified in a way to decrease the T6PP activity of the encoded protein.

Another nucleic acid variant useful in the methods of the invention is a splice variant encoding a T6PP protein as defined hereinabove. The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained or decreased in many aspects of the invention; this may be achieved by selectively retaining or deleting functional segments of the protein. Such splice variants may be found in nature or may be manmade. Methods for predicting and isolating such splice variants are well known in the art (see for example Foissac and Schiex (2005) BMC Bioinformatics 6: 25).

According to the present invention, there is provided a method for enhancing yield-related traits in plants, particularly increasing seed yield, comprising introducing and expressing in a plant a splice variant of any one of the nucleic acid sequences given in the Table in Example 5, or a splice variant of a nucleic acid encoding an ortholog, paralog or homologue of any of the amino acid sequences given in the Table in Example 5 wherein these molecules are further modified to have decreased activity.

Preferred splice variants are splice variants of a nucleic acid represented by SEQ ID NO: 1 or a splice variant of a nucleic acid encoding an ortholog or paralog of SEQ ID NO: 2. Preferably, the amino acid sequence encoded by the splice variant comprises any one or more of the motifs or domains as defined herein. Preferably, the amino acid sequence encoded by the splice variant, when used in the construction of a T6PP/TPS phylogenetic tree, such as the one depicted in FIG. 2A, tends to cluster with the group of Class T6PP proteins comprising the amino acid sequence represented by SEQ ID NO: 2 rather than with any other group.

Another nucleic acid variant useful in performing the methods of the invention is an allelic variant of a nucleic acid encoding a T6PP protein as defined hereinabove. Alleles or allelic variants are alternative forms of a given gene, located at the same chromosomal position. Allelic variants exist in nature, and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms. The allelic variants useful in the methods of the present invention have substantially the same biological activity as the T6PP protein of SEQ ID NO: 2 and may be mutated at positions within the protein that are correlated to any one of substrate binding, enzyme activity, secondary or tertiary structure.

According to the present invention, there is provided a method for enhancing yield-related traits in plants, particularly increasing seed yield, comprising introducing and expressing in a plant an allelic variant of any one of the nucleic acids given in the Table in Example 5, or comprising introducing and expressing in a plant an allelic variant of a nucleic acid encoding an ortholog, paralog or homologue of any of the amino acid sequences given in the Table in Example 5.

Preferably, the allelic variant is an allelic variant of SEQ ID NO: 1, 3, 4, 5 or an allelic variant of a nucleic acid encoding an ortholog or paralog of SEQ ID NO: 2. Preferably, the amino acid sequence encoded by the allelic variant comprises any one or more of the motifs or domains as defined herein. Preferably, the amino acid sequence encoded by the allelic variant, when used in the construction of a TPS/T6PP phylogenetic tree, such as the one depicted in FIG. 2, tends to cluster with the group of Class T6PP proteins comprising the amino acid sequence represented by SEQ ID NO: 2, rather than with any other group.

A further nucleic acid variant useful in the methods of the invention is a nucleic acid variant obtained by gene shuffling. Gene shuffling or directed evolution may also be used to generate variants of nucleic acids encoding T6PP proteins with decreased activity as defined above. This consists of iterations of DNA shuffling followed by appropriate screening and/or selection to generate variants of nucleic acids or portions thereof encoding T6PP proteins as defined above having a modified (decreased) biological activity (Castle et al., (2004) Science 304(5674): 1151-4; U.S. Pat. Nos. 5,811,238 and 6,395,547).

According to the present invention, there is provided a method for enhancing yield-related traits in plants, comprising introducing and expressing in a plant a variant of any one of the nucleic acid sequences given in the Table in Example 5, or comprising introducing and expressing in a plant a variant of a nucleic acid encoding an ortholog, paralog or homologue of any of the amino acid sequences given in the Table in Example 5, which variant nucleic acid is obtained by gene shuffling. In a preferred embodiment, one would screen for T6PPs having a lower rate of substrate binding and/or activity.

Preferably, the variant nucleic acid obtained by gene shuffling encodes an amino acid sequence comprising any one or more of the motifs or domains as defined herein. Preferably, the amino acid encoded sequence by the variant nucleic acid obtained by gene shuffling, when used in the construction of a TPS/T6PP phylogenetic tree, such as the one depicted in FIG. 2A, tends to cluster with the group of T6PP proteins comprising the amino acid sequence represented by SEQ ID NO: 2 rather than with any other group.

Furthermore, nucleic acid variants may also be obtained by site-directed mutagenesis. Several methods are available to achieve site-directed mutagenesis, the most common being PCR based methods (Current Protocols in Molecular Biology. Wiley Eds.). One aspect of the invention is to employ site-directed mutagenesis so to decrease the T6PP protein's ability to bind with its substrate.

Nucleic acids encoding T6PP proteins may be derived from any natural or artificial source. The nucleic acid may be modified from its native form in composition and/or genomic environment through deliberate human manipulation. Preferably the T6PP-encoding nucleic acid is from a plant, further preferably from a monocotyledonous plant, more preferably from the *Oryza* family; most preferably the nucleic acid is from rice.

The present invention also encompasses plants or parts thereof (including seeds) obtainable by the methods according to the present invention. The plants or parts thereof comprise a nucleic acid transgene encoding a T6PP protein that has been intentionally or non-intentionally modified to have decreased activity.

The invention also provides hitherto unknown T6PP nucleic acid sequences and T6PP protein sequences that may be modified as described herein for methods of conferring increased yield in a plant. These sequences may also be useful in performing the methods of the invention.

According to a further embodiment of the present invention, there is therefore provided an isolated nucleic acid molecule comprising:
  (i) a nucleic acid represented by SEQ ID NO: 1, SEQ ID NO: 2 or SEQ ID NO: 7;
  (ii) the complement of any one of the SEQ ID NOs given in (i);
  (iii) a nucleic acid encoding a T6PP protein having, in increasing order of preference, at least 80%, 85%, 90%, 95%, 96%, 97%, 98%, 99% or 100% sequence identity to any one of the amino acid sequences given in SEQ ID NO: 2, SEQ ID NO: 4, SEQ ID NO: 6 or SEQ ID NO: 8.
  (iv) a nucleic acid capable of hybridizing under stringent conditions to any one of the nucleic acids given in (i), (ii) or (iii) above.

According to a further embodiment of the present invention, there is also provided an isolated polypeptide comprising:
  (i) an amino acid sequence represented by any one of SEQ ID NO: 2, SEQ ID NO: 4, SEQ ID NO: 6 or SEQ ID NO: 8;
  (ii) an amino acid sequence having, in increasing order of preference, at least at least 80%, 85%, 90%, 95%, 96%, 97%, 98%, 99% or 100% sequence identity to any one of the amino acid sequences given in SEQ ID NO: 2, SEQ ID NO: 4, SEQ ID NO: 6 or SEQ ID NO: 8;
  (iii) derivatives of any of the amino acid sequences given in (i) or (ii) above.

The invention also provides genetic constructs, expression cassettes and vectors to facilitate introduction and/or expression of the nucleic acid sequences useful in the methods according to the invention, in a plant. The gene constructs may be inserted into vectors, which may be commercially available, suitable for transforming into plants and suitable for expression of the gene of interest in transformed cells. The invention also provides use of a gene construct as defined herein in the methods of the invention. The invention also provides a construct comprising:
  (i) nucleic acid encoding T6PP protein as defined above;
  (ii) one or more control sequences capable of driving expression of the nucleic acid sequence of (a); and optionally
  (iii) a transcription termination sequence.

Preferably the nucleic acid in the construct according to the invention is a polynucleotide molecule encoding a T6PP protein with an amino acid sequence in increasing order of preference of at least 80%, 85%, 90%, 95%, 96%, 97%, 98%, 99% or 100% sequence identity to a sequence represented by one of SEQ ID NO: 1, SEQ ID NO: 3, SEQ ID NO: 5 and SEQ ID NO: 7. Most preferably, the T6PP polynucleotide molecule is any of the nucleotide sequences of SEQ ID NO: 1, SEQ ID NO: 3, SEQ ID NO: 5 and SEQ ID NO: 7.

Plants are transformed with a vector comprising the sequence of interest (i.e., a nucleic acid encoding a T6PP polypeptide that has been intentionally or non-intentionally modified to have decreased activity. The skilled artisan is well aware of the genetic elements that must be present on the vector in order to successfully transform, select and propagate host cells containing the sequence of interest. The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognizing and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a—35 box sequence and/or—10 box transcriptional regulatory sequences. The term "regulatory element" also encompasses a synthetic fusion molecule or derivative that confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The term "promoter" refers to a nucleic acid control sequence located upstream from the transcriptional start of a gene and which is involved in recognizing and binding of RNA polymerase and other proteins, thereby directing transcription of an operably linked nucleic acid. A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule is operably to a suitable promoter.

The promoter may be a constitutive promoter, which refers to a promoter that is transcriptionally active during most, but not necessarily all, phases of its growth and development and under most environmental conditions, in at least one cell, tissue or organ. Alternatively, the promoter may be an inducible promoter, i.e. having induced or increased transcription initiation in response to a chemical (for a review see Gatz 1997, Annu. Rev. Plant Physiol. Plant Mol. Biol., 48:89-108), environmental or physical stimulus. Another example of an inducible promoter is a stress-inducible promoter, i.e. a promoter activated when a plant is exposed to various stress conditions, or a pathogen-induced promoter.

Additionally or alternatively, the promoter may be an organ-specific or tissue-specific promoter, i.e. one that is capable of preferentially initiating transcription in certain organs or tissues, such as the leaves, roots, seed tissue etc.; or the promoter may be a ubiquitous promoter, which is active in substantially all tissues or cells of an organism, or the promoter may be developmentally regulated, thereby being active during certain developmental stages or in parts of the plant that undergo developmental changes. Promoters able to initiate transcription in certain organs or tissues only are referred to herein as "organ-specific" or "tissue-specific" respectively; similarly, promoters able to initiate transcription in certain cells only are referred to herein as "cell-specific".

In one aspect of the invention, the T6PP nucleic acid or variant thereof is operably linked to a promoter that directs expression of the T6PP to plant maternal reproductive tissue such as the plant shank tissue, ear node, spikelet tissue, un-pollinated floral tissue and floral stalk tissue. Promoters such as the OsMADS promoters as described in U.S. Patent Application Publication 2007/0006344 herein incorporated by reference may be used in certain aspects of the invention.

For the identification of functionally equivalent promoters, the promoter strength and/or expression pattern of a candidate promoter may be analyzed for example by operably linking the promoter to a reporter gene and assay the expression level and pattern of the reporter gene in various tissues of the plant. Suitable well-known reporter genes include for example β-glucuronidase or β-galactosidase. The promoter activity is assayed by measuring the enzymatic activity of the β-glucuronidase or β-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally, the term "weak promoter" refers to a promoter that drives expression of a coding sequence at a low level, levels of about $1/10,000$ transcripts to about $1/100,000$ transcripts, to about $1/500,0000$ transcripts per cell. Conversely, a "strong promoter" drives expression of a coding sequence at high level, or at about $1/10$ transcripts to about $1/100$ transcripts to about $1/1,000$ transcripts per cell.

It is contemplated that regulatory elements may be used to modulate the duration for which a given trait is present. For instance, one may construct expression cassettes to express a modified T6PP during plant flowering thus conferring drought tolerance for this stage of development of the plant. Likewise, one may also construct expression cassettes that constitutively expresses a modified T6PP in a plant thus, not to be limited by theory, confers drought tolerance throughout the plant's lifecycle.

Optionally, one or more terminator sequences may be used in the construct introduced into a plant. The term "terminator" encompasses a control sequence which is a DNA sequence at the end of a transcriptional unit, after the stop codon, which signals 3'processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5'-untranslated region (UTR)) or in the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell. Biol. 8:4395-4405 (1988); Callis et al., Genes Dev. 1:1183-1200 (1987)). Such intron enhancement of gene expression is typically greatest when placed near the 5' end of the transcription unit. Use of the maize introns Adh1-S intron 1, 2, and 6, the Bronze-1 intron are known in the art. For general information, see The Maize Handbook, Chapter 116, Freeling and Walbot, Eds., Springer, N.Y. (1994). In some aspects of the invention, one may wish to increase the expression of a T6PP modified to have decrease substrate binding capabilities in a plant to confer increased yield.

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. As used herein, the term "selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilization of xylose, or antinutritive markers such as the resistance to 2-deoxyglucose). Expression of visual marker genes results in the formation of color (for example β-glucuronidase, GUS or β-galactosidase with its colored substrates, for example X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants where these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with *Agrobacteria*, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems, which have the advantage that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

The invention also provides a method for the production of transgenic plants having enhanced yield-related traits, particularly increased seed yield, relative to control plants, comprising introduction and expression in a plant of any nucleic acid encoding a T6PP protein as defined hereinabove.

One aspect of the invention provides expression cassettes comprising:
  (a) the nucleic acid sequences encoding proteins useful in the methods of the invention, or
  (b) genetic control sequence(s) which is operably linked with the nucleic acid sequence according to the invention, for example a promoter, or
  (c) a) and b)

More specifically, the present invention provides a method for the production of transgenic plants having increased yield, which method comprises:
  (i) introducing and expressing in a plant, plant part or plant cell a T6PP nucleic acid or variant thereof wherein the T6PP has decreased substrate binding activity; and
  (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen. Genet. 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the *agrobacteria* to act on plant seeds or to inoculate the plant meristem with *agrobacteria*. It has proved particularly expedient in accordance with the invention to allow a suspension of transformed *agrobacteria* to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development cycle, giving rise to transgenic plants. Thus, for example, seeds of *Arabidopsis* are treated with *agrobacteria* and seeds are obtained from the developing plants of which a certain proportion is transformed and thus transgenic [Feldman, K A and Marks M D (1987). Mol Gen Genet. 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the centre of the rosette with transformed *agrobacteria*, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension (Bechthold, N (1993). C R Acad. Sci. Paris Life Sci., 316: 1194-1199), while in the case of the "floral dip" method the developing floral tissue is incubated briefly with a surfactant-treated agrobacterial suspension [Clough, S J and Bent, A F (1998). The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantage because plastids are inherited maternally in most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol. Biol. September 2001 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

The genetically modified plant cells can be regenerated via all methods with which the skilled worker is familiar Suitable methods can be found in the above-mentioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organization. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a T6PP protein as defined hereinabove. Preferred host cells according to the invention are plant cells.

Host plants for the nucleic acids or the vector used in the method according to the invention, the expression cassette or construct or vector are, in principle, advantageous in all plants, which are capable of synthesizing the polypeptides used in the inventive method.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

According to one feature of the invention, the modulated expression is increased expression. Methods for increasing expression of nucleic acids or genes, or gene products, are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added as described above.

Other control sequences (besides promoter, enhancer, silencer, intron sequences, 3'-UTR and/or 5'-UTR regions, micro-RNA target sites, may be protein and/or RNA stabilizing elements.

As mentioned above, a method for modulating expression of a nucleic acid encoding a T6PP protein modified to have decreased activity is by introducing and expressing in a plant a nucleic acid encoding a T6PP protein; however the effects of performing the method, i.e. enhancing yield-related traits may also be achieved using other well known techniques. A description of some of these techniques will now follow.

One such technique is T-DNA activation tagging (Hayashi et al. Science (1992) 1350-1353), which involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

The effects of the invention may also be reproduced using the technique of TILLING (Targeted Induced Local Lesions In Genomes). This is a mutagenesis technology useful to generate and/or identify a nucleic acid encoding a Class III T6PP protein with modified expression and/or activity. TILLING also allows selection of plants carrying such mutant variants. These mutant variants may exhibit modified expression, either in strength or in location or in timing (if the mutations affect the promoter for example). These mutant variants may exhibit higher Class III T6PP protein activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet. 5(2): 145-50).

The effects of the invention may also be reproduced using homologous recombination, which allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offring a et al. (1990) EMBO J. 9(10): 3077-84) but also for crop plants, for example rice (Terada et al. (2002) Nat Biotech 20(10): 1030-4; Iida and Terada (2004) Curr. Opin. Biotech 15(2): 132-8).

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of suitable control plants.

The terms "increase", "improving" or "improve" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to the wild type plant as defined herein.

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

Since the transgenic plants according to the present invention have increased yield, it is likely that these plants exhibit an increased growth rate (during at least part of their life cycle), relative to the growth rate of control plants at a corresponding stage in their life cycle. The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigor, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigor. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding a T6PP protein as defined herein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects. Another abiotic stress may result from a nutrient deficiency, such as a shortage of nitrogen, phosphorus and potassium.

The methods of the present invention may be performed under non-stress conditions or under conditions of mild drought to confer plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinization are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under drought conditions increased yield relative to suitable control plants grown under comparable conditions. Therefore, according to the present invention, there is provided a method for enhancing yield-related traits in plants grown under non-stress conditions or under drought conditions, which method comprises increasing expression in a plant of a nucleic acid encoding a modified T6PP polypeptide having decreased substrate binding and/or activity.

In one embodiment of the invention, the enhanced yield-related trait is manifested as an increase in one or more of the following: total number of seeds per plant, number of filled seeds per plant and seed weight per plant. Preferably, these increases are found in plants grown under non-stress conditions.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising: *Acer* spp., *Actinidia* spp., *Abelmoschus* spp., *Agropyron* spp., *Allium* spp., *Amaranthus* spp., *Ananas comosus, Annona* spp., *Apium graveolens, Arachis* spp., *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Benincasa hispida, Bertholletia excelsa, Beta vulgaris, Brassica* spp. (e.g. *Brassica napus, Brassica rapa* ssp. [canola, oilseed rape, turnip rape]), *Cadaba farinosa, Camellia sinensis, Canna indica, Capsicum* spp., *Carex data, Carica papaya, Carissa macrocarpa, Carya* spp., *Carthamus tinctorius, Castanea* spp., *Cichorium endivia, Cinnamomum* spp., *Citrullus lanatus, Citrus* spp., *Cocos* spp., *Coffea* spp., *Colocasia esculenta, Cola* spp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eriobotrya japonica, Eugenia uniflora, Fagopyrum* spp., *Fagus* spp., *Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus* spp., *Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Passiflora edulis, Pastinaca sativa, Persea* spp., *Petroselinum crispum, Phaseolus* spp., *Phoenix* spp., *Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Triticosecale rimpaui, Triticum* spp. (e.g. *Triticum aestivum, Triticum durum, Triticum turgidum, Triticum hybernum, Triticum macha, Triticum sativum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, sorghum and oats.

The present invention also encompasses use of nucleic acids encoding the T6PP protein described herein and use of these T6PP proteins in enhancing yield-related traits in plants.

Nucleic acids encoding the T6PP protein described herein, or the T6PP proteins themselves, may find use in breeding programs in which a DNA marker is identified which may be genetically linked to a T6PP encoding gene wherein the T6PP protein has decreased activity or substrate binding. The nucleic acids/genes, or the T6PP proteins themselves may be used to define a molecular marker. This DNA or protein marker may then be used in breeding programs to select plants having enhanced yield-related traits as defined hereinabove in the methods of the invention.

Nucleic acids encoding T6PP proteins may also be used as probes for genetically and physically mapping the genes that they are a part of, and as markers for traits linked to those genes. Such information may be useful in plant breeding in order to develop lines with desired phenotypes. Such use of T6PP protein-encoding nucleic acids requires only a nucleic acid sequence of at least 15 nucleotides in length. The Class III T6PP protein-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the T6PP protein-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the T6PP protein-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154). Although current methods of FISH mapping favor use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using nucleic acids. Examples include allele-specific amplification (Kazazian (1989) J. Lab. Clin. Med. 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

In one aspect of the invention, not to be limited by theory, the T6PP comprising mutations as described herein have a reduced activity and further form a protein-protein complex with TPS. Not to be limited by theory, one possible aspect of the invention is the protein-protein T6PP/TPS complex which may be used to confer in a plant increased yield and increased tolerance to stress. In another aspect, one could modify any T6PP polypeptide having the consensus sequence of SEQ ID NO: 9 to have lower binding affinity to T6P thus increasing the incidence of a T6PP/TPS protein complex. It is envisioned that in one aspect it may be possible to create or use existing chemical that may mimic the complex or create orthogonal structures that may be employed to mimic the T6PP/TPS complex. In one aspect, not to be limited by theory, is that one or more mutations may be carried out in the B-phosphatase Box of any given T6PP protein to confer in a plant increased yield.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

The present invention will now be described with reference to the following figures in which:

EXAMPLES

Example 1

Identification and Cloning of the Rice T6PP cDNA Sequence into a Binary Vector

The first vascular plant trehalose-6-phosphate phosphatase genes were cloned from *Arabidopsis thaliana* by complementation of a yeast TPS2 deletion mutant (Vogel et al. 1998). The genes designated AtT6PPA and AtT6PPB (GenBank accessions AF007778 and AF007779) were shown at that time to have trehalose-6-phosphate phosphatase activity. The AtT6PPA and AtTT6PPB protein sequences were used in TBLASTN queries (Basic Local Alignment Search Tool, BLAST®) of maize and rice sequence databases. Sequence alignments organized the hits into individual genes. Three maize and three rice T6PP homologs were identified. The rice T6PP (OsT6PP) cDNA sequence as indicated by SEQ ID NO. 1 was amplified using high-fidelity PCR. The 50 µL reaction mixture consisted of 1 µL rice cDNA library (prepared from callus mRNA in Stratagene's Lambda Unizap Vector, primary library size>1×10$^6$ pfu, amplified library titer>1×10$^{12}$ pfu/mL), 200 µM dNTPs, 1 µL 20 µM of oligonucleotide primer T6PP-EC-5 (5'-catggaccatggatttgagcaatagctcac-3') and 1 µL 20 µM of oligonucleotide primer T6PP-EC-3 (5'-atcgcagagctca-cactgagtgcttcttcc-3'), 5 µL 10× Cloned PFU buffer and 2.5 Units of Pfuturbo DNA polymerase. The thermocycling program was 95° C. for 2 minutes followed by 40 cycles of (94° C. for 15 seconds, 50° C. for 1 minute, 72° C. for 1 minute) followed by 72° C. for 10 minutes. The rice T6PP product was cloned with the Zero Blunt TOPO PCR cloning kit. The pCR-Blunt-II-TOPO OsT6PP is identified by digesting 5 µL pCR-Blunt-II-TOPO-OsT6PP miniprep DNA with EcoRI in a 20 µL reaction containing 2 µg BSA and 2 µL 1O× EcoRI restriction endonuclease buffer. The reaction is incubated at 37° C. for 2 hours and the pCR-Blunt-II-TOPO-OsT6PP (EcoRI) products were resolved on 1% TAE agarose. The pCR-Blunt-II-TOPO-OsT6PP clone is then sequenced. The OsT6PP cDNA was flanked by NcoI/SacI restriction endonuclease sites. The OsT6PP was then further cloned into a binary vector as described in Example 8 of U.S. Patent Application Publication 2007/0006344 (therein referred to OsT6PP-3 and indicated by nucleotide SEQ ID NO: 531 and protein SEQ ID NO: 532)

Example 2

Initial Evaluation of Rice T6PP Maize Events in the Greenhouse

Rice T6PP maize events comprising SEQ ID NO: 1 operably linked to a promoter having preferential expression in maternal reproductive tissue (i.e. OsMADS promoter) were generated and further evaluated in both the greenhouse and field as described in Examples 8-13 in U.S. Patent Application Publication 2007/0006344. Initial greenhouse and field evaluation of the maize events indicated some events having a yield increases in both non-drought and drought conditions (See U.S. Patent Application Publication 2007/0006344 herein incorporated by reference).

Example 3

Evaluation and Identification High Yielding T6PP Maize Events

The maize events shown to confer a yield increase in the trials described in Example 2 and more specifically in U.S. Patent Application Publication 2007/0006344 were further characterized for yield and field efficacy. These events contained either binary construct 15777 or 15769 as is described in U.S. Patent Application Publication 2007/0006344. Essentially binary construct 15769 comprises an expression cassette having a OsT6PP (indicated in SEQ ID NO: 1 of the current application) operably linked to a OsMADS6 promoter (SEQ ID NO: 13). Binary construct 15777 contains the same expression cassette (OsMADS6 promoter and OsT6PP coding sequence) with the addition of transcriptional enhancers upstream of the OsMADS6 promoter. The details and specifics of both these constructs may again be found in the U.S. Patent Application Publication 2007/0006344. Overall there were 645 T0 maize events generated from 15769 and 587 maize events were generated from the 15777 binary construct. Selection of stable events showing good growth in greenhouse and field conditions resulted in relatively few events being carried forward for field trials. The high level of attrition led to only 17 events showing field efficacy. Events derived from maize plants transformed with the 15777 binary construct proved to be most efficacious in the field testing. Two events (herein referred to as "Event 1" and "Event 2") were selected based upon viability and performance in managed stress environments (yield preservation under drought at flowering) and in agronomic trials which measured yield. Overall, best performing events transformed with construct 15777 demonstrated a significant bushel per acre yield advantage over control check samples.

Example 4

Event 1 and 2 Sequence Analysis

Event 1 and event 2 were further analyzed by sequencing of the T6PP CDS. PCR was used to amplify the integrated OsT6PP coding sequence using primers which anneal to the 5' and 3' region of the coding sequence. The respective PCR amplicons resulted in the approximate 1.1 Kb band size as would be expected from the coding sequence of the OsT6PP as depicted in SEQ ID NO: 1, herein known as OsT6PP-WT, which was the sequence that was comprised in the relative expression cassette. The amplicons were further sequenced as is well established in the art. Sequencing data indicated that both events (1 and 2) contained modifications. Event 1 contained a single point mutation at nucleotide 730 respective to SEQ ID NO: 1 (T*CATTA where * indicates point of mutation), herein known as OsT6PP-H244D. This single mutation led to an amino acid mutation at residue 244 relative to SEQ ID NO: 2 changing a His residue to an Asp residue as is represented in SEQ ID NO: 3 herein interchangeably referred to as the "T6PP single modification". Event 2 was found to contain two modifications at nucleotides 305 (TG*CTTCC where * indicates point of mutation) and 388 (CGCC*ATT where * indicates point of mutation) respective to SEQ ID NO: 1, herein known as OsT6PP-I129F. The two point nucleotide mutations identified in Event 2 resulted in a change from Ala to Val at position 102 and Ile changed to Phe at position 129 or the T6PP polypeptide as represented by SEQ ID NO 5 herein interchangeably referred to as the "T6PP double modification". Interestingly, as shown in subsequent Examples, two of these mutations are located in highly conserved domains of the T6PP protein. The Ala to Val at position 102 falls outside of the highly conserved regions. The highly conserved domains are involved in substrate binding and/or protein-protein interactions when forming a complex.

Example 5

Identification of T6PPs Having Similar Homology and Function that May be Improved Through the Introduction of Mutations Sequences (full length cDNA, ESTs or genomic) related to SEQ ID NO: 1 and/or protein sequences related to SEQ ID NO: 2 can be identified amongst those maintained in the Entrez Nucleotides database at the National Center for Biotechnology Information (NCBI) using database sequence search tools, such as the Basic Local Alignment Tool (BLAST ®) (Altschul et al. (1990) J. Mol. Biol. 215:403-410; and Altschul et al. (1997) Nucleic Acids Res. 25:3389-3402). The program can be used to find regions of local similarity between sequences by comparing nucleic acid or polypeptide sequences to sequence databases and by calculating the statistical significance of matches. The polypeptide encoded by SEQ ID NO: 1 may be used with the TBLASTN algorithm, with default settings and the filter to ignore low complexity sequences set off. The output of the analysis may be viewed by pair-wise comparison, and ranked according to the probability score (E-value), where the score reflects the probability that a particular alignment occurs by chance (the lower the E-value, the more significant the hit). In addition to E-values, comparisons may also be scored by percentage identity. Percentage identity refers to the number of identical nucleotides (or amino acids) between the two compared nucleic acid (or polypeptide) sequences over a particular length. In some instances, the default parameters can be adjusted to modify the stringency of the search.

The table below provides a list of nucleic acid and protein sequences related to the nucleic acid sequence as represented by SEQ ID NO: 1 and the protein sequence represented by SEQ ID NO: 2 that may be useful in various aspects of the invention. Sequences were indicated through sequence homology search as well as T6PP molecules indicated in the art.

| NAME | SOURCE ORGANISM | nt/pt | SEQ ID NO: | DATABASE ACCESSION NO. |
|---|---|---|---|---|
| SEQ ID NO: 1 | *Oryza sativa* | nt | 1 | N/A |
| SEQ ID NO: 2 | *Oryza sativa* | pt | 2 | N/A |
| SEQ ID NO: 3 | *Oryza sativa* | nt | 3 | N/A |
| SEQ ID NO: 4 | *Oryza sativa* | pt | 4 | N/A |
| SEQ ID NO: 5 | *Oryza sativa* | nt | 5 | N/A |
| SEQ ID NO: 6 | *Oryza sativa* | pt | 6 | N/A |
| SEQ ID NO: 7 | *Oryza sativa* | nt | 7 | N/A |
| SEQ ID NO: 8 | *Oryza sativa* | pt | 8 | N/A |
| AT1G22210 | *Arabidopsis thaliana* | nt | N/A | AT1G22210 |
| AT1G22210 | *Arabidopsis thaliana* | pt | N/A | AT1G22210 |
| AT1G35910 | *Arabidopsis thaliana* | nt | N/A | AT1G35910 |
| AT1G35910 | *Arabidopsis thaliana* | pt | N/A | AT1G35910 |
| AT1G78090 | *Arabidopsis thaliana* | nt | N/A | AT1G78090 |
| AT1G78090 | *Arabidopsis thaliana* | pt | N/A | AT1G78090 |
| AT2G22190 | *Arabidopsis thaliana* | nt | N/A | AT2G22190 |
| AT2G22190 | *Arabidopsis thaliana* | pt | N/A | AT2G22190 |
| AT4G12430 | *Arabidopsis thaliana* | nt | N/A | AT4G12430 |
| AT4G12430 | *Arabidopsis thaliana* | pt | N/A | AT4G12430 |
| AT4G22590 | *Arabidopsis thaliana* | nt | N/A | AT4G22590 |
| AT4G22590 | *Arabidopsis thaliana* | pt | N/A | AT4G22590 |
| At4g39770 | *Arabidopsis thaliana* | nt | N/A | At4g39770 |
| At4g39770 | *Arabidopsis thaliana* | pt | N/A | At4g39770 |
| AT5G10100 | *Arabidopsis thaliana* | nt | N/A | AT5G10100 |
| AT5G10100 | *Arabidopsis thaliana* | pt | N/A | AT5G10100 |
| AT5G51460 | *Arabidopsis thaliana* | nt | N/A | AT5G51460 |
| AT5G51460 | *Arabidopsis thaliana* | pt | N/A | AT5G51460 |

-continued

| NAME | SOURCE ORGANISM | nt/pt | SEQ ID NO: | DATABASE ACCESSION NO. |
|---|---|---|---|---|
| AT5G65140 | Arabidopsis thaliana | nt | N/A | AT5G65140 |
| AT5G65140 | Arabidopsis thaliana | pt | N/A | AT5G65140 |
| pOP-lcl|scaff__II.875 | Populus trichocarpa | nt | N/A | pOP-lcl|scaff__II.875 |
| pOP-lcl|scaff__II.875 | Populus trichocarpa | pt | N/A | pOP-lcl|scaff__II.875 |
| pOP-lcl|scaff__V.739 | Populus trichocarpa | nt | N/A | pOP-lcl|scaff__V.739 |
| pOP-lcl|scaff__V.739 | Populus trichocarpa | pt | N/A | pOP-lcl|scaff__V.739 |
| pOP-lcl|scaff__VII.559 | Populus trichocarpa | nt | N/A | pOP-lcl|scaff__VII.559 |
| pOP-lcl|scaff__VII.559 | Populus trichocarpa | pt | N/A | pOP-lcl|scaff__VII.559 |
| pOP-llcl|scaff__127.52 | Populus trichocarpa | nt | N/A | pOP-llcl|scaff__127.52 |
| pOP-llcl|scaff__127.52 | Populus trichocarpa | pt | N/A | pOP-llcl|scaff__127.52 |
| pOP-llcl|scaff__III.843 | Populus trichocarpa | nt | N/A | pOP-llcl|scaff__III.843 |
| pOP-llcl|scaff__III.843 | Populus trichocarpa | pt | N/A | pOP-llcl|scaff__III.843 |
| pOP-llcl|scaff__V.167 | Populus trichocarpa | nt | N/A | pOP-llcl|scaff__V.167 |
| pOP-llcl|scaff__V.167 | Populus trichocarpa | pt | N/A | pOP-llcl|scaff__V.167 |
| pOP-llcl|scaff__XII.1254 | Populus trichocarpa | nt | N/A | pOP-llcl|scaff__XII.1254 |
| pOP-llcl|scaff__XII.1254 | Populus trichocarpa | pt | N/A | pOP-llcl|scaff__XII.1254 |
| pOP-llcl|scaff__XV.1052 | Populus trichocarpa | nt | N/A | pOP-llcl|scaff__XV.1052 |
| pOP-llcl|scaff__XV.1052 | Populus trichocarpa | pt | N/A | pOP-llcl|scaff__XV.1052 |
| Os02g0661100 | Oryza sativa | nt | N/A | Os02g0661100 |
| Os02g0661100 | Oryza sativa | pt | N/A | Os02g0661100 |
| Os02g0753000 | Oryza sativa | nt | N/A | Os02g0753000 |
| Os02g0753000 | Oryza sativa | pt | N/A | Os02g0753000 |
| Os03g0386500 | Oryza sativa | nt | N/A | Os03g0386500 |
| Os03g0386500 | Oryza sativa | pt | N/A | Os03g0386500 |
| Os06g0222100 | Oryza sativa | nt | N/A | Os06g0222100 |
| Os06g0222100 | Oryza sativa | pt | N/A | Os06g0222100 |
| Os07g0485000 | Oryza sativa | nt | N/A | Os07g0485000 |
| Os07g0485000 | Oryza sativa | pt | N/A | Os07g0485000 |
| Os07g0624600 | Oryza sativa | nt | N/A | Os07g0624600 |
| Os07g0624600 | Oryza sativa | pt | N/A | Os07g0624600 |
| Os09g0369400 | Oryza sativa | nt | N/A | Os09g0369400 |
| Os09g0369400 | Oryza sativa | pt | N/A | Os09g0369400 |
| Os10g0553300 | Oryza sativa | nt | N/A | Os10g0553300 |
| Os10g0553300 | Oryza sativa | pt | N/A | Os10g0553300 |
| Aquilegia_TC11239 | Aquilegia ssp | nt | N/A | Aquilegia_TC11239 |
| Aquilegia_TC11239 | Aquilegia ssp | pt | N/A | Aquilegia_TC11239 |
| Aquilegia_TC17706 | Aquilegia ssp | nt | N/A | Aquilegia_TC17706 |
| Aquilegia_TC17706 | Aquilegia ssp | pt | N/A | Aquilegia_TC17706 |
| Bc_Q4AC11 | Brassica campestris | nt | N/A | Bc_Q4AC11 |
| Bc_Q4AC11 | Brassica campestris | pt | N/A | Bc_Q4AC11 |
| Br_Q4ABQ9 | Brassica rapa | nt | N/A | Br_Q4ABQ9 |
| Br_Q4ABQ9 | Brassica rapa | pt | N/A | Br_Q4ABQ9 |
| Gh_TC35369 | Gossypium_hirsutum | nt | N/A | Gh_TC35369 |
| Gh_TC35369 | Gossypium_hirsutum | pt | N/A | Gh_TC35369 |
| Hv_TC139314 | Hordeum vulgare | nt | N/A | HV_TC139314 |
| Hv_TC139314 | Hordeum vulgare | pt | N/A | HV_TC139314 |
| Mt_TC108059 | Medicago_truncatula | nt | N/A | Mt_TC108059 |
| Mt_TC108059 | Medicago_truncatula | pt | N/A | Mt_TC108059 |
| Mt_TC108097 | Medicago_truncatula | nt | N/A | Mt_TC108097 |
| Mt_TC108097 | Medicago_truncatula | pt | N/A | Mt_TC108097 |
| Nb_TC7464 | Nicotiana benthamiana | nt | N/A | Nb_TC7464 |
| Nb_TC7464 | Nicotiana benthamiana | pt | N/A | Nb_TC7464 |
| Nt_Q3ZTF5 | Nicotiana tabacum | nt | N/A | Nt_Q3ZTF5 |
| Nt_Q3ZTF5 | Nicotiana tabacum | pt | N/A | Nt_Q3ZTF5 |
| Nt_TC7310 | Nicotiana tabacum | nt | N/A | Nt_TC7310 |
| Nt_TC7310 | Nicotiana tabacum | pt | N/A | Nt_TC7310 |
| Sb_TC17204 | Sorghum_bicolor | nt | N/A | Sb_TC17204 |
| Sb_TC17204 | Sorghum_bicolor | pt | N/A | Sb_TC17204 |
| St_TC151769 | Solanum_tuberosum | nt | N/A | St_TC151769 |
| St_TC151769 | Solanum_tuberosum | pt | N/A | St_TC151769 |
| Ta_TC252250 | Triticum_aestivum | nt | N/A | Ta_TC252250 |
| Ta_TC252250 | Triticum_aestivum | pt | N/A | Ta_TC252250 |
| Zm_ABD92779 | Zea mays | nt | N/A | Zm_ABD92779 |
| Zm_ABD92779 | Zea mays | pt | N/A | Zm_ABD92779 |
| Zm_ABD92780 | Zea mays | nt | N/A | Zm_ABD92780 |
| Zm_ABD92780 | Zea mays | pt | N/A | Zm_ABD92780 | nt = nucleotide
pt = protein
N/A = Not applicable

Following identification of the T6PPs listed in table above, these T6PPs were next aligned with SEQ ID NOs: 1, 3, and 5 (using Vector NTI alignment tools by INVITROGEN Inc) to determine whether or not the mutations are occurring in conserved regions of the protein. The alignment identified a high amount of conserved sequence across the various T6PP proteins and was used to develop the consensus sequence as depicted in SEQ ID NO: 9. FIG. 2 describes the relationship of the identified T6PPs via a phlyogentic tree. The consensus sequence can be used to modify any of the T6PP nucleotides and/or proteins listed in table above so that when employed in a transgenic plant will result in increased yield and/or increase tolerance to stress as well as show efficacy in the field. It is also contemplated that any protein having a consensus sequence comprising 50%, 60%, 70%, 80%, 90%, 95%, 99% or 100% sequence identity to SEQ ID NO: 9 and as show in FIG. 10 may be modified as described herein and expressed in plants as described herein.

The consensus sequence displays the highly conserved residues present across the multiple T6PP polypeptides listed in the Table above. It is also contemplated that this consensus sequence would also be applicable to other T6PPs not listed in the Table above. The "X" marked positions in the consensus sequence above indicates regions of variability wherein any other single letter refers to the common single letter amino acid notation commonly used in the art. The underlined amino acid residues indicate regions that may be modified to construct T6PP polypeptides that confer increased yield and/or increased stress resistance in a transgenic plant. In one aspect any one of the residues DYDGTLSPIV (SEQ ID NO: 18)which encode a B-phosphatase box may be modified to confer proteins that when expressed in a plant may confer increased yield and/or increased tolerance to stress. In an embodiment of the invention the I (Isoleucine) in the amino acid sequence encoding a B-phosphatase box "DYDGTLSPIV" from the consensus sequence above is changed to an F (Phenylalanine) to encode (DYDGTLSPFV) (SEQ ID NO: 19). In another embodiment the "X" in the consensus sequence above is a V (Valine), which is a change from Alanine in the original sequence. This change is outside of a conserved domain and may not affect enzyme activity. Another embodiment would include altering the "H" (Histidine) within the "CVSVHFRCV" (SEQ ID NO: 20) of the consensus sequence above, is changed to a D (Aspartic Acid) altering the consensus sequence to the sequence "CVSVDFRCV" (SEQ ID NO: 21). It is contemplated that any modification to at least one conserved amino acid residue of SEQ ID NO: 7 wherein the modification results in a decrease in T6PP activity may be expressed in a plant to confer increased yield in stress and non-stress conditions.

Example 6

Methods for Designing and Testing Modified T6PP Proteins

Literature used for the T6PP variant design: The α/β hydrolase fold. David L. 011 is et al. (1992) Protein Engineering. vol. 5 197-211. Of barn owls and bankers: a lush variety of α/β hydrolases. Heikinheimo P., Goldman, A., Jeffries, C. and Ollis, D. L. (1999) Structure. Vol 6 141-146. Crystal structure of trehalose-6-phosphate phosphatase-related protein: biochemical and biological implications. Rao, K. N., Kumaran, D., Seetharaman, J., Bonanno, J. B., Burley, S. K., Swaminathan, S. (2006) Protein Sci. 15: 1735-1744. Insights on the evolution of trehalose biosynthesis. Avonce, N. Mendoza-Vargas, A., Morett, E. and Iturriaga, G. (2006) BMC Evolutionary Biology. 6, 109. A single Active Trehaolse-6P Synthase (TPS) and a Family of Putative Regulatory TPS-Like Proteins in *Arabidopsis*. Vandesteene, L., Ramon, M., Le Roy, K., Van Dijck, P. and Rolland, F. (2010) Molecular Plant. Vol 3, Number 2, 406-419. The X-ray crystallographic structure and specificity profile of HAD superfamily phosphohydrolase BT1666: Comparison of paralogous functions in *B. thetaiotaomicron*. Lu, Z., Dunaway-Mariano, D. and Allen, K. N. (2011) Proteins: Structure, Function and Bioinformatics. 79 (11) 3099-3107.

Method

From the literature the crystal structure of trehalose-6-phosphate phosphatase-related protein from *Thermoplasma acidophilum* was identified as the closest protein structure to homology model rice trehalose-6-phosphate phosphatase (T6PP). The protein structure database (PDB) accession code for this protein is 1U02. Please see, Crystal structure of trehalose-6-phosphate phosphatase-related protein: biochemical and biological implications Rao, R. N., et al. (2006) Protein Sci. 15: 1735-1744 and Uniprot code: Q9HIW7.

Initial Sequence Alignment

The T6PP sequences for; *Arabidopsis thaliana* (19925; SEQ ID NO: 14), *Arabidopsis thaliana* (19926; SEQ ID NO: 15), *Oryza sativa* (19924; SEQ ID NO: 16), and *Oryza sativa* (15777; OsT6PP-WT; SEQ ID NO: 2) were used for the alignment as well as SEQ ID NO: 4. These protein sequences together with the T6PP-related protein from *Thermoplasma acidophilum* (Q9HIW7) were aligned with Vector NTI using the ClustalW method to produce an initial alignment, please see FIGS. 1A to 1C. Initial protein sequence alignment of T6PP related protein (Q9HIW7) and the protein sequences for *Arabidopsis thaliana* (19925, SEQ ID NO: 14), *Arabidopsis thaliana* (19926; SEQ ID NO: 15), *Oryza sativa* (19924, SEQ ID NO: 16), and *Oryza sativa* (15777, SEQ ID NO: 2). The residues bolded and italicized in the protein sequence alignment below are important residues from the larger Halo Dehydrogenase superfamily that helped confirm the quality of the alignment.

The underlined residues in FIG. 1A to 1C are important residues that helped confirm the quality of the alignment. Most of these residues are catalytic residues (the residue numbers all refer to the residue numbers in the *Oryza sativa* 15777 OsT6PP-WT protein sequence): residue aspartic acid 121 forms a phosphoaspartate intermediate with the substrate. Threonine 318) (in the larger super family this residue can be a serine) hydrogen bonds to a phosphoryl oxygen in the substrate. Aspartic acids 315 and 123 coordinate the $Mg^{2+}$ ion with their side-chain and backbone carbonyl, respectively. Lysine 289 stabilizes the transition state of the reaction.

Preparation of 1U02 Protein Structure for Homology Modeling

The T6PP-related protein crystal structure (PDB code 1U02) was loaded into Maestro (Schrödinger, Inc.) and analyzed and prepared for use (adding protons, building disulfide bridges, setting metal charges, optimizing hydrogen bonds).

At the same time, the experimental electron density map for entry 1U02 was retrieved from the PDB and analyzed. While most features in the map had been modeled correctly in the deposited structure, the electron density at the position of the glycerol molecule close to the active site was inconsistent with the expected density features of glycerol. Instead, the map clearly revealed the presence of two water molecules at this position. Therefore, the glycerol molecule was removed from the model and two waters added at their correct positions. Before the homology modeling process started, all waters where removed from the structure except for the two water molecules directly coordinating the $Mg^{2+}$ ion at the active site.

This modeling issue in the work by Rao et al. had important consequences. Because the T6PP-related protein had been crystallized as an apoenzyme only and did not contain bound substrate, the authors had used the position of the glycerol molecule to guide their manual docking procedure. Essentially, the authors reasoned that the substrate would bind at the glycerol binding site because glycerol is somewhat similar in its properties to pyranoses. However, because there was no glycerol at the active site in the structure solved by Rao et al., their docking of T6P substrate into the apoenzyme was altered in the subsequent model.

Homology Modeling

The initial sequence alignment was read into PRIME (Schrödinger), along with the template protein structure. Upon closer analysis the protein sequence alignment was modified to optimize the loop insertion locations (insertions towards the external surface of the enzyme) and important residues from the literature. See the alignment (above) for the initial and the alignment (below) for the final protein sequence alignment.

Figure 7:
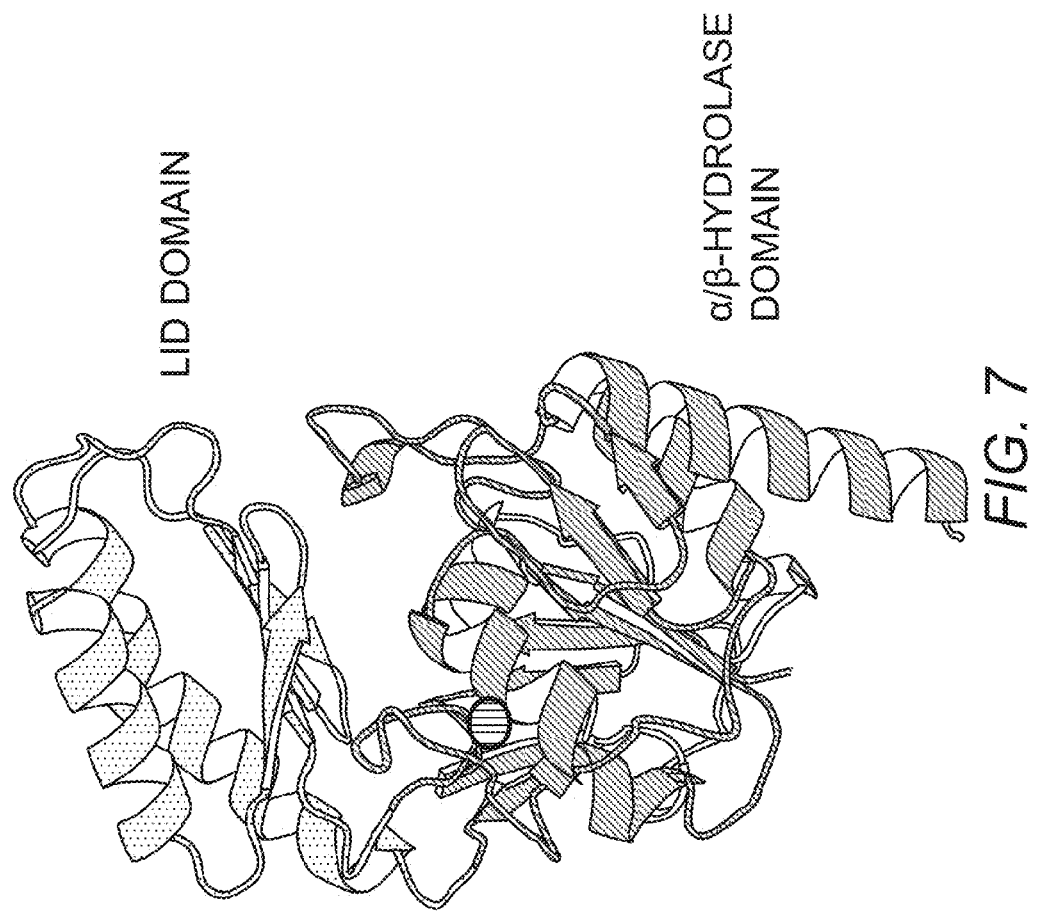
FIG. 7 shows the ribbon plot of the rice T6PP homology model. The enzyme contains two domains: an α/β-hydrolase domain and a smaller "lid domain". The active site lies at the top of the α/β-hydrolase domain (dot); the substrate binding cleft is in the interface between the two domains. The two domains are connected by a flexible linker, allowing the lid domain to open and close during catalysis. Because the template for homology modeling, the bacterial T6PP-related protein (PDB code 1U02), is an apoenzyme with an empty active site, it is likely that the relative orientation of the lid and hydrolase domains is slightly different in the actual enzyme-substrate complex.

The final alignment was used in PRIME to produce homology models of Oryza sativa 15777 and Oryza sativa 19924. These models were relaxed using energy minimization in MacroModel (Schrödinger), first for hydrogens, then including the protein side chains, finally including the protein backbone. The final model is shown in FIG. 7. The enzyme contains two domains: an α/β-hydrolase domain and a smaller "lid domain". The active site lies at the top of the α/β-hydrolase domain (dot); the substrate binding cleft is in the interface between the two domains. The two domains are connected by a flexible linker, allowing the lid domain to open and close during catalysis. Because the template for homology modeling, the bacterial T6PP-related protein (PDB code 1U02), is an apoenzyme with an empty active site, it is likely that the relative orientation of the lid and hydrolase domains is slightly different in the actual enzyme-substrate complex.

The final protein sequence alignment of T6PP related protein (Q9HIW7) and the protein sequences for *Arabidopsis thaliana* (19925), *Arabidopsis thaliana* (19926), *Oryza sativa* (19924), and *Oryza sativa* (15777) can be seen in FIGS. 11A to 11C. The alignment was optimized using the literature and analyzing the protein structure scaffold. The residues in bold and italicized in the protein sequence alignment below are important residues from the larger Halo Dehydrogenase superfamily that helped confirm the quality of the alignment.

As described above, the position of T6P as reported Rao et al. had been based on a flawed premise and could not be used as a starting point for rational design of T6PP mutants. Instead, we decided to dock the T6P into the homology model by hand in a stepwise approach, following mechanistic considerations and taking biochemical data into account.

The initial starting point was based on the fact that one of the negatively charged oxygen atoms of the 6-phosphate group must be coordinated to the catalytic $Mg^{2+}$ ion in the active site. This is a requirement of the catalytic mechanism and a general feature of HAD family phosphatases (Please see, "The X-ray crystallographic structure and specificity profile of HAD superfamily phosphohydrolase BT1666: Comparison of paralogous functions in *B. thetaiotaomicron*." Lu, Z., Dunaway-Mariano, D. and Allen, K. N. (2011) Proteins: Structure, Function and Bioinformatics. 79 (11): 3099-3107). At the same time, the phosphate oxygen must be in close proximity to Asp121, which accepts the phosphate group and forms a transient phosphor-aspartate intermediate during catalysis. Placing the phosphate oxygen at the equatorial position in the octahedral $Mg^{2+}$ coordination sphere satisfied both requirements. This interaction anchors the T6P molecule to the protein, and was used to guide the docking process.

Figure 8:
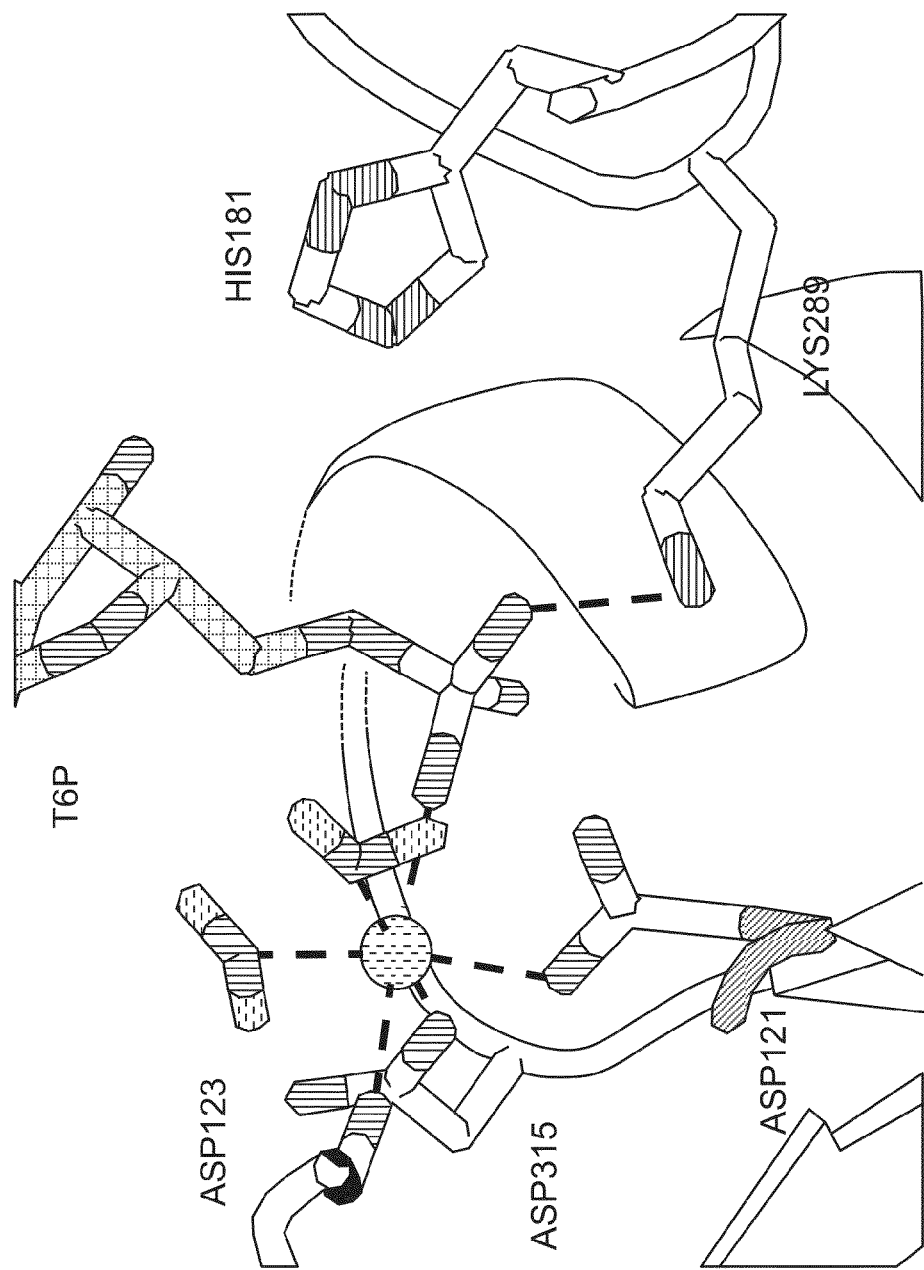
FIG. 8 shows the placement of the 6-phosphate group of T6P. One of the oxygen atoms of the 6-phosphate group sits in an equatorial position in the $Mg^{2+}$ coordination sphere. Asp121, which accepts the phosphate group during catalysis to form a covalent intermediate, assumes an axial position. Lys289 is directly hydrogen bonded to the phosphate group and His181 is in close proximity. Both residues are ideally positioned to stabilize the developing negative charge on the phosphate moiety during catalysis.

Following the initial placement of the phosphate oxygen in the Mg coordination sphere, it became clear that there was only one orientation of the 6-phosphate group that allowed the phosphoester oxygen to point towards the active site cleft, rather than clashing with the residues surrounding the active site. In this orientation, one of the other phosphate oxygen forms a hydrogen bond with Lys289, which would allow the lysine to stabilize the developing negative charge on the phosphate group during catalysis (FIG. 8). One of the oxygen atoms of the 6-phosphate group sits in an equatorial position in the $Mg^{2+}$ coordination sphere. Asp121, which accepts the phosphate group during catalysis to form a covalent intermediate, assumes an axial position. Lys289 is directly hydrogen bonded to the phosphate group and His181 is in close proximity. Both residues are ideally positioned to stabilize the developing negative charge on the phosphate moiety during catalysis. The rice T6PP homology model is shown in green stick representation, the T6P substrate in yellow.

Figure 9:
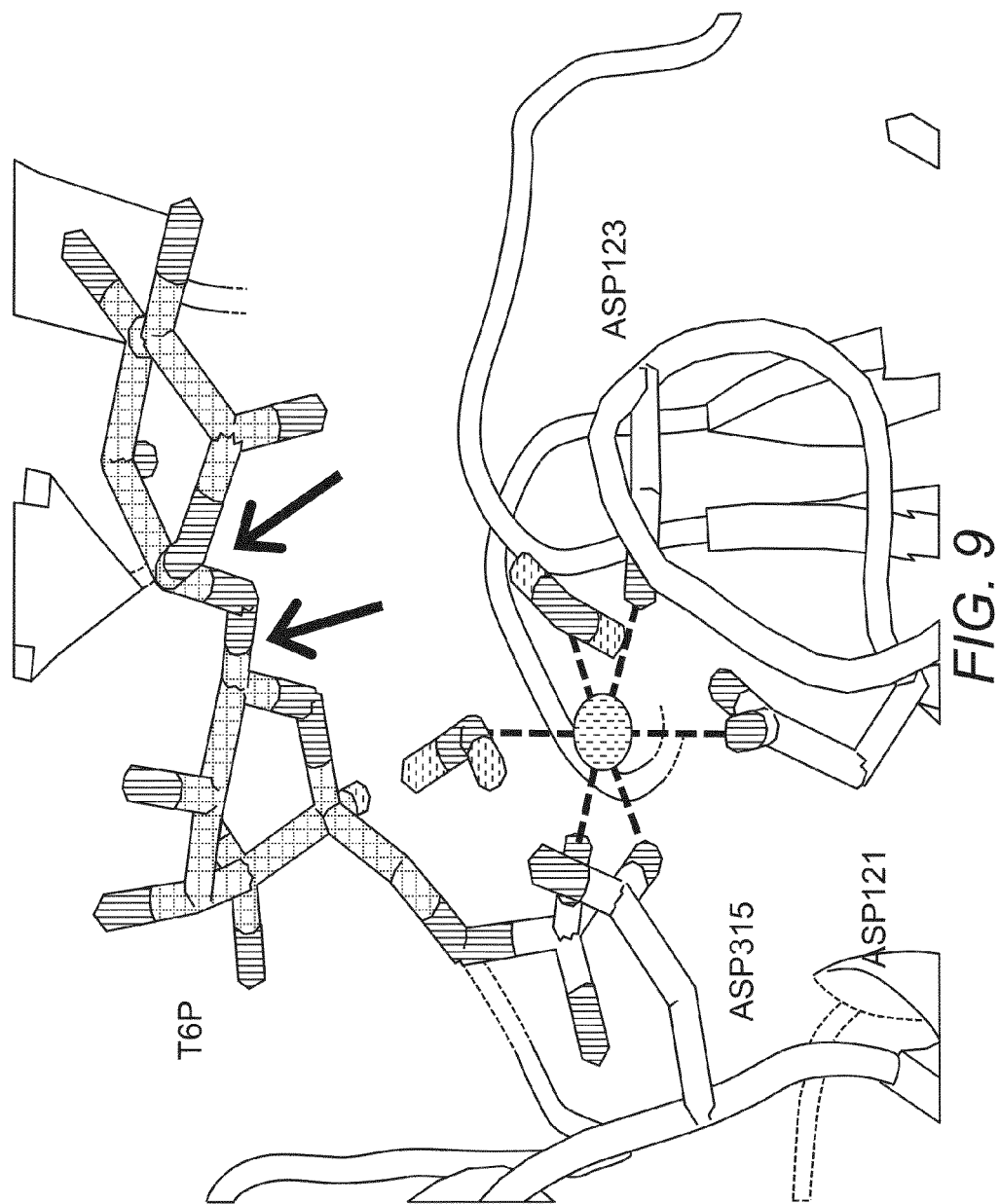
FIG. 9 shows the rotatable bonds in the T6P substrate. While the position and orientation of the pyranose ring closest to the 6-phosphate group are well determined by the anchored phosphate group, there is considerable flexibility between the first and second rings due to the presence of two rotatable glycosidic bonds (arrows). A range of possible positions for the second ring was obtained by rotating the two bonds. Conformations in which the second ring clashed with the protein were discarded.

With both the position and the orientation of the 6-phosphate group clearly defined, the substrate was then minimized in the active site using MacroModel (Schrödinger) with the protein kept rigid. Finally, the two rotatable bonds between the pyranose rings were scanned using Maestro (Schrödinger) and the resulting conformers visually inspected to identify possible interactions with the protein (FIG. 9). Several conformations were identified in which the second pyranose ring was in a reasonably good position to form contacts with the protein. In the end, a conformer in which the second ring was roughly equidistant from the residues on the lid domain was chosen as the most likely one, and used for subsequent analyses.

While the position and orientation of the pyranose ring closest to the 6-phosphate group are well determined by the anchored phosphate group, there is considerable flexibility between the first and second rings due to the presence of two rotatable glycosidic bonds (blue arrows). A range of possible positions for the second ring was obtained by rotating the two bonds. Conformations in which the second ring clashed with the protein were discarded.

OsT6PP Variants Design

Point mutations were designed that would reduce or completely abolish the catalytic activity of rice T6PP (OsT6PP-WT). In general terms, the planned mutants fell into three classes, spanning the range from near-wild type activity to totally inactive:

Mutation of key catalytic residues based on the enzyme mechanism. Mutations in this class are expected to have severe effects on catalytic activity ("severe mutants").

Mutation of residues involved in substrate binding and recognition. Mutations in this class would be expected to reduce turnover and/or alter substrate specificity, but not completely abolish catalytic activity. Identifying these residues requires a good estimate of where the substrate is located in the active site cleft ("mild mutants").

Control mutations. Mutations in this class are predicted to have a very mild effect on catalytic activity because they are far away from the substrate binding site and should not affect protein stability ("very mild mutants").

For all three classes, the following design rules were employed to ensure that the observed activity in the mutants was due to the specific changes made to the protein, and not just a consequence of general destabilization:

If the residue in question is hydrophobic and suspected to form a nonpolar interaction with the substrate, retain the hydrophobic character of the residue and increase bulk. This should lead to a steric clash with the substrate and lower the binding affinity.

If the residue has hydrogen bonding capacity (either as donor or acceptor) that would allow it to interact with one of the pyranose hydroxyl groups, either shorten the residue while retaining the hydrogen bonding capacity, or keep the length roughly the same and remove hydrogen bonding capacity.

No modification of residues suspected of forming interdomain salt bridges. In the T6PP-related protein, there are a number of salt bridges formed by a positively charged residue on the lid domain and a negatively charged one on the α/β-hydrolase domain, and vice versa. Mutating these residues would possibly destabilize the protein without specifically changing substrate affinity or catalytic activity.

No charge reversals: positively charged residues should not be mutated to negatively charged ones (and vice versa), but rather to a neutral residue. Charge reversal mutants are known to cause local destabilization of protein structure and are thus to be avoided.

Because of the uncertainty in the location of the second pyranose ring, and the fact that the relative orientation of the lid and α/β-hydrolase domains might change upon substrate binding (see FIG. 4), we considered residues up to 10 Å away from the modeled T6P substrate. Working in concentric shells outward from the substrate, we analyzed the residues surrounding the substrate and considered them for mutation following the rules described above.

List of T6PP point mutations designed to reduce its trehalose 6-phosphate phosphatase activity Severe Mutants D315N: Asp315 is one of the two Asp residues at the active site that chelate the catalytic $Mg^{2+}$ ion (FIG. 5). Replacing it with the isosteric asparagine will remove its $Mg^{2+}$ binding capability and lead to a total loss of activity.

K289A: Lys289 likely forms a hydrogen bond with the 6-phosphate group of T6P and serves to stabilize the developing negative charge during catalysis (FIG. 5). Replacing it with Ala should significantly slow down the reaction to near inactivity.

H181A: His181 is in close proximity to the 6-phosphate group of T6P and probably serves as the general acid during catalysis. Mutation to Ala will remove the general acid and slow down catalysis to near inactivity.

T318V: Thr318 is a conserved residue in the HAD superfamily (Lu et al. 2011) and forms a hydrogen bond with the 6-phosphate group. Replacing it with the small unpolar residue valine removes the hydrogen bonding capacity and makes binding of a highly charged group unfavorable. This mutation is expected to lead to a near-total loss of activity.

Mild Mutants

S159A: Ser159 is 5.8 Å away from the substrate and might be involved in hydrogen bonding interactions with the substrate, either as donor or acceptor. Replacing it with alanine will abolish hydrogen bonding and decrease substrate affinity.

E235D: Glu235 is in the lid domain and 10.6 Å away from the substrate. It is likely to function as a hydrogen bond donor; replacing it with aspartate will retain its hydrogen bonding properties but increase the distance to the substrate, resulting in non-ideal hydrogen bonding geometry and reduced substrate affinity.

S242D, S242E: Ser242 is in the lid domain and 8.2 Å away from the substrate. It is expected to form hydrogen-bonding interactions with the substrate, and replacement with aspartate or glutamate will retain the polar character and hydrogen bonding capability, but lead to a steric clash with the substrate because aspartate and glutamate have longer side chains.

T273E, T273V: Thr273 is only 4 Å from the substrate and could be involved in a polar interaction via the hydroxyl group, or a nonpolar interaction with the side of a pyranose residue. If the interaction is polar, then both the glutamate mutation (steric crowding) and the valine mutation (removal of the polar group and loss of hydrogen bonding capability) will lead to decreased activity. If the interaction is nonpolar, then only the first mutation will lead to a loss of activity, while the second should be neutral in effect.

V278F, V278M: Val278 is 3.4 Å away from the substrate and likely to form a nonpolar interaction with the face of a pyranose ring. Mutation to either phenylalanine or methionine will retain the hydrophobic character of the side chain, but lead to a severe steric clash with the substrate and reduced activity.

E280A: Glu280 is in the lid domain and 6.7 Å away from the substrate. It likely serves as a hydrogen bond acceptor, and mutating it to alanine would abolish its hydrogen bonding capability and reduce substrate binding.

D316H: Asp316 is in the hydrolase domain and in close proximity to the substrate, but may be involved in a salt bridge with R276 and not in substrate binding. Replacement with histidine would remove its negative charge and break the salt bridge, which should only have mild effects. However, if Asp316 is involved in substrate binding by accepting a hydrogen bond then the effect on catalytic activity should be severe.

I129A, I129N: Ile129 is in close proximity to the first pyranose ring and possibly forms a nonpolar interaction with the substrate. Both mutations would be expected to lead to reduced activity, the first because of the removal of hydrophobic interactions, the second because of the introduction of a polar function.

H244S: His244 lies in the lid domain about 10 Å away from the substrate. The H244D mutation was already known to have strongly reduced catalytic activity, which could either be due to loss of substrate binding via the histidine, or due to an indirect effect of the charge reversal on adjacent residues that might be involved in substrate binding themselves. The serine mutation was designed to test whether His244 is directly involved in substrate binding. If it is, then shortening of the side chain while keeping its polar character should lead to a decrease in substrate binding.

Very Mild/Control Mutants

R276A: Arg276 is situated on the lid domain and might be involved in substrate binding, but it is probably pointing away from the substrate and may also be involved in a salt bridge with Asp316 on the hydrolase domain. Replacement with alanine is expected to have only mild effects.

V293A: Val 293 is 6 Å away from the substrate, but facing outwards toward bulk solvent and unlikely to have any role in substrate binding. The alanine mutation is a very conservative one and not expected to have any effect.

Based on the above strategy 22 OsT6PP variants were designed and are described in the Table below.

| Residue | Dist. (Å) | Role | Mutate to | |
|---|---|---|---|---|
| Ser159 | 5.8 | Possible substrate binding | Ala | cT6PP- Var1 |
| His181 | 3.0 | Catalysis - stabilizes charge | Ala | cT6PP- Var2 |

-continued

| Residue | Dist. (Å) | Role | Mutate to | |
|---|---|---|---|---|
| Glu235 | 10.6 | Possible substrate binding | Asp | cT6PP- Var3 |
| Ser242 | 8.0 | Possible substrate binding | Asp | cT6PP- Var4 |
| Ser242 | 8.0 | Possible substrate binding | Glu | cT6PP- Var5 |
| Thr273 | 4.0 | Possible substrate binding | Val | cT6PP- Var6 |
| Thr273 | 4.0 | Possible substrate binding | Glu | cT6PP- Var7 |
| Arg276 | 2.5 | Substrate binding | Ala | cT6PP- Var8 |
| Val278 | 3.4 | Substrate binding | Met | cT6PP- Var9 |
| Val278 | 3.4 | Substrate binding | Phe | cT6PP- Var10 |
| Glu280 | 6.7 | Substrate binding | Ala | cT6PP- Var11 |
| Lys289 | 1.9 | Catalysis - stabilizes charge | Ala | cT6PP- Var12 |
| Val293 | 6.1 | Control | Ala | cT6PP- Var13 |
| Asp315 | 2.5 | Mg chelation | Asn | cT6PP- Var14 |
| Asp316 | 1.4 | possible Salt bridge to Arg276 | His | cT6PP- Var15 |
| Thr318 | 2.3 | 6-Phosphate binding | Val | cT6PP- Var16 |
| Ile129 | | Possible substrate binding | Ala | cT6PP- Var17 |
| Ile129 | | Possible substrate binding | Asn | cT6PP- Var18 |
| His244 | | Inactivates catalysis | Ser | cT6PP- Var19 |
| Ala102 | | Outside catalytic domains based on protein modeling | Val | cT6PP- Var20 |
| D56 N-terminal | | Possible regulatory role | 56 aa truncation | cT6PP- Var21 |
| D110 N-terminal | | Possible regulatory role | 110 aa trucation | cT6PP- Var21 |

For the residue numbering in this table please refer to the residue numbers in the *Oryza sativa* 15777 OsT6PP-WT protein sequence. The variants Δ56 N-terminal and Δ110 N-terminal with N-terminal truncation of 56 and 110 amino acids, respectively, were design to test the possible regulatory role of this portion of the protein molecule. As apparent in the alignments above this 110 N-terminal portion of the T6PP is unique to plant T6PPs and may not be essential for phosphatase catalysis as based on modeling of the active site residues.

Vector Construction & *E. Coli* Transformation

Coding sequence of the T6PP variants were synthesized and cloned into the *E. coli* expression vector pGEX-6P_3 for expression as GST-fusion protein: GST being at N-terminal end of the T6PP protein. The nucleotide sequences of the inserted DNAs in the vector were sequenced and confirmed.

The plasmids for expression of the OsT6PP variants were transformed into *E. coli* BL21 (DE3) pLysS cells based on Invitrogen® protocol for recombinant protein expression. Briefly, thawed *E. coli* cells on ice and 10 ng (in 10 μL) of each plasmid DNA were added to the cells and mixed gently by tapping. Tubes were kept on ice for 15 min and heat shocked for 30 sec at 42° C. in water bath. Tubes were kept on ice after heat shock. 250 μL of SOC was added in each tube and incubated, with shaking, for 1 hour at 37° C. 50 μL of the transformation reaction was platted onto LB plates containing ampicillin (50 μg/mL) and chloramphenicol (34 μg/mL). The plates were inverted and incubated overnight at 37° C.

Expression and Partial Purification Recombinant OsT6PP and its Variants

*E. coli* cells [BL21(DE3)pLysS] harboring vector to recombinant T6PP variant expression were grown to an $A_{600nm}$ of 0.6 in Luria Broth medium containing 50 μg/ml ampicillin and 25 μg/ml chloramphenicol. Expression of recombinant protein was induced by the addition of 0.5 mM IPTG for 2 h at 37° C. Cells were harvested at 6000×g (JA rotor) or 3000 rpm in Allegra 6R centrifuge. Cell pellets were re-suspended in buffer (20 mM Tris-HCl, pH 7.5, 150 mM NaCl, protease inhibitor (GE Healthcare®) 1 tablet per 50 mL buffer, 2 μL DNase 1/mL of buffer). Cells were disrupted by sonication (10 cycles of 10 sec on −30 sec off, output power set up at 3.5 (18 Watts). Tubes were kept on ice during sonication. Lysates were centrifuged at 15,000×g for 15 minutes. Supernatants were transferred into 15 ml falcon tubes and kept on ice before adding Glutathione Sepharose® 4B beads (Thermo Scientific®).

Glutathione Sepharose 4B beads were pre-equilibrated 3 times with wash buffer (20 mM Tris-HCl, pH 7.5, 150 mM NaCl, 1 mM DDT). 250 μL of pre-equilibrated beads were added in each lysate (7 ml) tube and incubated for 1:30 h at 4 under slow rocking. Glutathione Sepharose 4B beads containing lysates were transferred into poly-prep chromatography columns (10 ml BioRad®) and the soup was allowed to completely drain. Protein bound resin was washed with wash buffer (3 times, 5 ml each) followed by wash (5 mL, 3×) with PreScission® cleavage buffer (20 mM tris-HCl, pH 7.0, 150 mM NaCl and 1 mM DTT). PreScission protease enzyme (10 μL in 300 μL buffer) was added to the protein bound beads, and incubated for 16 h at 4° C. with slow rocking. Supernatant was collected and re-cycled 3 times through the column and the final collection was kept on ice for running gel and measuring the concentration.

Protein concentration was measured using BCA kits [Thermo Scientific®]. 20 μL of each stock protein mixed with 4×SDS dye and SDS-PAGE (4-12% gradient gel) was run using MOPS buffer at 200 volts to assess enrichment and ensure integrity of the purified protein. The final percent purity of partially purified T6PP and its variants was determined using Bio-Rad Experion® automated electrophoresis.

Activity of OsT6PP and its Mutants

The activity of OsT6PP and its variants was measured based on a standard assay protocol. Briefly, an appropriate amount of protein was made from the stock and kept in 96 well plates. Reaction mixtures (buffer with 2 mM T6P final concentration in the reaction mixture; buffer composition, 10 mM Tris pH 6.7, 2 mM $MgCl_2$ and 0.5 mg/mL BSA) were made and kept on ice before mixing with enzyme preparation. Appropriate amount of diluted enzyme protein was added to the reaction mixtures (protein concentration of 0.05, 0.1 or 1 μg in total 100 μL reaction volume was used) in 96 well plate. Reaction mixtures were incubated at 37° C. for different time intervals (5, 10 and 20 minutes) and the enzyme in the reaction mixture was deactivated by heating at 95° C. for 5 minutes. The inactivated reactions in the 96 well plate was centrifuged for 1 minute at 700 rpm, then 80 μL of each reaction solution transferred into wells containing 80 μL water. The mixtures were transferred into the wells of a MicroScreen-HV plate for filtration and a Dionex 96 well plate was used to collect the filtrate for HPLC analysis. The specific activity was calculated based on standard procedure.

Dionex HPLC

Dionex ICS-3000 Ion Chromotography System was used for the detection of trehalose product formed by the dephosphorylation of T6P substrate in the presence of T6PP enzyme. Trehalose was separated using by a CarboPac® PA1 analytical column with a 15 minutes elution gradient at a flow rate of 1 mL/min. The samples were injected into the CarboPac PA1 column equilibrated with 100 mM NaOH at a flow rate of 1 ml/min followed by a 0-200 mM sodium acetate gradient in 100 mM NaOH from 3 to 8 mM, then 200 mM to 750 mM sodium acetate gradient in 100 mM NaOH from 8 to 10 mM and back to 100 mM NaOH from 10.5 to 15 min). The trehalose resolved by the chromatography was quantified by integrating the peak area using the Chromeleon® software.

Data Plot and Estimation of Specific Activities of the T6PP Variants The assay reactions were incubated for three different time intervals and each data point in the plot is the average of three independent assay reactions. Background amount (trehalose formation in the absence of enzyme, negative control) was monitored and was subtracted from the trehalose produced in the assay mixture with added enzyme. The plotted data was fitted with polynomial equation ($Y=AX^2+bX$). The rate of reaction was estimated from the slope ($2AX+b$) of the above equation at 1 minute.

Reaction rate=produced trehalose (μM)/min and converted to μmol/min

Specific activity=rate of trehalose formation (μmol/min)/mg of T6PP.

Comparison of the trehalose 6-phosphate phosphatase activities of the T6PP variants as determined by the assay procedure described above.

| T6PP Variants | Specific Activity μmol of Tre/min/mg T6PP | Relative Activity % with respect to OsT6PP-WT |
| --- | --- | --- |
| #23, OsT6PP-02 | 42.36 | 215.3 |
| #21, OsT6PP-Δ56 N-Terminal | 25.59 | 130.0 |
| #25, AtT6PP-B | 20.00 | 101.6 |
| #28, OsT6PP-WT | 19.68 | 100.0 |
| #20, OsT6PP-A102V | 17.87 | 90.8 |
| #08, OsT6PP-R276A | 15.27 | 77.6 |
| #07, OsT6PP-T273E | 12.36 | 62.8 |
| #06, OsT6PP-T273V | 12.12 | 61.6 |
| #27, EcTPS-T6PP | 10.58 | 53.7 |
| #24, AtT6PP-A | 6.31 | 32.1 |
| #26, ScT6PP (TPS-2) | 5.50 | 28.0 |
| #03, OsT6PP-E235D | 5.31 | 27.0 |
| #16, OsT6PP-T318V | 3.91 | 19.9 |
| #13, OsT6PP-V293A | 2.49 | 12.6 |
| #30, OsT6PP-I129F, A102V | 1.70 | 8.7 |
| #17, OsT6PP-I129A | 1.58 | 8.0 |
| #09, OsT6PP-V278M | 1.29 | 6.5 |
| #18, OsT6PP-I129N | 1.24 | 6.3 |
| #19, OsT6PP-H244S | 0.45 | 2.3 |
| #04, OsT6PP-S242D | 0.40 | 2.0 |
| #15, OsT6PP-D316H | 0.36 | 1.8 |
| #10, OsT6PP-V278F | 0.12 | 0.6 |
| #01, OsT6PP-S159A | 0.07 | 0.4 |
| #14, OsT6PP-D315N | 0.07 | 0.4 |
| #05, OsT6PP-S242E | 0.06 | 0.3 |
| #11, OsT6PP-E280A | 0.05 | 0.3 |
| #29, OsT6PP-H244D | 0.02 | 0.1 |
| #02, OsT6PP-H181A | 0.01 | 0.1 |
| #12, OsT6PP-K289A | 0.00 | 0.0 |
| #22, OsT6PP-Δ110 N-terminal | not determined | |

[OsT6PP-02, *Oryza sativa* T6PP-02; AtT6PP-A, *Arabidopsis thaliana* T6PP-A; AtT6PP-B, *Arabidopsis thaliana* T6PP-A; EcTPS-T6PP, *Escherichia coli* Trehalose 6-phosphate synthase & phosphatase fusion protein and ScT6PP[TPS-2], *Saccharomyces cerevisiae*, Trehalose 6-phosphate phosphatase]

Example 7

In Vitro Evaluation of Possible Protein-Protein Interactions Between T6PP and TPS and Further Evaluation of Downstream Effects A yeast model system will be developed to evaluate whether or not a T6PP from rice can interact with various components of a yeast TPS-complex. Vandercammen et. al. (Eur. J. Biochem. 182, 613-620 (1989)) discovered through co-purification of TPS and T6PP from *Saccharomyces cerevisiae* that the proteins are part of a single bifunctional protein. Bell et. al. (The Journal of Biological Chem. 273; No. 50, pp 33311-33319 (1998)) further describes the composition and functional analysis of a T6PP/TPS complex in *Saccharomyces cerevisiae*. It was further shown that a yeast TPS can form a complex with a T6PP derived from *Arabidopsis* (see Vogel et. al. The Plant Journal 13; No. 5, pp. 673-683). The yeast TPS complex comprises four units TPS1, TPS2, TPS3 and TSL1. TPS1 comprises a protein domain having TPS activity and TPS2 comprises a protein domain having T6PP activity. TPS3 and TSL1 both function in the regulation of the TPS complex function. Not to be limited by theory, it is contemplated that by developing a yeast model, one may evaluate further modifications in vitro that could be used to develop proteins, peptides, polypeptides or chemicals that could increase the production of T6P thus modulating the flow of sugars into the reproductive tissues and/or initiating various other cascades which confer increased yield and/or stress in a plant when expressed or applied to a plant. The objective of the method is to: (A) test whether or not a rice T6PP can interact with the various components of a yeast TPS complex and further measure how these interactions effect the catalytic activities of each component by measuring downstream products (i.e. trehalose, T6P); (B) develop a in vitro assay to test if the rice T6PP interacts with a rice TPS; (C) express a modified rice T6PP in maize to isolate and characterize a resultant T6PP/TPS complex (D) use the data obtained from (A) (B) and/or (C) to carry out bioinformatics analysis to identify further modifications that can be made to a T6PP molecule to further facilitate the production of T6P. It is also envisioned that nucleotides encoding the complex itself can be developed from the data collected from the experiments mentioned.

Evaluation of the Interaction of Rice T6PPs with TAP-Tagged TPS-Complex Components from Yeast Expression vectors will be separately constructed for expression in either yeast or *e. coli* comprising a polynucleotide sequence encoding the unmodified T6PP protein as depicted in SEQ ID NO: 2 and a modified T6PP protein as depicted in SEQ ID NO: 6. A construct may also be developed for other modified T6PPs to evaluate various effects of mutations for example a nucleotide sequence encoding a T6PP such as depicted in SEQ ID NO: 4 or any other T6PP that has been modified to have lower activity. These constructs can then be transformed into both bacteria and yeast for further evaluation.

The Table below identifies various publically available strains of yeast having TAP tagged proteins that may be used to evaluate interactions between the expressed rice T6PPs and various components of the yeast TPS complex. TAP tagged yeast strains may be purchased from a vendor such as Thermo Scientific. TAP tagged proteins may be easily detected on a Western Blot as is well known in the art. To determine whether or not the rice T6PP variants (wild type and modified) interact with any component of the yeast TPS complex, extracts comprising both the rice T6PP protein and relative TAP tagged yeast TPS complex protein components can be made. Proteins can next be extracted from these extracts and Western Blots carried out to determine whether or not a protein-protein interaction is occurring between any of the modified rice T6PPs and the yeast TPS-complex components (i.e. protein-protein interaction will be indicated by a larger than expected band size) via TAP antibody detection. The following table describes trains of yeast comprising TAP tagged proteins which can be detected by Western Blot analysis using TAP antibody.

| 1 | YSC1178 | TAP Tagged ORF Clone YSC1178-7499322 | TPS1 |
| 2 | YSC1178 | TAP Tagged ORF Clone YSC1178-7499771 | TPS2 |
| 3 | YSC1178 | TAP Tagged ORF Clone YSC1178-7502275 | TPS3 |
| 4 | YSC1178 | TAP Tagged ORF Clone YSC1178-7502052 | TSL1 |

After the identification of protein-protein interactions between rice T6PPs and yeast TPS complex components, experiments will be conducted to determine the various effects modified and unmodified T6PPs have on the yeast TPS complex function. The yeast TPS2 component (i.e. the portion having T6PP activity) of the TPS complex will be substituted with either a unmodified rice T6PP protein (SEQ ID NO: 1) or with modified rice T6PP proteins (SEQ ID NOs: 3, 5, 7). These modified complexes can then be expressed in yeast to further evaluate how these substitutions effect the overall function of the TPS complex through the measurement of T6P and Trehalose levels. T6P levels and Trehalose levels can be measured using standard HPLC methods known in the art from yeast extracts to determine the various effects of each substitution. In theory it is believed that complexes comprising the modified rice T6PP will show an increase in T6P levels as compared to the complex comprising the rice unmodified T6PP.

Example 8

Evaluation of Modified T6PP Proteins in Plant Tissue Via Transient Plant Expression Transient plant assays will be used to further evaluate the effects modified T6PPs (i.e. T6PPs modified for decreased activity) have on T6P and trehalose production in plant tissue. A transient plant assay method as described in U.S. application for patent 2010/0319089, herein incorporated by reference, may be used to evaluate various T6PPs and their effect on T6P and trehalose production. Generally, binary constructs comprising modified T6PPs such as those depicted in SEQ ID NOs 2, 4 or 6 will be infiltrated and transiently expressed essentially as described in U.S. 2010/0319089. Following transient expression of the modified T6PPs, T6P and trehalose levels will be monitored over a multi-day (i.e. 1-10 days) time frame using HPLC. Additionally various TPS/T6PP complexes may be constructed and evaluated by transiently expressing each relative complex in a plant tissue.

Yeast Two Hybrid Screening: In addition, mammalian or yeast two-hybrid approaches (see, e.g., Bartel, P. L. et. al. *Methods Enzymol*, 254:241 (1995)) can be used to identify polypeptides or other molecules that interact or bind when expressed together in a cell. A yeast two hybrid screen may be carried out to further identify and characterize any protein-protein interactions occurring between modified T6PP proteins and endogenous plant proteins.

Example 9

Yield Component Analysis of Plants Expressing Modified T6PP Proteins

Flowering drought stress decreases yield by increasing barrenness, decreasing ears per plant and kernels per plant. Therefore, transgenic maize plants expressing the modified protein found in SEQ ID NO: 4 under the OsMADS6 promoter were tested in two field locations under four different stress treatments, 1) well watered with no yield loss due to drought stress, 2) mild stress, 30-45% targeted yield loss of control plant due to drought stress during flowering, 3) moderate stress, 60% targeted yield loss of control plant due to drought stress during flowering and 3) severe stress, 80% targeted yield loss of control plant due to drought stress during flowering. Data were collected on the number of plants per acre, kernel row number per ear, ears per plant, kernels per plant and weight per kernel. Eight different hybrids were tested.

All transgenic and control plants were tested in adjacent paired plots in the field. Pairs of plots with stands less than 50 plants were excluded. Differences were computed for each of the traits. Probabilities were computed using the paired t-test for individual hybrids within each trial in each location and for yield-loss groups for each variety. Four of the eight hybrids tested showed a positive yield response in severe flowering drought stress environment. Two hybrids showed a negative yield response. The yield increase in the four hybrids was consistently driven by an increase in the number ears per plant and the number of kernels per plant. Two of the four hybrids also showed a decrease in barrenness. The presence of the modified T6PP protein helped to mitigate the effect of a flowering drought stress by reducing barrenness, increasing ears per plant and increasing kernels per plant.

Example 10

In Vitro Activation of OsT6PP-WT in the Presence of OsT6PP-H244D

Increased Trehalose-6-Phosphate Phosphatase Activity (In Vitro) of OsT6PP-WT in the Presence of its Catalytically Inefficient Variant, OsT6PP-H244D (SEQ ID NO: 4)

Effect of added OsT6PP-H244D on the catalytic property of OsT6PP-WT was measured using the trehalose 6-phosphate phosphatase activity assay described above in Example 6. Briefly, appropriate amount (as indicated in the Table legends) of proteins (OsT6PP-WT & OsT6PP-H244D), partially purified from *E. coli* expressing the recombinant OsT6PP variants, were incubated on ice for 10 minutes in 96-well plates. Trehalose 6-phosphate substrate (final concentration 2 mM) was mixed in reaction buffer (buffer composition, 10 mM Tris pH 7.0 and 2 mM $MgCl_2$) and kept on ice before mixing with enzyme. 85 µL of reaction mixtures were added to the enzyme mixtures (100 µL total reaction volume) in 96-well plate. Reaction mixtures were incubated at 37° C. for different time intervals (as indicated in the Table legends. Each reaction was done in triplicate. The enzyme in the reaction mixture was deactivated by heating at 95° C. for 5 minutes. The inactive reaction mixtures in 96 well plate was centrifuged for 2 minutes at 700 rpm, then 80 µL of each reaction solution transferred into wells containing 80 µL water. The mixtures were transferred into the wells of a MicroScreen-HV plate for filtration and the filtrate was collected for HPLC analysis and estimation of trehalose form by the phosphatase reaction.

TABLE

Increased trehalose 6-phosphate phosphatase activity of OsT6PP-WT observed in the presence of OsT6PP variant, OsT6PP-H244D. Amount of trehalose (mM) formed in the reaction mixture due to dephosphorylation of trehalose 6-phosphate, when incubated (incubation time - column 1) with OsT6PP-WT ((1 µg/ml; column 2), OsT6PP-H244D (10 µg/ml; column 3) or mixture (column 4) of OsT6PP-WT (1 µg/ml) and OsT6PP-H244D (10 µg/ml).

| Time (min) | OsT6PP-WT | OsT6PP-H244D | OsT6PP WT + H244D | stdv WT | stdv H244D | stdv WT + H244D |
|---|---|---|---|---|---|---|
|  | Trehalose formed (µM) | | | | | |
| 0 | 0 | 0 | 0 | 0 | 0 | 0 |
| 20 | 25.3 | 1.1 | 89.5 | 1.6 | 0.6 | 1.9 |
| 40 | 33.6 | 4.6 | 155.0 | 4.7 | 0.2 | 3.8 |
| 60 | 36.8 | 5.9 | 220.1 | 4.4 | 0.8 | 8.3 | stdv—standard deviation calculated from triplicate data set for each reaction.

TABLE

Effect of OsT6PP-H244D concentration on activation of OsT6PP-WT's trehalose 6-phosphate phosphatase activity.

| OsT6PP-H244D µg/mL | T6PP activity Trehalose formed (µM) | |
|---|---|---|
| 0 | 28.7 | 0.0 |
| 0.5 | 34.9 | nd |
| 1 | 40.1 | nd |
| 2 | 52.3 | nd |
| 5 | 71.7 | nd |
| 10 | 77.7 | 2.2 |
| 20 | 101.1 | 6.2 |

T6PP activity was averaged from triplicate data set for each reaction,
nd—not determined
Amount of trehalose (µM, column 2) formed in the reaction mixture due to dephosphorylation of trehalose 6-phosphate, when OsT6PP-WT (1 µg/ml) is incubated with indicated concentration of OsT6PP-H244D (column 1). Amount of trehalose (µM, column 3) formed in when OsT6PP-H244D alone is incubated in the reaction mixture, in the absence OsT6PP-WT, at concentration indicated in column 1. The reactions were carried out for 20 minutes.

Increased trehalose 6-phosphate phosphatase activity (in vitro) of OsT6PP-WT is observed in the presence of its catalytically inefficient variants, including OsT6PP-H244D, OsT6PP-H244S and OsT6PP-S242E. The observed activation of T6PP in presence of OsT6PP-H244D is dependent on the concentration of OsT6PP-H244D in the reaction mixture. The extent of T6PP activation varied among the T6PP variants tested. The charge on the amino acid residues in the vicinity of 244-242 may be involved in this allosteric interaction. An approximately 3-fold increased T6PP activity was observed when OsT6PP-WT was assayed in presence of OsT6PP-H244D. In comparison a 1.7 fold increase in T6PP activity was observed when N-terminal truncated OsT6PP-D56NT was mixed with OsT6PP-H244D. This may indicate possible role of the N-terminal portion of the OsT6PP in the allosteric interaction.

Example 11

Expression of Modified T6PP in Wheat

Five constructs (see table below) of OsT6PP variants were transformed into wheat via an *Agrobacterium* transformation protocol (WO11013764) using a PMI selectable marker system (U.S. Pat. No. 5,767,378; U.S. Pat. No. 5,994,629) to generate stable transgenic events for trait evaluation. Three OsT6PP variants: OsT6PP, wild type sequence; OsT6PP-H244D (SEQ ID NO: 3) with a single modification at H244D and OsT6PP-I129F (SEQ ID NO: 5) with two modifications at A102V and I129F. In these five constructs, 20569 and 20833 were designed using +enhancers, to attempt to vary the level of OsT6PP expression and to target different tissues in plants, compared with 20571 and 20832 without enhancers. 12194 served as the wild type control for comparison to the T6PP variants.

TABLE

T6PP constructs used in wheat transformation

| Construct | Construct description | Gene of Interest |
|---|---|---|
| 20571 | prOsMADS6:cT6PP:tOsMADS6 | OsT6PP-H244D; SEQ ID NO: 3 |
| 20832 | prOsMADS6:cT6PP: tOsMADS6 | OsT6PP-I129F; SEQ ID NO: 5 |
| 12194 | 6906QC-T6PP-6900-18 | OsT6PP-WT; SEQ ID NO: 1 |
| 20569 | prOsMADS6:eFMV:e35S:cT6PP: tOsMADS6 | OsT6PP-H244D; SEQ ID NO: 3 |
| 20833 | prOsMADS6: eFMV:e35S:cT6PP: tOsMADS6 | OsT6PP-I129F; SEQ ID NO: 5 | eFMV is an enhancer from figwort mosaic virus 35S gene promoter
e35S is an enhancer from the cauliflower mosaic virus 35S gene promoter Transformants were analyzed via primary Taqman analyses to identify the low copy and backbone free events. The identified events were transferred to the green house for transplanting. All other high copy and backbone positive events were discarded. The trait events were further analyzed for secondary Taqman for confirmation of single copy of the inserted gene, and for ELISA and qRTPCR for the expression of the PMI and T6PP for event selection. ELISA and qRTPCR for PMI and/or T6PP were used to select three sets of protein or transcript expressed events (low, medium and high) for advancing to the T1 generation. 154 total events were generated with construct 20571. 129 total events were generated with construct 20832. 84 total events were generated with construct 12194. 161 total events were generated with construct 20569. 89 total events were generated with construct 20833.

Environmental stress can hit at any time in the life cycle of a plant in the field. Drought during the early part of the growing cycle and at flowering stage can cause significant yield problems in many-wheat growing regions. Young wheat plants cannot withstand limited moisture and poor seed set can be due to water stress at the anthesis stage. Drought tolerance during early plant growth and at anthesis is highly desirable. Therefore the T6PP transgenic plants will be stressed at these two development stages.

Plant response to not enough water can be evaluated through measurements of leaf water status (relative water content), canopy temperature, photosynthesis, transpiration, leaf conductance, and soil water use. After stress treatments, the plants are measured for biomass (plant height) and tiller counts, or at maturity to determine above-ground dry matter yield, grain yield, and seed mass to determine yield components as well as harvest index with the non-transgenic control or null plants to evaluate the improvement of the yield and yield component of the trait genes. Using a time-lapse image capture system, the water stress response can be documented to show the plant population response to water stress in segregating T1 population.

The evaluation of water stress tolerance during germination and seedling stages in the laboratory and growth chamber can be used to screen wheat and triticale cultivars using PEG. (Sapra, et al., 1991, Crop Science 167, 23-28, Blum et al., 1980, Euphytica 29: 727-736) Germinating seeds and hydroponically-grown seedlings can be subjected to an increasing concentration gradient of PEG solution that gave osmotic stresses of −0.3 to −0.6 MPa, or by withholding the water to screen for drought tolerant transgenics.

The following phenotypic data (1, 2 and 3) are collected using the seedling water withholding assay. The genotypic data (zygosity) for 30 plants from each event are recorded and traced. The phenotypic data of the selected plants are recorded and correlated with the zygosity. Any obvious phenotypic segregation under stress condition is tested with Chi-Square for the single insertion with expected 3:1 ratio. Events with expected segregation ratio can be expected to have improved stress tolerance.

Plant Height and Tiller Number Count:
  Plant height: From the tip of the bundle shoots to the base of the shoot.
  Tiller#: Count the number of the new tillers >2 cm.

Drought Scores at Seedling Stage: (IRRI, 1996)

| Scale | Description | Rating |
|---|---|---|
| 0 | No symptoms | High resistant |
| 1 | Slight tip drying | Resistant |
| 3 | Tip drying extended to ¼ length in most leaves | Moderate resistant |
| 5 | ¼ to ½ of the leaves fully dried | Moderate susceptible |
| 7 | More than ⅔ of all leaves fully dried | Susceptible |
| 9 | All plants apparently dead | High susceptible |

Relative Water Content Measurement: (RWC)

$$RWC(\%)=[(FW-DW)/(TW-DW)]\times 100$$

FW (Fresh weight): 4-6 fully expanded flag/leaf discs—10-15° C. and weigh.
TW (Turgor weight): Hydrate the leaf for 4 h in petri dish with dd water—under room light and temperature and weigh
DW (Dry weight): Oven-dried at 80° C. for 72 h and weigh after cooled in a desiccators
Schonfeld et al. (1988) Crop Science 28:526-531

Twenty-one 20571 T0 events were selected for seedling water withholding screening and at T2 seed generation. Seven events were selected for low expression of the transgene, seven events were selected for medium expression of the transgene and seven events were selected for high expression of the transgene. A similar number of the T0 events will be selected for all other four constructs (20832, 12194, 20833 and 20569) for water withholding screening at T1 seedling level and T2 anthesis stage.

The transcript expression using qRTPCR for OsT6PP-I129F and PMI of five 20832 events were performed and showed T6PP-I129F expressed only at reproductive tissues of 3 out of 5 events, whereas PMI expressed at all plants.

| Plant # | Construct # | PMI To Endo Control (x1000) | T6PP To Endo Control (x1000) | Tissue |
|---|---|---|---|---|
| 1 | 20832 | 6605.06 | 63.93 | Flag leaf |
| 1 | 20832 | 4418.36 | 38.44 | Flag leaf node |
| 1 | 20832 | 3392.21 | 51.70 | Spikelet w/seed |
| 1 | 20832 | 4657.83 | 96.48 | Spikelet w/o seed |
| 2 | 20832 | 9041.99 | 3.21 | Flag leaf |
| 2 | 20832 | 3518.87 | 35.52 | Flag leaf node |
| 2 | 20832 | 1184.24 | 10.97 | Spikelet w/seed |
| 2 | 20832 | 6222.36 | 30.21 | Spikelet w/o seed |
| 3 | 20832 | 10938.95 | 0.00 | Flag leaf |
| 3 | 20832 | 1576.16 | 0.00 | Flag leaf node |
| 3 | 20832 | 740.58 | 0.00 | Spikelet w/seed |
| 3 | 20832 | 1504.65 | 0.00 | Spikelet w/o seed |
| 4 | 20832 | 3368.54 | 0.00 | Flag leaf |
| 4 | 20832 | 1478.55 | 0.00 | Flag leaf node |
| 4 | 20832 | 444.83 | 0.00 | Spikelet w/seed |
| 4 | 20832 | 1480.28 | 0.00 | Spikelet w/o seed |
| 5 | 20832 | 4463.78 | 0.00 | Flag leaf |
| 5 | 20832 | 2673.50 | 0.05 | Flag leaf node |
| 5 | 20832 | 1000.36 | 5.44 | Spikelet w/seed |
| 5 | 20832 | 2315.88 | 1.26 | Spikelet w/o seed |

Plant number 4 is a negative control containing PMI but no T6PP gene.

Example 12

Expression of Modified T6PP in Soy

The trehalose pathway can be exploited to improve yield in dicot plants. For example, soybean (*Glycine max*) responds to drought by dropping flowers, dropping pods, reducing seeds per pod, aborting seeds within pods, and reducing the size of the seed (Liu et al., 2003). Producing a drought tolerant soybean plant will increase yield by preventing the loss of flowers, pods, seeds and/or improving seed size. This technology can be deployed in a crop like soy bean by identifying trait gene regulatory sequence that specifically operates in developing flowers, designing an expression cassette based on one or more of the candidate genes and linking the expression cassette to wildtype or modified trehalose-6-phosphate phosphatase. The MADS gene family is an excellent source of trait gene regulatory sequence that is active in developing flowers (Jack T (2001) Plant Mol Biol 46:515-520). The MADS gene family is highly conserved in plants (Munster et al., (2002) Maydica 47:287-301; De Bolt et al., (2003) Trends Plant Science 8:475-483). Primary genetic information from model plants can be used to identify orthologous soy bean genes (Hecht et al. (2005) Plant Physiol 137:1420-1434). Coupling protein and DNA sequence information with genetic or expression data enables those skilled in the art to develop tightly regulated expression cassettes that are active in soybean flowers, such as, GmSEP1 promoters, (Huang et al. (2009) Gene 438:40-48; APETALA1-like promoters, (Chi et al., (2011) J Plant Physiol 168:2251-2259); an OsMADS promoter (U.S. Pat. No. 8,129,588). For example, the OsMADS6-expression cassette, or a variant thereof, could be used directly in transgenic soy to enable the trait.

Once the appropriate expression vector is designed, a transgenic soybean plant comprising the expression cassette can be created using well known techniques, such as, particle bombardment-mediated transformation method (Hadi et al. (1996) Plant Cell Reports 15:500-505) or *Agrobacterium*-mediated transformation using mature or immature seed targets (US patent application 20040034889; WO08112044). For example, expression cassettes comprising OsT6PP and variant coding sequence driven by *Arabidopsis* AGAMOUS promoter is linked with an EPSPS selectable marker gene cassette to form a binary vector for *Agrobacterium*-mediated transformation. Regenerated plantlets were tested for the presence of both EPSPS marker gene and T6PP transgene sequences by quantitative TaqMan PCR analysis (Ingham et al., (2001) Biotechniques 31(1) 132-4, 136-140). Transgenic plants are grown in greenhouse for setting seeds.

The transgenic soybean plants can then be screened for response to water deficit using the following assay: T1 seed segregating for a single copy of the transgene are grown to early reproductive development. At this point plants are organized into two groups, the first group remains unstressed and the second group receives half the water required to maintain unstressed growth. Each group consists of null, hemizygous, and homozygous siblings. Plants are maintained in these conditions for three-four weeks. During this period flower development and pod set are monitored on a daily basis. At the end of the study period data resulting from each genotype are compared. There should be little to no difference between genotypes in the unstressed group. The water deficit group will show that trait positive plants have more flowers and more pods per plant compared to null plants. Alternatively, homozygous trait positive and null siblings can be grown in test plots using standard cultivation procedures. Plots are organized into unstressed and water deficit blocks. The water deficit blocks will receive half the required water during the flowering period. Yield data for each plot are collected at the end of the growing season and compared. The trait positive plots will exhibit improved yield compared to null plots in the water deficit group.

Example 13

Expression Profiling of High Yielding OsT6PP Transgenic Plants Tissue Types and Samples Examined Seven tissue types were collected, namely; leaf, leaf below ear, node, primary shank, primary ear, secondary ear, and stem. Three pedigrees were examined: the check comprising the untransformed variety, OsT6PP-I129f (SEQ ID NO: 5), and OsT6PP-H244D (SEQ ID NO: 3). Three pedigrees were either grown under well watered conditions or subjected to drought stress. Ten biological replicates were sampled for each tissue/condition, leading to a total of 420 samples. Not all of the samples were taken, however, for various technical reasons. A total of 407 samples were made available for RNA purification and labeling for microarray hybridization.

Standard protocols were used for RNA purification, quality assessment, labeling and hybridization. Not all samples had sufficient quality or quantity of RNA for microarray hybridization. A total of 392 arrays were processed and scanned.

Data Normalization and Preprocessing:

For this study, the Maize Affymetrix GeneChip, sySYNG007a, was utilized. Raw CEL files for all of the experiments were analyzed using a custom protocol that analyzes the quality of the microarrays based on a number of criteria, performs and background corrections, and condenses the data using the Bioconductor RMA algorithm. From this analysis, 6 slides were found to be of potentially poor quality. However, the overall chip images were sufficient for analysis, and control 5'/3' probe ratios were adequate, so the experiments were not excluded. For this study, a custom CDF (Chip Description File) designed to map probes to the maize genome was used. The CDF also maps to Unigenes from NCBI and full length cDNAs from MaizeGDB. To determine background level noise, a series of control probe sets were analyzed. Spike in controls of *Bacillus* genes were not used during hybridization, so these probe sets can be considered background noise. Background was determined to be two standard deviations above the mean value of all of the *Bacillus* probe sets. The background signal noise determined was used to threshold the data. Threshold values were set to exclude any probe sets that had signal intensities lower than background in all of the experiments. Probe sets were kept for analysis if the signal was greater than the background in at least 3 experiments. Principal components analysis and hierarchical clustering were used to assess quality of the experiments and define any potential outliers.

Pathway Analysis

In an attempt to provide Biological context to the results from the univariate statistical tests, enrichment analyses were conducted using similar tests. There are multiple ways to conduct pathway analysis, however for these experiments the most appropriate method was Gene Set Enrichment Analysis (GSEA), using software available from the Broad Institute called GSEA. The GSEA algorithm requires that genes be clustered into gene sets according to some Biological criteria. For this study, two such gene sets were utilized. First, sets of gene models from the maize genome were ordered into gene sets according to grouping into pathways available from MaizeCyc (at the following site: pathway.gramene.org/MAIZE). The second list of gene sets was made from probe sets on a the custom designed maize GeneChip using the custom CDF file used to condense probe information for this study. The probe sets representing transcripts from gene models from maize genome were grouped into gene sets according to the Gene Ontology terms assigned to the gene models from Maize GDB (at the following site: maizegdb.org/). The GSEA algorithm rank orders genes from 2 different samples to create a ranked list of genes and this information is used to determine if genes within the ranked lists are in shared gene sets. P values are calculated based on the likelihood that genes could be found in ranked lists of gene sets by random chance. The P values are then corrected by multiple testing to generate false discovery rates for all gene sets. For this analysis, all of the pairwise comparisons were subjected to GSEA using pathways from MaizeCyc and Gene Ontology (GO) terms from MaizeGDB. In addition, only probe sets representing single genes were analyzed. That is, probe sets possibly mapping to multiple genes were discarded for GSEA.

Multivariate Statistics

A series of multivariate analyses were conducted to determine the greatest sources of variance in the data. Principal components analysis (PCA) of all of the data revealed that the greatest source of variance was tissue type. Leaf and below ear leaf tissue (source tissues) are clearly separated from the other sink tissues.

To further determine sources of variance, individual tissue types were analyzed using PCA. Results indicated drought had a dramatic effect on gene expression variation in all tissues examined, with the possible exception of secondary ear tissues. It should be noted that fewer samples were available for secondary ear tissues. Due to uneven sampling of this tissue type gene expression may not have been accurately measured. Systematic variance not due to pedigree or stress, such as sampling or plot location may have had a significant impact on gene expression in secondary ear tissue. Although pedigree was not the major source of variance within individual tissue types, it did have a distinct effect and was apparent in the second principal component in most tissues. Interestingly, greater variance due to pedigree was detected in drought stressed samples. Although there was not always a clear component explained by pedigree alone, it was clear from PCA that there was greater variance between pedigrees under drought stress compared to the well watered condition. For example, it is clear from PCA that the first PC separated the samples grown in well watered from the drought stressed conditions. The second principal component, explaining the greatest source of variance after PC 1 is removed, indicates a separation of drought treated samples by pedigree. There is not as clear a separation of samples as with drought stressed versus well watered plants. However, there is a much tighter grouping (i.e., less variance) of the check and OsT6PP-H244D pedigrees examined from well watered samples compared to the drought treated samples. The trend of component 2 can mostly be explained by separation of samples from the check and OsT6PP-H244D pedigrees under drought stress. This could be interpreted as the check and OsT6PP-H244D pedigrees having similar patterns of gene expression under well watered conditions, but distinct gene expression profiles under drought stress. This is consistent with providing a yield benefit under drought stress. A similar increase in variance under drought stress was detected in other tissues tested and much of the variance could be explained by pedigree.

In summary, multivariate analyses identified the major sources of variance as tissue type and drought stress, with a lesser effect on gene expression differences caused by pedigree (i.e., presence of the transgene). Pedigree effect was tested by comparing the OsT6PP-H244D with the control check hybrid line. In most tissues tested, both sink and source tissues, there was a greater variance that could be explained by pedigree in samples collected from drought stressed plants than samples from well watered plants. Thus, gene expression differences between the lead event and the check line were most obvious in drought stressed plants.

Expression of T6PP and TPS Genes

As the event being characterized included the T6PP gene expressed from the OsMADS6 promoter, it was of interest to determine the level of expression of the transgene and/or expression of endogenous T6PP genes. Also, expression of T6PP may influence expression of Trehalose-6-phosphate synthase. Both proteins are known to be encoded by several gene family members in maize. Attempts were made to only analyze probe sets that mapped to either individual transcript isoforms, or multiple isoforms within one locus, to determine expression of individual gene family members. A total of eight probe sets representing T6PP and fourteen probe sets representing TPS were analyzed for expression level in all tissues, both stressed and unstressed from both check and OsT6PP-H244D. What was found was that no T6PP or TPS probe sets had particularly higher expression in any tissues in the OsT6PP-H244D event, suggesting that the transgene in the event does not have a drastic effect on trehalose pathway genes, and there is not a detectably higher level of expression of any endogenous T6PP gene. It is unclear as to whether any of the probe sets hybridize sufficiently to the transgenic T6PP in the event to detect a reliable signal. One would expect a higher level of expression of T6PP in the transgenic event line. These results were confirmed by direct TTESTs in each tissue testing for differential expression of the T6PP and TPS genes between the check and OsT6PP-H244D. In no tests were any of the isoforms shown to have greater than 2 fold expression difference between the 2 pedigrees in any tissue with any degree of statistical significance (P value <0.1). However, there was clear evidence that isoforms of both genes were responsive to drought stress in some tissues. Interestingly, expression of one of the T6PP isoforms, GRMZM2G347280_T01, was repressed in response to drought stress in leaf (source) tissue, however expression was increased in response to drought stress in primary ear tissue and primary shank tissues. Also, there was definite tissue specificity of the T6PP representative probe sets. For example, the T6PP encoding gene GRMZM2G080354 was most highly expressed in secondary ear tissue; GRMZM2G112830 was barely detectable in all tissues with the exception of stem, with one alternate transcript, GRMZM2G112830_T07, likely expressed in node as well; GRMZM2G174396_T01 was most highly expressed in node tissue, and GRMZM2G178546_T01 was most highly expressed in Primary Ear. There were similar tissue specific and drought responsive members of the TPS family that were represented by probe sets. Of note was the gene GRMZM2G019183 which had low level expression in all tissues, however was turned on in response to drought stress in node, primary ear, and primary shank tissues. Relatively high levels of expression of several TPS genes were found in secondary ear tissue. Interestingly, there was not a significant difference in expression of these genes in response to drought stress in secondary ear, even for genes that were responsive to drought in other tissues. As the construct used for this event used the T6PP gene from rice, it is likely that none of the probe sets matched the sequence sufficiently to hybridize with the maize probe sets on the array. Therefore, the results presented likely represent expression level of only endogenous genes.

Univariate Analysis and Pair Wise Comparisons

A series of pair wise comparisons were performed using a Welch T Test to determine gene differentially expressed between 2 samples (the check and OsT6PP-H244D). The comparisons made focused on the original experimental design to test the difference in expression between the check and OsT6PP-H244D lines in well watered or drought conditions in all tissues (7 tests for each condition) and also tested the difference in gene expression in plants grown under well watered or drought conditions in either pedigree in all tissues (14 comparisons). Results of the tests are summarized in the Tables below. Probe sets were reported to be differentially expressed in the Welch T Test P value was less than 0.01 and the fold change (ratio of means of biological replicates) was greater than 2 fold. Additionally, to determine if there were any genes that had significantly different response to drought as result of the effect of the pedigree, a linear model was run to test for interaction effects. The results of Table 4 indicate numbers of probe sets that had a significant interaction effect of water X pedigree with a FDR less than 0.05. In general, the results completely support the result from the multivariate analyses, with all tissues, with the exception of secondary ear, showing a large impact of drought on gene expression. Interestingly, in all tissues, there were more genes responsive to drought in the OsT6PP-H244D event compared with check line (Table 1). These results may indicate that the OsT6PP-H244D event is more responsive to drought stress at the level of gene expression changes.

TABLE 1

Summary of results from Welch Test: well watered vs drought

| Tissue | Condition | Genotype | Test | # differentially expressed Probe sets |
|---|---|---|---|---|
| Leaf | Well watered or drought | CHECK | Water vs Drought | 1515 |
| Leaf | Well watered or drought | OsT6PP-I129F | Water vs Drought | 1286 |
| Leaf | Well watered or drought | OsT6PP-H244D | Water vs Drought | 2224 |
| Leaf below ear | Well watered or drought | CHECK | Water vs Drought | 1487 |

TABLE 1-continued

Summary of results from Welch Test: well watered vs drought

| Tissue | Condition | Genotype | Test | # differentially expressed Probe sets |
|---|---|---|---|---|
| Leaf below ear | Well watered or drought | OsT6PP-I129F | Water vs Drought | 1472 |
| Leaf below ear | Well watered or drought | OsT6PP-H244D | Water vs Drought | 2344 |
| Node | Well watered or drought | CHECK | Water vs Drought | 1296 |
| Node | Well watered or drought | OsT6PP-I129F | Water vs Drought | 2423 |
| Node | Well watered or drought | OsT6PP-H244D | Water vs Drought | 2257 |
| Primary Ear | Well watered or drought | CHECK | Water vs Drought | 1310 |
| Primary Ear | Well watered or drought | OsT6PP-I129F | Water vs Drought | 1557 |
| Primary Ear | Well watered or drought | OsT6PP-H244D | Water vs Drought | 1769 |
| Primary Shank | Well watered or drought | CHECK | Water vs Drought | 1688 |
| Primary Shank | Well watered or drought | OsT6PP-I129F | Water vs Drought | 3143 |
| Primary Shank | Well watered or drought | OsT6PP-H244D | Water vs Drought | 4098 |
| Secondary Ear | Well watered or drought | CHECK | Water vs Drought | 128 |
| Secondary Ear | Well watered or drought | OsT6PP-I129F | Water vs Drought | 4076 |
| Secondary Ear | Well watered or drought | OsT6PP-H244D | Water vs Drought | 290 |
| Stem | Well watered or drought | CHECK | Water vs Drought | 708 |
| Stem | Well watered or drought | OsT6PP-I129F | Water vs Drought | 1294 |
| Stem | Well watered or drought | OsT6PP-H244D | Water vs Drought | 2047 |

Differentially expressed probe sets = probe sets with P value from Welch Test < 0.01 and fold change (ratio of means of samples from the 2 groups tested) > 2.

TABLE 2

Summary of results from Welch Test: well watered: CHECK vs DTOsT6PP-H244D

| Tissue | Condition | Genotype | Test | # differentially expressed Probe sets |
|---|---|---|---|---|
| Leaf | Well watered | Check v event | CHECK vs OsT6PP-I129F | 33 |
| Leaf | Well watered | Check v event | CHECK vs OsT6PP-H244D | 23 |
| Leaf Below Ear | Well watered | Check v event | CHECK vs OsT6PP-I129F | 23 |
| Leaf Below Ear | Well watered | Check v event | CHECK vs OsT6PP-H244D | 15 |
| Primary Ear | Well watered | Check v event | CHECK vs OsT6PP-I129F | 89 |
| Primary Ear | Well watered | Check v event | CHECK vs OsT6PP-H244D | 98 |
| Node | Well watered | Check v event | CHECK vs OsT6PP-I129F | 146 |
| Node | Well watered | Check v event | CHECK vs OsT6PP-H244D | 19 |
| Primary Shank | Well watered | Check v event | CHECK vs OsT6PP-I129F | 90 |
| Primary Shank | Well watered | Check v event | CHECK vs OsT6PP-H244D | 111 |
| Secondary Ear | Well watered | Check v event | CHECK vs OsT6PP-I129F | 4542 |
| Secondary Ear | Well watered | Check v event | CHECK vs OsT6PP-H244D | 342 |
| Stem | Well watered | Check v event | CHECK vs OsT6PP-I129F | 111 |
| Stem | Well watered | Check v event | CHECK vs OsT6PP-H244D | 196 |

TABLE 3

Summary of results from Welch Test: Drought: CHECK vs DTOsT6PP-H244D

| Condition | Genotype | Test | # differentially expressed Probe sets |
|---|---|---|---|
| Leaf | Drought | Check v event | CHECK vs OsT6PP-I129F | 20 |
| Leaf | Drought | Check v event | CHECK vs OsT6PP-H244D | 102 |
| Leaf Below Ear | Drought | Check v event | CHECK vs OsT6PP-I129F | 43 |
| Leaf Below Ear | Drought | Check v event | CHECK vs OsT6PP-H244D | 105 |
| Primary Ear | Drought | Check v event | CHECK vs OsT6PP-I129F | 16 |
| Primary Ear | Drought | Check v event | CHECK vs OsT6PP-H244D | 87 |
| Node | Drought | Check v event | CHECK vs OsT6PP-I129F | 21 |
| Node | Drought | Check v event | CHECK vs OsT6PP-H244D | 188 |
| Primary Shank | Drought | Check v event | CHECK vs OsT6PP-I129F | 28 |
| Primary Shank | Drought | Check v event | CHECK vs OsT6PP-H244D | 218 |
| Secondary Ear | Drought | Check v event | CHECK vs OsT6PP-I129F | 17 |
| Secondary Ear | Drought | Check v event | CHECK vs OsT6PP-H244D | 200 |
| Stem | Drought | Check v event | CHECK vs OsT6PP-I129F | 30 |
| Stem | Drought | Check v event | CHECK vs OsT6PP-H244D | 298 |

TABLE 4

Summary of genes with interaction effect of drought and pedigree

| Tissue | Test Y ~ genotype: water | # differentially expressed Probe sets (FDR > 0.05) |
|---|---|---|
| Leaf | CHECK vs OsT6PP-H244D | 21 |
| Leaf Below Ear | CHECK vs OsT6PP-H244D | 130 |
| Primary Ear | CHECK vs OsT6PP-H244D | 1 |
| Node | CHECK vs OsT6PP-H244D | 152 |
| Primary Shank | CHECK vs OsT6PP-H244D | 376 |
| Secondary Ear | CHECK vs OsT6PP-H244D | 0 |
| Stem | CHECK vs OsT6PP-H244D | 5844 |

Although many of the genes responsive to drought were common in both pedigrees, there were many genes that were only detected as differentially expressed by drought stress in OsT6PP-H244D. Many genes were found to be unique to OsT6PP-H244D in response to drought stress. The results are similar to the results of the linear model to find genes that had an interaction effect between the two experimental factors drought and pedigree. The reason for the difference in the numbers of genes from the 2 analyses is likely because the cut off used in the TTESTs was a P-value of less than 0.01 and the statistical cut off for the data in Table 4 was false discovery rate less than 0.05. The false discovery rate calculated from multiple testing correction is more stringent and a more reliable method of determining genes that are differentially expressed. The linear model is a better test of interaction effects then overlapping results of genes found to be differentially expressed from T-tests as the model incorporates all of the data in the factorial experimental design. However, combining results from both tests can be a powerful method to identify genes with differential responses to 2 factors, as will be described in more detail.

The major differences between the pedigrees were detected during drought stress and in sink tissue, including node tissue. Linear models showed significant interaction effects in Node, primary shank and stem as well. The combined results suggest most of the interaction effects were due to differences in what genes change under drought stress in the two pedigrees tested. Under well watered conditions there were fewer differences in gene expression between the check and OsT6PP-H244D.

Pathway Analysis

In an attempt to provide Biological context to the results from the univariate statistical tests, enrichment analyses were conducted using similar pairwise tests. GSEA was run on the data to test for enrichment of pathways from MaizeCyc and GO terms from MaizeGDB. As the node tissue was noted to be of particular interest, GSEA results may be more easily interpretable from that tissue. It should be noted that the pathway analyses highlighted here focused on pairwise comparisons using all of the data in a GSEA model to increase the power of the enrichment test compared with using pre-computed gene lists. The pair wise comparisons performed focused on differences of the check and OsT6PP-H244D which the previous Welch tests indicated had relatively few differences in gene expression. Therefore, the false discovery rates (FDR) calculated for most of the comparisons were generally high although some of the P values calculated showed statistically significant results. It should be noted that although the P values are significant, the FDR q values may be a better indication of the statistically likelihood of pathways or GO terms being enriched in a given gene set. Tables 5 and 6 indicate the gene sets enriched in OsT6PP-H244D compared to the check in node tissue under drought stress.

TABLE 5

Gene Set Enrichment Analysis: Node tissue under drought: CHECK vs OsT6PP-H244D

| NAME (MaizeCyc Pathway) | NOM p-val | FDR q-val |
|---|---|---|
| GLYCINE_CLEAVAGE_COMPLEX | 0.00 | 0.14 |
| SULFITE_OXIDATION_III | 0.01 | 0.10 |
| PENTOSE_PHOSPHATE_PATHWAY_ (OXIDATIVE_BRANCH) | 0.00 | 0.12 |
| FOLATE_TRANSFORMATIONS_I | 0.00 | 0.13 |
| SULFATE_REDUCTION_II_(ASSIMILATORY) | 0.02 | 0.18 |
| FOLATE_TRANSFORMATIONS_II_(PLANTS) | 0.01 | 0.15 |
| PHOTOSYNTHESIS_LIGHT_REACTIONS | 0.01 | 0.16 |
| FOLATE_POLYGLUTAMYLATION | 0.01 | 0.16 |
| FATTY_ACID_ACTIVATION | 0.01 | 0.15 |

TABLE 5-continued

Gene Set Enrichment Analysis: Node tissue under drought: CHECK vs OsT6PP-H244D

| NAME (MaizeCyc Pathway) | NOM p-val | FDR q-val |
|---|---|---|
| NADH_TO_CYTOCHROME_BD_OXIDASE_ELECTRON_TRANSFER | 0.01 | 0.24 |

TABLE 6

Gene Set Enrichment Analysis: Node tissue under drought: CHECK vs OsT6PP-H244D

| NAME | NOM p-val | FDR q-val |
|---|---|---|
| UBIQUINOL-CYTOCHROME-C REDUCTASE ACTIVITY | 0.01 | 0.14 |
| FOLIC ACID-CONTAINING COMPOUND BIOSYNTHETIC PROCESS | 0.00 | 0.18 |
| PHOSPHOGLUCONATE DEHYDROGENASE (DECARBOXYLATING) ACTIVITY | 0.00 | 0.18 |
| NEGATIVE REGULATION OF TRANSCRIPTION, DNA-DEPENDENT | 0.00 | 0.23 |
| MEDIATOR COMPLEX | 0.01 | 0.26 |
| RNA POLYMERASE II TRANSCRIPTION COFACTOR ACTIVITY | 0.01 | 0.22 |
| CLATHRIN ADAPTOR COMPLEX | 0.01 | 0.25 |
| PENTOSE-PHOSPHATE SHUNT | 0.00 | 0.40 |
| GLUCOSE-6-PHOSPHATE DEHYDROGENASE ACTIVITY | 0.00 | 0.35 |
| PLASTID | 0.03 | 0.36 |

Other tissues were tested but the node tissue under stress found a pathway of particular interest, namely, the Pentose Phosphate Shunt pathway. It is notable as this is an energy producing pathway that might be affected in only the OsT6PP-H244D plants under drought stress. Although not to be limited by theory, this could be potentially one of the mechanisms that enable the OsT6PP-H244D event to maintain energy production to produce higher yield under drought conditions. It clearly shows an alternative energy production pathway affected by drought stress in only the event and not necessarily in the check hybrid line. The enzymes in the pentose phosphate pathway is encoded by many genes and their transcription has been shown to be responsive a variety of different stimuli. The pathway is known to be involved in production of secondary metabolites. Another pathway identified in different sink tissues as being differentially regulated in OsT6PP-H244D was Nitrate Assimilation, or Nitrogen metabolism. This was interesting to find due to results from previous studies, including studies of altered metabolism of maize lines under drought stress that identified amino acid biosynthesis, especially N storage amino acids at higher concentration in drought treated plants. Additionally, a recent study found plants subjected to chronic N stress were less responsive to water deficit than plants grown under optimal N conditions. Although not to be limited by theory, plants undergoing drought stress might utilize normal N metabolic pathways, especially production of N storage amino acids to assimilate possibly toxic concentrations of ammonia that may build up in drought stressed plant tissues. Thus, these data give support to an ammonia detoxification hypothesis and suggest that perhaps the T6PP expressing OsT6PP-H244D event may be better conditioned to utilize a N metabolic mechanism of adaptation to water deficit.

Carbonic Anhydrase Transcript Identified with Increased Expression in OsT6PP-H244D Two hypotheses of how gene expression profiling might reveal differences between the OsT6PP-H244D event and the check were tested. The first hypothesis is that a distinct set of genes are altered specifically in OsT6PP-H244D under drought stress and not in the check. Such a set of genes may play a role in higher yield of the OST6PP-H244D line compared to the check under drought stress. This hypothesis was tested using results from the pairwise comparisons and from the linear model. The results of T-Tests from Table 1 were compared to the genes identified in the linear model (Table 4). Two tissue samples were tested, as they had a substantial number of genes that had an interaction effect of the 2 factors drought stress and pedigree. In Node tissue, a total of 1,127 genes had altered expression under drought stress in OST6PP-H244D that were not significantly changed by drought stress in the check. The intersect of this list of genes and the 152 genes with an drought X pedigree interaction effect from the linear model of Node tissues (Table 4) identified 22 probe sets specifically effected by drought stress in only the OsT6PP-H244D event. One of the genes identified was Carbonic Anhydrase. Also included on the list were several probe sets annotated as serine peptidases, as well as an aquaporin gene TIP4. A separate analysis of the same linear model identified Carbonic Anhydrase as having higher expression in OsT6PP-H244D regardless of tissue type or water condition. In fact, Carbonic Anhydrase was represented by 2 probe sets in a short list of probe sets with greater than 2 fold or higher expression in OsT6PP-H244D across all tissues types. Many of the other genes in this list were unknown genes. These data suggest that at least one gene family member of carbonic anhydrases is expressed at a higher level in OsT6PP-H244D than in the check. Expression of this same carbonic anhydrase was analyzed in the back up even, OsT6PP-I129F and found to be specific to OsT6PP-H244D.

Results of analyses across all tissues and conditions found a relatively short list of probe sets (28) that were significantly in the OsT6PP-H244D line compared with the check line. At least two probe sets on that list were annotated as carbonic anhydrases. Carbonic anhydrase is active in C4 photosynthesis by helping to fix carbon dioxide and assimilate carbon for the plant. A very significant increase in expression was detected in OsT6PP-H244D of at least one isoform of one family member CA.

Although the foregoing invention has been described in some detail by way of illustration and example for purposes of clarity and understanding, it will be clear to those of skill in the art that certain changes and modifications may be practiced within the scope of the appended claims.

What is claimed is:

1. A method for increasing tolerance of a plant to abiotic stress, the method comprising:
   a) introducing into a plant cell an expression cassette, wherein the expression cassette comprises a polynucleotide operably linked to a promoter that ensures transcription of said polynucleotide in a plant, wherein said polynucleotide encodes a polypeptide, wherein said polypeptide has trehalose-6-phosphate phosphatase activity, wherein the polypeptide has been modified to have decreased enzymatic activity as compared to the unmodified trehalose-6-phophate phosphatase;
   b) regenerating a plant from the plant cell of a); and thereby
   c) producing a plant with increased tolerance to abiotic stress, wherein said abiotic stress comprises water stress, wherein the plant is maize; and
   wherein said modification is selected from the group consisting of OsT6PP-H244D, OsT6PP-A102V, and OsT6PP-I129F.

2. The method of claim 1, wherein water stress is caused by drought.

* * * * *